(12) United States Patent
Arsac et al.

(10) Patent No.: US 10,240,213 B2
(45) Date of Patent: Mar. 26, 2019

(54) METHOD FOR IN VITRO DIAGNOSIS OR PROGNOSIS OF TESTICULAR CANCER

(71) Applicant: BIOMERIEUX, Marcy L'Etoile (FR)

(72) Inventors: Maud Arsac, Saint-Chamond (FR); Bertrand Bonnaud, Verin (FR); Francois Mallet, Villeurbanne (FR); Jean-Philippe Pichon, Clermont-Ferrand (FR)

(73) Assignee: BIOMERIEUX, Marcy l'Etoile (FR)

( * ) Notice: Subject to any disclaimer, the term of this patent is extended or adjusted under 35 U.S.C. 154(b) by 118 days.

(21) Appl. No.: 13/739,447

(22) Filed: Jan. 11, 2013

(65) Prior Publication Data
US 2013/0172209 A1 Jul. 4, 2013

Related U.S. Application Data

(63) Continuation of application No. 13/138,000, filed on Sep. 23, 2011, now abandoned, which is a continuation of application No. 12/918,166, filed as application No. PCT/FR2009/050390 on Mar. 10, 2009, now abandoned.

(30) Foreign Application Priority Data

Mar. 12, 2008 (FR) ...................... 08 51619

(51) Int. Cl.
*C12Q 1/6886* (2018.01)
*C12Q 1/70* (2006.01)

(52) U.S. Cl.
CPC ........... *C12Q 1/702* (2013.01); *C12Q 1/6886* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS 5,858,723 A 1/1999 Mueller-Lantzsch
2001/0051344 A1 12/2001 Shalon et al.

OTHER PUBLICATIONS

Fossa et al . Journal of the National Cancer Institute. 2005. 97(14): 1056-1066.*
Travis et al. Journal of the National Cancer Institute. 2005. 97(18): 1354-1365.*
Sant et al. European Journal of Cancer. 2007. 43: 585-592.*
Stephenson et al. J Clin Oncol. 2005. 23: 2781-2788.*
Crowell et al. Biochem Soc Trans. 2007. 35(Pt 3):629-633.*
Casau et al. J. Virol. 1999. 73(12): 9976-9983.*
Flockerzi et al. BMC Genomics. 2008. 9:354.*
Schon et al. Virology. 2001. 279:280-291.*

(Continued)

*Primary Examiner* — Joseph G. Dauner
(74) *Attorney, Agent, or Firm* — Oliff PLC

(57) ABSTRACT

The invention relates to a method for in vitro diagnosis or prognosis of testicular cancer which comprises a step of detecting the presence or absence of at least one expression product from at least one nucleic acid sequence selected from the sequences identified in SEQ ID NOS: 1 to 6 or from the sequences which exhibit at least 99% identity with one of the sequences identified in SEQ ID NOS: 1 to 6, to isolated nucleic acid sequences and to the use thereof as a testicular cancer marker.

24 Claims, 9 Drawing Sheets
Specification includes a Sequence Listing.

(56) References Cited

OTHER PUBLICATIONS

Seifarth et al. Journal of Virology. 2005. 79(1):341-352.*
Kim et al. Arch Virol. 2008. 153:1587-1591.*
Parseval et al. Journal of Virology. 2003. 77(19):10414-10422.*
Yi et al. Journal of General Virology. 2004. 85:1203-1210.*
Choi. The Scientist. Dec. 21, 2006. Retrieved on Sep. 19, 2016 from the internet: http://www.the-scientist.com/?articles.view/articleNo/24630/title/-Silent--mutations-are-not-always-silent/.*
Pagani et al. PNAS. 2005. 102(18):6368-6372.*
Sauna et al. Cancer Res. 2007. 67(20):9609-6912.*
Kimchi-Sarafty et al. Science. 2007. 315(5811):525-528.*
Examiner's Table 1 (Prepared on May 19, 2017 using the online BLAST tool).*
Nellaker et al. Retrovirology 2006. 3:44, 11 pages. (Year: 2006).*
Yao et al. Genes, Brain and Behavior. 2008. 7(1):103-12. Epub date of Jun. 7, 2007. (Year: 2007).*
Shaw et al. Am Fam Physician. 2008. 77(4):469-476. (Year: 2008).*
Yi et al.; "Expression of the human endogenous retrovirus HERV-W family in various human tissues and cancer cells;" *Journal of General Virology*; 2004; pp. 1203-1210; vol. 85; SGM; Great Britain.
Goedert et al; "High Prevalence of Antibodies against HERV-K10 in Patients with Testicular Cancer but not with AIDS;" *Cancer Epidemiology, Biomarkers & Prevention*; Apr. 1999; pp. 293-296; vol. 8.
Yi et al.; "Expression and Identification of HERV-W Family in Japanese Monkeys (*Macaca fuscata*);" *Zoological Science*; 2004; pp. 649-659; vol. 21; Zoological Society of Japan.
Nickerson et al; "DNA sequence diversity in a 9.7-kb region of the human lipoprotein lipase gene;" *Nature Genetics*; Jul. 1998; pp. 233-240; vol. 19; Nature America Inc.
Cottrell; "Molecular diagnostic applications of DNA methylation technology; Clinical Biochemistry;" 2004; pp. 595-604; vol. 37; *The Canadian Society of Clinical Chemists*.

International Search Report dated Sep. 15, 2009 in corresponding International Application No. PCT/FR2009/050390.
Written Opinion of the International Searching Authority dated Sep. 15, 2009 in corresponding International Application No. PCT/FR2009/050390.
Genbank Accession No. AC024022.6, Available May 13, 2005.
Genbank Accession No. AC092843.4, Available Apr. 21, 2005.
Genbank Accession No. NT_024524.13, Available Feb. 29, 2008.
Genbank Accession No. AC0030141.1, Available Feb. 4, 2000.
Genbank Accession No. AP001599.1, Available Apr. 29, 2000.
Genbank Accession No. NT_007933.14, Available Feb. 29, 2008.
Pichon et al., "Multiplex Degenerate PCR Coupled with an Oligo Sorbent Array for Human Endogenous Retrovirus Expression Profiling;" Nucleic Acids Research, vol. 34, No. 6, pp. 1-10, Mar. 22, 2006.
Forsman et al., "Development of Broadly Targeted Human Endogenous Gammaretroviral pol-based Real Time PCRs Quantitation of RNA Expression in Human Tissues;" Journal of Virological Methods, vol. 129, pp. 16-30, 2005.
Whitehead et al., "Variation in Tissue-Specific Gene Expression Among Natural Populations;" Genome Biology, vol. 6, pp. R13-R13.14, 2005.
Roman-Roman et al., "Identification of Genes Regulated During Osteoblastic Differentiation by Genome-Wide Expression Analysis of Mouse Calvaria Primary Osteoblasts In Vitro;" Bone, vol. 32, pp. 474-482, 2003.
Chan et al., "Integrating Transcriptomics and Proteomics;" G&P Magazine, vol. 6, No. 3, pp. 20-26, 2006.
Hoshikawa et al., "Hypoxia Induces Different Genes in the Lungs of Rats Compared with Mice;" Physical Genomics, vol. 12, pp. 209-219, 2003.
Thisted, "What is a P-Value?;" The University of Chicago, pp. 1-6, 1998.

* cited by examiner

HW2TT Locus

Normal testicle 12 clones

Tumoral testicle 12 clones

ERVWE1 Locus

Normal testicle 10 clones

Tumoral testicle 10 clones

SEQUENCE LISTING

<160> NUMBER OF SEQ ID NOS: 62

<210> SEQ ID NO 1
<211> LENGTH: 7487
<212> TYPE: DNA
<213> ORGANISM: Homo sapiens

<400> SEQUENCE: 1

| | | | | | |
|---|---|---|---|---|---|
| tgagaaacag | gactagttag | atttcctagg | ccaactaaga | atccctaagc ctagctggga | 60 |
| aggtgatcgc | atccaccttt | aaacacgggc | ttgcaactta | gctcacacct gaccaatcag | 120 |
| gtagtaaaga | gagctcacta | aaatgctaat | taggcaaaaa | caggaggtaa agaaatagcc | 180 |
| aatcatctat | tgcctgacac | cacacgggga | gggacaatga | ttgggatata aacccaggaa | 240 |
| ttcgagctgg | caacggcaac | tcccttggg | tctcctctca | ttgtatggga gctctgtttt | 300 |
| cactctatta | aatcttgcaa | ctgcacactc | ttctggtctg | tgtttgttat ggcttgagct | 360 |
| gagcttttgc | tggctgtcca | ccactgctgt | ttgctgccgt | cgcagacccc ttgctgactc | 420 |
| ccacccctgc | ggatctggca | gggtgtctgc | tgcgctcctg | atccagccag gcacccactg | 480 |
| ctgctcccaa | tcaggctaaa | ggcttgccat | tgttcctgca | tggctaagtg cccgggttcg | 540 |
| tgctaattga | gctgaacact | agtcgctggg | ttccacagtt | ctcttccgtg acccacagct | 600 |
| tctaatagag | ctataacact | cactgcatgg | cccaacattc | cattccttgg aatctgtgag | 660 |
| gccaagaacc | cccggtcaga | gaacaagaag | cttgccacca | tcttggaagc agcccgccac | 720 |
| cattttggga | gctctaagaa | caaggacccc | ccagtaacat | tttggtgacc acgaagggac | 780 |
| ctccaaagca | gtgagtaata | ttgaaccact | tccgcttgct | attctgtcct aaccttcctt | 840 |
| agaattggag | gaaaataccg | ggcacctgtc | ggccagttaa | gaacgattag cgtggccgcc | 900 |
| agacttaaga | ctctggtgtg | aggctgtctg | ggaaagggct | ttctaacaac ccccaaccct | 960 |
| tccgggttgg | gagctttggt | ctgcctggaa | ccagcttcca | ctttcaattt tcctggggaa | 1020 |
| tccaagggct | gactagaggc | agaaagctgt | catcccgaac | tcctggcatt agacagttga | 1080 |
| gatcgtggcg | cagccagaag | tctctactca | acagtcaccc | atgcgtgcac ccctaccttt | 1140 |
| ccttctaacc | catacctccc | gggtcccaac | catgactttc | ttgaaagtgt agcccctaaa | 1200 |
| ttctctttac | ctctaaatct | acttcttctc | atccctgctt | cctaggtact aatggttcag | 1260 |
| actttcattt | cctctagcaa | gttctatctc | cagagggatc | taaggaaggg atctatgctg | 1320 |
| tgtccttagg | cccctaggct | atgaacccag | agagtcttct | ccctgttatc tctccccatt | 1380 |
| taggcataca | gctctcaaca | tggacagtta | tgtgggaccc | attccctacc acccttgcca | 1440 |
| gggcccaag | ttttcaaagg | gctagaagaa | aaaagagaga | aagagagaga gaggcagagg | 1500 |
| ggagagaaag | agagagagac | aaagagggag | tcaaagagag | atagaaagag aaagatagaa | 1560 |
| ctagtaaaga | aaaaaagtat | gcccccattcc | tttaaaagcc | agggtaaatt taaaacctat | 1620 |
| aattgataat | tgaaggtctt | ctccatgacc | ctataacact | ccaataccac cttgttttca | 1680 |
| gtgtaaacaa | gggtgtagcc | cgaaaacact | gagaccactg | acaacccata gccttcctat | 1740 |
| caaaaatcct | taacccagga | acccatggat | ggcccaaatg | cattcaatct gtagcagcaa | 1800 |
| ctgctttgct | aacagaagaa | agtagaaaag | taacttttag | agaaaacctc attgtgagca | 1860 |
| cacctcacca | gttcagaatt | attctaagtc | aaaaaagcaa | aaaggtagct tactaactca | 1920 |

```
aaaatcttaa agtatggggt tattctgtta gaaaaaggtg atttaacatt aaccactgaa      1980 aattcccttta acccagcagg tttcctaatg ggatttaaat cttcattacc atacaaaggt     2040
ccgaccagac ccagcaggaa ctcccttag gacaggatga tagatggttc ctcctgggtg      2100
attgaggggg tgaaaaacca caatgggtgt tcagtaattg atagggagac tcttgtggaa     2160
ggagagttag gaaaattgcc taataattgg tctgctcaaa tgtgcgagct gtttgcactc    2220
agccaagcct taaagtactt acagaatcaa aaagactcta tctcaatcct gactcaaaat    2280
gttacctaca ccatctctga catgaatttg cataagaact gttgtttatg ggaatgcatc    2340
ttgatggggc agctgggttg ttatgaaata ctcaggaacc cagcccaggt ctagaattca    2400
cctctgagcg caaaggcaat gttggccatg ctggtaaagg accactagaa tccaggagcc    2460 tggaccccctt tctttgtggt caagaaaggc gggaaaacag gtgcaggact gctacatcag   2520
agagcataac aaatccgata agcagagttc catgagtggt taagcaccct ggaaaggaac    2580
tcacctctga gtgcaaaggc aatgttaggc acaccagtaa aggaccacta gaatccagca    2640
gcccagaccc ctttctttgt gatcaagaaa ggcgggaaaa ggggtgcagg actgctacat    2700
cagtgagcgt aactaatctg ataagcagaa gtccatgggt ggttacgcac cctggaaagg    2760
aataagcatt aggaccacag aggacactct aagactaatg ctcattggaa aatgactagg    2820
ggtgctggca tccctatgtt tttttttcag atgggaaaca ttcccccaa ggcaaaacg      2880 cccataagat atattctgga gaattcggcc cagagtgtat gtatcttttt tccctgtcag    2940
acttgaagca aacctaggta aattatcaga tagccctgat ggctatattg atgctttaca   3000
agggttagga caatcctttg atctaacatg gagagatata ctgttactgc tagatcagac    3060
actaatccca aatgaaagaa gtgccaccat aactgcagcc agagagtttg atgatctctg   3120
gtatctcagt caggtcaatg ataggatgac aacagaagaa agaaaacaat tccccacagg    3180
ccagcaggca gttcccagcg tagaccttca ttgggacaca gaatcagaac atggagattg    3240
gtgccgcaga catttactaa cttgcgcgct agaagcacta aggaaaacta ggaagaagcc    3300
tatgaattat tcaatgatgt ccactataac acagggaaag gaagaaaatc ctactgcctt    3360
tctgagagag ctaagggagg cattgagaaa gcatacctct ctgtcacctg actctattga   3420
aggccaacta atcttaaagg ataagttttc cactcagtca gctgcagaca ttagaaaaaa    3480
acttcaaaag tctgcgttag gccgggagca aaacttagaa accctattga acttggcaac    3540
ctcagttttt tatgatagag atcaggagga tcaggtggaa tggacaaatg agatttaaa    3600 aaaaggccac cactttagtc atggccctca ggcaagcaga cttggacac tctggaaaag    3660 ggaaaagctg ggcaaatcga atgcctaata agacttgctt ccagtgtggt ctacaaggac    3720
actttaaaaa agattgtcca aatagaaata agccacccc tcgtccatgc tccttatgtc     3780
aagggaatca ctggaaggcc tactgcccca ggggatgaag gtcctctgag tcagaagcca    3840
ctaaccagat gattcagccc caggactcag ggtgcccagg gcaagcgcca gcctatgcca   3900
tcaccctcac agagccctgg gtatgcttga ccattgaggg tcaggaggtt aactatctcc    3960
tggacactgg cgtggccttc tcagtcttac tctcctgtcc cggacaactg tcctccagat    4020
ctgtcactat ccgagggttt ctacgacagc cagccactag atacttctcc cagccactaa    4080
gttgtgactg gggaactcta ctcttttcac atgtttttct aattatgcct gaaagcccca    4140
ctcctttgtt agggaaagac attctagcaa aagcaggggc cattatacac ctgaacatag    4200
gagaaggaac acctgtttgt tgtccccctgc ttgaagaagg aattaatcct gaagtctgga    4260
caacagaagg acaatacaga tgagcaacaa atgcctgtcc tgttcaagtt aaactaaagg    4320
```

```
attatgcctc ctttccctac caaaggcagt acccccttag acccgaggcc aacaaggac    4380 tccaaaagat tgttaaggac ctaaaagctc aaagcctagc aaaaccatgc agtagcccct    4440
gcaatactcc aattttagga gtacagaaaa ccaacagaca gtggaggtta gtgcaagatc    4500
tcaggattat caatgaggct gttgttccta acccttatac tctgctttcc caaataccag    4560
aagaagcaga gtggtttaca gtcctggacc ttaaggatgg cttttctgc atccctgtac    4620 atcctgactc tcaattcttg tttgcctttg gagatccttc gaacccaatg tctcaactca    4680
gcttgactgt tttaccccaa gggttcaggg atagccccca tctagttggc caagcattag    4740
ccgagccagt tctcctacct ggacactctt gtcctctggt acatggatga tttattttta    4800
gctgcccgtt cagaaacctt gtgccatcaa gccacccaag tgctcttaaa tttcctcgcc    4860
acctgtggct acaaggtttc caaaccaaag gctcagctct gctcacagca ggttaaatac    4920
ttagggctaa aattatccaa aggcaccagg gccctcagtg aggaatgtat ccagcctgta    4980
ttggcttatc ctcatcccaa aaccctaaag caactaagag ggttccttgg cataacaggt    5040
ttctgccaaa tgtggattcc caggtacggt gaaatagcca ggccattata taccctaatt    5100
aaggaaactc agaaagccaa cacccattta ttaagatgga cacctgaagc agaagcagct    5160
ttccaggccc taagaaggc cctaacccaa gccccagtgt taagcttgcc aacggggaag    5220
acttttcttt atatgtcaca gaaaaaacag gaatagctct aggagtcctt agacaggtcc    5280
aagggatgag cttgcaacct gtggcatacc tgagtaagga aattgatgta gttgcaaagg    5340
gttgacctca ttgttacag gtagtggcgg cagtagcagt cttagtatct gaagcagtta    5400
aaataataca gggaagagat cttactgtgt ggacatctca tgatgtaaac ggcgtactca    5460
cttctaaagg agacttgtgg ctgtcagaca accgtttact taaatatcag gctctattac    5520
ttgaagggcc agtgctgcga ctgcccactt gttcaactct taacccagcc acatttcttt    5580
cagacaatga agaaaagata gaacataact gtcaacaggt gattgctcaa acctacggcg    5640
ctcgagggga ccttctagag gttcccttga ctgatcccaa cctcaacttg tatactgatg    5700
gaagctcctt tgtagaaaaa ggactttgaa aggtggggta tgcagtggtc agtgataatg    5760
gaatacttga aagtaattcc ttcactccag gaactagtgc tcagctggca gaactaatag    5820
ccctcactca ggcactagaa ttaggagaag gaaaagggt aaatatatat gcagactcta    5880
agtatgctta cccagtcctc cacgcccaca cagcaatatg gagagatagg aaattcctaa    5940
cttctgaggg aacaccgatc aaacatcagg aagccattag gagattatta ttggctgtac    6000
agaaacctaa agaggtggca gtcttacact gctggggtca tcagaaagga aaggaaaagg    6060
aaatagaaag gaaccaccaa gtggatattg aagccaaaag agccacaagg caggccctcc    6120
attagaaatg cttatagaag gatccctagt atggggtaat cccctccggg aaaccaagcc    6180
ccagtactca gcaggagaaa tagacacgag gacatagttt cctcccctca ggatggctag    6240
ccaccgaaaa agggaaaata cttttgcctg cagctaatca atggaaatta cttaaaaccc    6300
ttcaccaaac ctttcacttg ggcatggata gcatctatca gatggccaat ttattattta    6360
ctggaccagg ccttttcaaa actatcaagc agatagtcag ggcctgtgaa atgtgccaaa    6420
gaaataatcc cctgcacttc aagccataca tttcaatccc tgtatcttta acctcctgtt    6480
gtttgtctct tccagactca agctgtaaa actgcaaatg gttcctcata tggagcccca    6540
gatgcagtcc atgactaaga tctaccacag agccctagac cggcctgtta gcccatgctc    6600
cgatgttgat gacatcaaag gcacaccttc cgaggaaatc tcaactgcac gaccccctact  6660
```

| | |
|---|---|
| aagccccaat tcagcaggaa gcagttaaga gcagtcgttg gctaacatcc ccaatagtat | 6720 |
| gtgggttttc ctgttgagag gggggactga gagacaggac tagctggatt tcctaggcca | 6780 |
| actaagaatc cctaagccta gttgggaagg tgaccgcatc cacctttaaa cacgggctt | 6840 |
| gcaacttagc tcacacccga ccaatcaggt agtaaagaga gctcactaaa atgctaatta | 6900 |
| ggcaaaaaca agaggtaaag aaatagccaa tcatctatcg cctgagagca cagtggggag | 6960 |
| ggacaatgat cgggatataa acccaggcat tcgggccggc aacggcaacc cccattgcgt | 7020 |
| cccctcccat tgtatgggag ctctgttttc attctattaa atcttgcaac tgcacactct | 7080 |
| tctggtctat gtttgttatg gctcgagctg agctttcgct cgctgtccac cactgctgtt | 7140 |
| tgccgccatc gcagacccac cactgacttc cacctctgca gatctggcag ggtgtccgct | 7200 |
| gtgctcctga cccagcgagc cacccattgc tgctcccaat caggctaaag gcttgccatt | 7260 |
| gttcctgcat ggctaagagc ccagggttcg tcctaatcga gctgaacgct agtagctggg | 7320 |
| ttccacagtt ctcttccgtg acccacggct cctaatagag ctataacact caccacatgg | 7380 |
| cccaaggttc cattcattgg aatccgtgag gccaagaacc cccggtcaga gaacaagaag | 7440 |
| cttgccacca tcttggaagc tctaaaaaca gagacacccc agtaaca | 7487 |

<210> SEQ ID NO 2
<211> LENGTH: 7774
<212> TYPE: DNA
<213> ORGANISM: Homo sapiens

<400> SEQUENCE: 2

| | |
|---|---|
| tgagacacag gactagctgg atttcctagg ccgactaaga atccctaagc ctagctggga | 60 |
| aggtgaccac atccaccttt aaacacgggg tttacaactt agctcacacc cagccaatca | 120 |
| gagagctcac taaaatgcta attaggcaaa aacaggaggt aaagaaatag ccaatcatct | 180 |
| attgcctgag agcacagcgg gagggacaag gattgggata taaacccagg cattcgagct | 240 |
| ggcaacggca acccccttg ggtctcctcc ctttgcatag gagctctgtt ttcactctat | 300 |
| taagtcttgc aactgcactc ttctggtccg tgtttcttac cgcttgagct gagcttccc | 360 |
| tcactgtcca ccactgctgt tttgccaccg tcacaggccc accgctgact tccattcttc | 420 |
| tggatctagc aggctgtcca ctgtgctcct gatccagcga ggcgcccatt gccgctcccg | 480 |
| attgggctaa aggcttgcca ttgttcctgc atggctacgt gcctgggttc atcctaatca | 540 |
| agccgaacac tagtcactgg gttccacggt tctcttccat gacccacgac ttctaataga | 600 |
| actataacac tcacctcatg gcccaagatt ccattccttg gaatccatga ggccaagaac | 660 |
| cccaggtcag agaacacgag gcttgccacc atcttggaag tggcccacc accatcttgg | 720 |
| gagctctggg agcaaggacc cccggtaaca ttttggcgac cacaaaggga catccaaagt | 780 |
| ggtgagtaat attggaccac tttcacttgc tattctgttc tatccttcct tagaactgga | 840 |
| ggaaaatacc aggcacaggc acctgtcagc cagttaaaaa caattagcgt cgccgccaca | 900 |
| cttaagactc aggtgtgagg ctatctgggg aaagactttc taacaacccc caacccatct | 960 |
| agtggggatg ttggtctgcc tggagacagc ttccactttc aattttcttg gggaagccga | 1020 |
| gggctcacta gaggcagaca gctgttgtcc caaactccgg gcagtagccg gttgagatca | 1080 |
| tggtgcagcc aggagtctct actcagcagt cgccgatgca tgtgcccta ccttcccttc | 1140 |
| tgacccatac atcctgagtc ccgactgtga ctttcttgaa agtgtagccc caaaattctc | 1200 |
| cttacctctg aatctacttc ctctgatccc tgcctcctgg gtactaatga ttcagacttt | 1260 |
| catttcctct agcaagttgt gtctccaaag ggatctaagg aggctctacg ctgcatcctt | 1320 |

```
aggcacctag gctataaccc aaggagtctt atccctggtg tccctcccga tttgggtata    1380
caactctcaa catgggcagt tatgtaggac ccattcccca ccacacttgc cagggcccca    1440
agtttgtaat ggctaagaga gagacacaga gagagagaga gagatggaga gagagacaag    1500
gagggagtca aagagaaaaa gaaagaaaaa gaaatagtag aaaaaaaagt gtgccctatt    1560
cctttaaaag ccagggtaaa tttaaaacct gtaattgata attgaaggtc ttctccgtga    1620
ccctgtaaca ctccaatgcc attttgttgt cagtgtaaat aagggcatag cccaaaagca    1680
ctgaggtcac tgacaacccg tagctttccc atcaaaaatc cttaacccag taatccgcgg    1740
atgggccaaa tgcattcagt cggtagcagc aaccgctttg ctaaaagtag aaaagtaact    1800
tttagaggaa acctcattgt gagcgcacac ctcaccagtt cagaattatt ctaagtcaaa    1860
aaaaaaaaaa gcaaaaaggt aacttactaa ctcaaaaatc ttaaagtata ggtctatcat    1920
attagaaaag ggtaatgtaa ctccaaccac tgataattcc cttaacccag cagatttcct    1980 aacagggggat ttaaaactta attaccatac aaaggtccca ccagacctag gaggaactcc    2040
cttcaggaca ggacgataaa cggttcctcc caggtgattg aggaaaaaaa ccacaatggg    2100
tattcagtaa ttgatacaga gactcatgtg gaagcagtta gaaaaattgc ctaataattg    2160
gtctcctcaa acgtgtaagc tgtttgcact cagccaagcc ttaaagtact tacagaatca    2220
aaaagactct gaatcctgac tcaaaaggtt tgctacaccc tctgtgaaac aaatttgcat    2280
aagaactgtt gtttatggga aggcatcttg atggggcagc tgggttgtta tgaaatactc    2340
aggaccccag cccggctcta ggactcaccc ctgagcgcaa aaggcaatgt tgggcacgct    2400
ggtaaaggac cactagaatc cagcagcccg gaccccttc tttgtggtca agagaggcgg    2460
gaaaacaggt gcaggactgc tacatcagtg agcataacta atccagtaag cagaggtcca    2520
tgggtggtta tgcaccctgg aaaagaatac gcattaggcc cttagaggat gctctaggac    2580
taatgctcat cggaaaatga ctaggggtgc tgacatccct atgttctttt ttcagatggg    2640
aaacgttcct cccaccccaa ggcaaaaaac acccctaaga tgtatttttgg agaattagga    2700 ccaatttgac cctcagacac taagaaagaa atgacttaca ttcttctgca gtaccatgat    2760
atcctcttca aggggagaa acctggcctc ctgagagaag tataaattat aacaccatct    2820
tacagtgaga cctcttctgt agaaaggagg gcaaatggag tgaagtgcaa actttccttt    2880
cattaagaga caactcgcaa ttatgtaaaa agtgtgattt atgccctaca gaaagccctc    2940
agtctacctc cctatcccag ggtcccccg attccttttcc caactaataa ggacccccct    3000
tttacccaaa tggtccaaag gagatagatg aagggataaa caatgaacca aacagtgcca    3060
atattccctg attatgcccc ctccaggcag tgggaggagg agaattcggc ccagccagag    3120
tgcatgtacc tttttttttc tctcagactt aaagcaaatt aaaatagacc taggtaaatt    3180
ctcagataac cctgatggct atattgatgt tttacaaggg ttaggacaat cctttgctct    3240
gacatggaga gatataatgt tactgctaaa tcagacacta acccccaaatg agagaagtgt    3300 caccatagct gcagcccaag agtttggcaa tctctggtat ctcagtcagg tcaatgatag    3360
gatgacaaca gaggaaaggg aatgattccc cacaggccag caggcagttc tcagtgtaga    3420
ccctcactgg gacacagaat aagaacatgg agatcggtgc cgcagatatt tgctaacttg    3480
cgtgctagga ctaaggaaaa ctaggaagaa gcctatgaat tattcagtga tgtccactat    3540
aacacaggga aaggaagaaa atcatactgc ctttccggaa atactaaggg aggcattgag    3600
gaagcatacc tctctgtcac ctgactgtat tgaagtccaa ctaatcttaa aggatatgtt    3660
```

-continued

```
tatcactcag tcagctgcag acattagaaa aaacttcaaa agtccacctt aggcccagag    3720
caaaacttag aaaccctatt gaacttgtta acctcagttt tttataatag agatcaggag    3780
gagcaggcgg aacaggacaa acaggattaa aaaaagacca ccgctttagt catggccctc    3840
aggcaagtgg actttggaag ctctggaaaa gggaaaagct gggcaaattg aatgcctaat    3900
agggcttgct tccagtgtgg tctacaagga cacttaaaaa aagattgtcc aagtagaaat    3960
aagctgcccc ttcgtccatg cctcttatgt caagggaatc actggaaggc ccattgcccc    4020
aggggaggaa ggtcctctga gtcagaagcc actaaccaga tgatccagca gcaggactaa    4080
gggtgcccag ggcaagcccc agcccatgcc atcaccctca cagagcccg ggtatgcttg    4140 accattgagg gccaggaggt taactgtctc ctgaacactg gcacagcctt ctcagtctta    4200
ctttcctgtc ccggacaact gtcctccaga tctgtcacta tctgagcggt cctaggacag    4260
ccagtcacta gatatttctc ccagccacta agttgtgact ggggaacttt actcttttca    4320
catgcttttc taattatgcc tgaaagcccc actcctttgt tagggagaga cattctagca    4380
aaagcagggg ccattataca tctgaacata ggagaaggaa cacccgtttg ttgtcacctg    4440
cttgaggaag gaattaatgc tgaagtctgg gcaacagaag gacaatatgg atgagcaaag    4500 aatgccatc ctgttcaagt taaattaaag gattccgcct cctttcccta ccaaaggcaa    4560
taccccctta gacccgaggc ccaacaagga ctccaaaaga ttgttaagga cctaaaagcc    4620
caaggcctag taaaaccatg caatagcccc tgccatactc caattttagg agtaaggaaa    4680
cccaacggac agtggaggtt agtgcaagaa ctcaggatta tcaatgaggc tgttgttcct    4740
ctatacccag ctgtacctaa cccttataca gtgctttccc aaataccaga ggaagcagag    4800
tggtttacag tcctggacct taaggatgcc tttttctgca tccctgtacg tcctgactct    4860
caattcttgt ttgcctttga agatcctttg aacccaacgt ctcaactcac ctggactgtt    4920
ttaccccaag ggttcaagga tagccccat ctatttggcc aggcattagc ccaagacttg    4980
agccaattct cataccctgga cactcttatc cttcggtatg gggatgattt aattttagct    5040
acccattcag aaacgttgtg ccatcaagcc acccaagtgc tcttaaattt cctcgctacc    5100
tgtggctaca ggtttccaaa cgaaaggctc agctctgctc acagcaggtt aaatacttag    5160
ggctaaaatt atccaaaggc accagggccc tcagtgagga acgtatccag cctatactgg    5220
cttattctca tcccaaaacc ctaaagcaac taagagcatt ccttggcata acaggctgct    5280
gctgaatatg gattcccagg tacagtgaaa tagccaggcc attatacaca ctaattaagg    5340
aaactcagaa agccaatacc catttagtaa gatggcacacc ttaagcagaa gcggctttcc    5400
aggccttaaa gaaggcccta acccaagccc cagtggtaag cttgccaaca gggcaagact    5460
tttcttatta tgtcacagaa gaaacaggaa tagctctagg agtccttaca caggtctgag    5520
ggatgagctt gcaacccatg gcatacctga gtaaggaaac tgatgtagtg gcaaagggtt    5580
ggcctcattg tttacgggta gtggcagcag tagcagtctt agtatctgaa gtagttaaaa    5640
taatacaggg aagagatctt actgtgtgaa catctcatga tgtgaatggc atagtcactg    5700
ctaaaggaga cttgtggctg tcagacaact gtttacttaa ataccaggct ctattacttg    5760
aagggccagt gctgcgactg tgcacttgtg caactcttaa cccagacaca tttcttccag    5820
acaatgaaga aaagatagaa cataactgcc aacaagtaat tgctcaaacc tatgccactc    5880 gagggggacct tttagaggtt cccttgactg atcccaacct caacttgtat actgatggaa    5940
gttcctctgt agaaaaagga ctttgaaaag tggggtatgc agtggtcagt gataatggaa    6000
tacttgaaag taatccctc actccaggaa ctagtgctca gctggcagaa ctaatagccc    6060
```

-continued

```
tcactcgggc actagaatta ggagaagaga aaagggtaaa tatatacaga ctctaagtat      6120
gcttacctag tcctccatgc ccatgcagca atatggagag aaagggaatt cctaatttcc      6180
aagggaacac ctatccaaca tcaggaagcc attaggagat tactattggc tgtacagaaa      6240
cataaagagg tggcaatctt acactgccgg tgtcaccaga aaggaaagga aagggaaata      6300
gaaaggaacc accaagcgga tattgaagcc aaaagagccg caaggcagga ccctccatta      6360
gaaatgctta tagaaggacc cctagtatgg ggtaatcccc tccaggaaac caagcccag       6420 tactcagaag aagaaataga atgaggaacc tcacaagcac atagtttcct cccctcagga      6480
tggctagcca ctgaagaagg aaaaatactt ttgcctgcag ctaaccaatg gaaattactt      6540 aaaaccttc accaaacatt tcccttaggc attgatagca cccatcagat ggccaaatta       6600
ttatttactg gaccaggcct tttcaaaact atcaagcaga tagtcagggc ctgtaaagtg      6660
tgccaaacaa gtaatcccct gcactgcagg ccatacattt caatccctgt atctttaacc     6720
tccttgttaa gtttgtctct tccagaatca aagctgtaaa actacaaata gttcttcaaa     6780
tggagcccca gatgtagtcc atgactaaga tctaccgcgg accctggac aagcctgcta      6840 gcccatgctc tgatgttaat gacatggaag gcacccctcc cgaggaaatc gcaactgcac     6900 aaccccctatt acaccccaat tcagcaggaa gcagttagag cattcatcag ccaacctccc    6960
caacagcact tgggttttcc tattgagagg gggtactgag agacaggact agctggatgt     7020
cctaggctga ctaagaatcc ctaagcctag ctgggaaggt gaccacatcc acctttaaat     7080
acggggcttg caacctagct cacacccaac agatcagaga gctcgttaaa atgctaatta    7140
ggcaaaaaca ggaggtaaag aaatagccaa tcatctattg cctgagagca cagcaggagg     7200
gacaaggatt gggatataat cccaggcatt cgagctggca acagcaaccc cctttgggtc     7260
ccctcccttt gtatgggagc tgttttcact ctatttcact ctattaaatc ttgcaactgc    7320
actcttctgg tgcatgtttg ttactgcttg agctgaactt tcactcgcca tctaccactg     7380
ctgttttgcc gccgtcgcag acccactgct gacttccatt cttctggatc cagcagggtg    7440
tccactgtgc tcctgatcca gtgaggcacc cattgccgct cccgatctgg ctaaaggctt     7500
gccattgttc ctgcatcgct aagtgcctgg gttcgtccta atcaagctga acactagtca    7560
ctgggttcca cagttctctt ccatgaccca cgacttctaa tagagctata acactcacct     7620 tatgcccaa gattccattc cttggaatcc atgaggccaa aaaccccagg tcagagaaca     7680
tgagacttgc caccatgttg aagtggcctg ctgccatttt ggaagtggcc caccaccatc     7740
ttgggagctc tgggagcaag gaccctggt aaca                                  7774
```

<210> SEQ ID NO 3
<211> LENGTH: 5470
<212> TYPE: DNA
<213> ORGANISM: Homo sapiens

<400> SEQUENCE: 3

```
tgagagacag ctggatttcc taggccgact aagaatccct aagcctagct gggaaggtga       60
ccgcatccac ctttaaacac agggcttgca acttagctca cacccaacca atcagagagc      120
tcactaaaat gctaattagg caaaacagg aggtaaagaa atagcaagtc atctattgcc       180
tgagagcaca gtgggaggga caaggaccag gatataaacc caggcatttg agccagcaac      240 ggcaaccctcc tttgagtccc ctccctttgt ataggagctc tgttttcact gtgtttcact    300
ctattaaatc ttgcaattgc actcttctgg tccatatttg tcacggcttg agctgagctt    360
```

```
tcacttgccg tccaccacta ctgtttgctg ctgtcacaga cccgccgctg actcccatcc      420
cgctgctgac tcccatccct ccggatccgg cagggtgtcc gctgtgctcc tgatccagca      480
agactcccat tgccactccc gatagtgcta aaggcttgcc attgttcctg catggctaag      540
tgcctgggtt cgtcctaatc cagctgaaca ctagtcactg ggttccacgg ttctcttcca      600
tgacccgcgg cttctaatag agctataaca ctcaccacat ggcccaatat tccattcctt      660
ggaatccgtg aggccaagaa ccccaggtca gagaacacga ggcttgccac catcttggaa      720
gcagcctgcc accatcttgg aagtggctca ccaccgtctt gggagttctg tgaacaagga      780
cccctggtaa cattttggcg accacgaagg gacatccaaa gctgtgagta atattggacc      840
actttcgctt gctattctgt tctatcctta gaactggagg aaaatactgg gcacctgtcg      900
ccagttaaaa atgattagca tggccgccgg acttaagact caggtgtgag gctatctggg      960
aaagggcttt ctaacaaccc ccaagccttc tgttgggaac tttggtctgc ctggagccag     1020
cttccacttt caattttctt ggggaagcca agggctgact ggaggcagaa agctgttgtc     1080
ccgaactccc ggcagtagcc ggttgagatc atggcgcagc cagaagtctc tactcggcag     1140
tcgcccatgc gtgcgccctt acctttcctt ctgaattata cctccggggt cccgactccg     1200
actttcttga gagtttagcc ccaaaattct ccttacctct gaatctactt cctttgatcc     1260
ctgcctcctg cctcctaggt actaatagtt cagactttca tttcctctag caagttgtgt     1320
ctccaaaggg atctaaggag gctctatgct gtgtccttag gcacctaggc tataacccag     1380
ggagtcttat ccctggtatc cctcccgatt taggtataca gctcttgaca tgggcagtta     1440
tgtgggacct gttccccacc acccttgtga gggcccaag tttgtaatgg ctaagaaaga     1500
gagacggaga gagagagaga cggagaaaga gacaagagg gagtcaaaga gaaaagaaa     1560 gaaaagata gaaatagtta aaaaaaaaa aaagtgtgcc ctattccttt aaaagccagg     1620
gtaaatttaa aacctgtaat tgataattgc cactttgttg tcagtgtaaa taagggcgta     1680
gcaaatcctt aacccagtaa cccgcggata ggccaaatgc attcagtcgg tagcggcaac     1740
agctttgcta aaagtagaaa agtaactttt agaggaaacc tcattgtgag cacacctcac     1800
cagttcagag ttattctaag taaaaaaaaa aaaaaaaaaa aaagcaaaaa ggtagcttac     1860
taactcaata atcttaaagt atggggctac tatgctagaa aagggtaatg taactccaac     1920
cactgataac tcccttaacc cagcagattt cctaacaggg gatttaaatc ttaattacca     1980
cacgaaggtc cgaccagacc taggaggaac tcccttcagc acaggacgat agatggttcc     2040
tcccaggtga ctgaggaaaa aactacaatg ggtattcagt aattggtatg gagactcttg     2100
tggaagcaga gttaaaaatt tgcctaataa ttggtctcct caaatgtgcg agctgtttgc     2160
actcagccaa gccttaaagt acttacgaaa tcaaaagact atctcaatcc tgactcaaaa     2220
ggttagctac acagtctctg aaatgaattt gcagaagaac tgttgtttat gggaatgcat     2280
cttgatgggg cagctgggtt gttatgaaat actcaggaac ccagcccagc tctaggactc     2340
accgctgagc gcaaaggcaa tgttgggcac gctggtaaag gaccactaga atccagcagc     2400
ccaggcccct ttctttgtgg tcaagaaagg caggaaaagg agtgcagaac tgctacattg     2460
gtgagcgtaa ctaatccaat aagcagaggt ccatgagtgg ttatgcacgc tggaaaagaa     2520
taagcattag gcccttagag gatgctctag gactaatgct catcggaaaa tgactagggg     2580
tgctggcatc cttatgttct ttcttcagat gggaacgtt ccccccaagg caaaagcgcc     2640
cctaagatgt attctggaga attagaacca atttgaccct cagatgtcaa gaaagaaacg     2700
acttatattc ttctgcagta ctgcctggcc acgatatcct cttcaagggg gagaaacctg     2760
```

```
gcctcctgag ggaagtacaa attataacac catcttacag ctagacctct tttgtagaaa    2820
agaaggcaaa tggagtgaag tgccatatgt gcaaactttc ttttcattaa gagacaactc    2880
acaattatgt aaaagtgtg gtttatgtct tacaggaagc cctcagagtc tacctcccta    2940
tcccagcatt cccccgactc cttccccaac taataagcac cacccttgaa cccaaacagt    3000
ccaaaaggag atagacaaac aggtaaacaa tgaaccaaag agtgtcagta ttccccgatt    3060 atgcccttc caagcagtgg gaggaggaga attcggccca gccagagtgc atgtaccttt    3120
ttctctctca gacttaacgc aaattaaaat agacttaggt aaattctcag ataaccctga    3180
tggctacatt gatgttttac aagggttagg gcaatccttt gatctgacat ggagagatat    3240
aatgttactg ctaaatcaga cactaacccc aaatgagaga agtgccgccg taactgcagc    3300
ccgagagttt ggtgatctct ggtatctcag tcaggtcaat gataggatga aacagagaa     3360 aagagaacga ttccccacag gccagcaggc agtttccagt gtagaccctc attaggacac    3420
agaatcagaa catggagatt ggtgccacag atatttgcta acttgagtgc tagaaggact    3480
aaggaaaact aggaagaagc ctatgaatta ttcagtgatg tccactataa cacaaggaaa    3540
ggaagaaaat cctactgcct ttctggagag agtaagggag gcattaagga agcatacctc    3600
cctgtcacct gactctattg aaggccaact aatcttaaag gataagtttg tcactcagtt    3660
agctgcagac attagaaaaa aacttcaaaa gtccgactta ggcctggagt acggctgagt    3720
gcccaatttg gcagcaggca agaccaacac tgagcccttc atatggcacc atgctttgtg    3780
gtgatcagcc aactacttga tggcaggttg attatattgg acatctttca tcagagaaat    3840
ggcagtggtt tgtccttcct ggaatagaca cttattctcg atatgggttt gtctatcctg    3900
caggcaatgc ttctgccagg agtaccatct gtggactcat ggaaagcctt atccaccatc    3960
atggcattcc acacagcatt gcctctaaac aaggcactta ttttatagct aaggaagtgt    4020
ggcagtgggc tcatgctcat ggaattcact gattgtatct tgttgcccat tatcttaaag    4080
cagctggatt gatagaacag tggaaaggcc atttgaaatc acaattacac caccaactag    4140
gtgacaatac tttgcagggc tcggcaaagt tctcttgaag gctgagtatg tcctgaatca    4200
gcatccaata tatggtactg tttccctcat agccagcatt cacaggccta agaatcaagg    4260
ggtagaagta gaagtggcac cactcaccat cactcctagt gacccactag caaaaatttt    4320
acttccagtt ccccccaacat tatgttctgc tggccttagt tccagaggga agaattctgc    4380
caccagtcga cacaagaatg ataccattaa actgaaagtt aaaattgcca cctggccact    4440
ttgggctcct cccacctcta agtcaacagg tcaagaaagg agttacagtg ttgacttggg    4500
tgattgacct ggactatcaa gatgaaatca ggttactact ccacagtgga ggtaaggaag    4560
aatatgtgtg gaatacagga gatcccttag gccgtctttt agtactacca tgccctgtga    4620
ttaaggtcag tggaaaacta caacaatcca atctaggcag gactacaaat ggcccagact    4680
cttcaggaat gaagggttgg gtgacttcac caggtaaaaa aataacagcc tgctgaggtg    4740
ctagctgaag gcaaagggaa tacagaatgg ttagtagaaa aaggtagtca tcaataccag    4800
ctatgaccac aagaccagtt gcagaaatga gacctgtaat tgtcatgtgg atttcctcct    4860
tacatgtttg tgcatgtata cacttctact aagaaaatac ctttatttat ttccttgct     4920 tttcccttat caagtgacat tattaacttc atatcagcag ttaagtgtta ttaactttat    4980
gtaatagcat ttcggttaat aattcacttc tggttgtatg aaggatagcc gtattaagtt    5040
aggtgtaatt atgacatcat tattgtcttt atttgaagat tatgtgtaat ttcaggagat    5100
```

```
gtgtatgggt tcaagttgac aagggatgga cttgtgatgg ctaatgttga gtgtcaactt      5160
gactgaggat gcaaagtatt gttcctgggt gtgtctgtga gggtgttgcc aaaggagatt      5220
aacatttgtg tcagtgaact gggagatgca gacccacccg caatctgggt gagcaccatg      5280
taatcagctg ccagagcagc tagaataaag caagcagaag aaggtggaag gagctgactt      5340
gctgagtctt ctagtattct tcgttcttct atgctggttg cttcctgccc ccaaacatca      5400
gtctgcaagt tcttctgctt ttggactctt ggacttacac cagtggtttg ccagggactc      5460
tcgggccttc                                                              5470

<210> SEQ ID NO 4
<211> LENGTH: 783
<212> TYPE: DNA
<213> ORGANISM: Homo sapiens

<400> SEQUENCE: 4
tgagagacag gactaactgg atttcctagg ccgactaaga atccctaagc ctagctggga        60
aggtgaccgc atccatcttt aaacacgggg cttgaaactt agctcacacc taaccagtca       120
gagagctcac taaaatgcta attaggcaaa aaacaggagg taaagaaata gccaatcatc       180
tattgcctga gagcacagcg ggagggacaa ggatcgggat ataaacccag gcattcgagc       240
cagcaatggc aacccccttt gggtccccct cccttgtatg ggagctctgt tttcactcta       300
tttcactcta ttaaatcttg caactgcact cttctggtcc atgtttgtta cggctcgagc       360
tgagctttgg ctcgccatcc accactgctg tttgccgccg tcgcacacct gctgctgact       420
cccatccctc cggatccagc agggtgtgtc cgctgtgctc ctgatccagc gaggtgccca       480
ttgccgctcc tgattggact aaaggcttgc cattgttcct gcacggctaa gtgcccgggt       540
tcgtcctaat ccagctgaac actagtcact gggttccacg gttctcttcc ttgacccacg       600
gcttctaata gagctataac actcaccgca tggcccaaga ttccattcct tggaatctgt       660
gaggccaaga accccaggtc agagaacacg aggcttgcca ccatcttgga agcggcctgc       720
caacatcttg gaagtggctc gccaccatct tgggagctct gtgagcaagg acccctggta       780
aca                                                                     783

<210> SEQ ID NO 5
<211> LENGTH: 7542
<212> TYPE: DNA
<213> ORGANISM: Homo sapiens

<400> SEQUENCE: 5
tgagagacag gactagctgg atttcctagg ccgactaaga atccctaagc ctagctggga        60
aggtgaccgc ttccaccttt aaacacgggg cttgcaactt agctcacacc cgaccaatca       120
gatagtaaag agagcacact aaaatgctaa ttaggcaaaa acaggaggta agaaatagc        180 caatcatcta ttgcctgaga gcaaagcggg agggacaatg atcgggatag aaacccaggc       240
attcaagccg gaatggctac cctctttggg tcccctccct tgtatggga gctctgtttt        300 cactctattc aatcttgcaa ctgcactctt ctggtccgtg tttgttacag cttgagctga       360
gctttcgctc gccttccacc actgctgtttt gccgccatcg cagacctgcc gtgctgactt      420
ccatccctct agatctggca gggtgtccgc tgtgctcttg atccagcgag gcgcccattg       480
ccgctcccga ttgggctaaa ggcttgcaat tgttcctgca cgctaagtgc ctgggttcat       540
cctcatcaag ctgggttcca cggttctctt catgacccgc agcttctaac agagctataa       600
aactctgtgc atggcccaag attccattcc ttggaatctg tgaggccaag aaccccaggt       660
```

```
cagagaacag gaggcttgcc accatcttgg aagtggctcg ccaccatctt aggagctctg    720
tgagcggaga ccccccccc ccggtaacat tttggcgacc acgaagggac ctccaaagcg    780
gtgagtaata ttggatcact ttcgcttgct attctgtcct atccttcttt agaattggag    840
gaaaatactg ggcacctgtc ggccagttaa aaacaattag cgtggctgcc cgacttaaga    900
ctcaggtgtg aggctatctg gggaagggct ttctaacaac ccccaaccct tctgggttgg    960
ggacgttggt ctgccccttc cactttcaat tttcttgggg aagccaaggg tcgactagag   1020
gcagaaagct gtcgtccgga actcctggca gtagccggtt gagatcatgg cgcagccaga   1080
agtctctact caacagtcgc ccatgcgtgc gctcctacct ttcctcctga cccatacctc   1140
ctgggtcccg acgatgactt tcttgaaagt gtagcccaa aattctgctt acctctgaat   1200
ctacttcccc tgatccctgg ctcctaggta ctaatggttc agtttcattt cctctagcaa   1260
gttgtatctc caagggatc taaggaagct ctacgctgcg tccttaggca tctaggctat   1320
aaacccagga agtcttgtcc ctggtgtccc tcccgattta ggcatacagc tctcgacatg   1380
ggcagttatg tgggacccgt tccccatcac ccttgtcaag gccccaagtt tgtaatggct   1440
aagaggagag agagagaaag agagagagac ggaggggaga gagagagaga gagatggagg   1500
ggagagagag agagagagac ggaggggaga gagagagaga gagagagacg gaggggagag   1560
agagagagac ggaggggaga gagagagaga tggaggagag aaagacaaag ggagtcaaag   1620
agaaaaagaa agagaaagac agaaatggta aaacaaacaa aaaacagcgt gccctattcc   1680
tttaaaagcc ggggtaaatt taaaacctat aattgataat tgaaggtctt ctccatgacc   1740
ctataatact ccaatactac cttgttgtca gtgtaaacaa gggcgtagcc tgaaaacact   1800
gagaccactg acaacctgca gctttcctat caaaaaatcc ttaacccagt aaccggcaga   1860
tgcattcaat ctgtagcagc aactgttttg ctaacagaag aaagtagaaa agtaacttt    1920 agaggaaacc tcattgtgag cacaccttac cagttcagaa ttattctaag tcaaaaaagc   1980
aaaaaggtag cttactaact caaaaatctt aaagtatggg gctattgtgt ttaaaaaaaa   2040
aaaaaggtaa tttaacacca accactgata attctcttaa cccagcaggt ttcctaacag   2100
gggatttaaa tcttaattac catacaaagg tctgaccaca cctaggagga actcccttca   2160
ggacaggact atagagggtt cctcccaggt gattgaggaa aaaccacag tgggtattca   2220 gtaattgata gggagactct tgtggaagca gagttagaaa aattgcctaa taatggtgt   2280 cctcaaaagt gtgagctgtt tgcactcagc caagccttaa agtacttaca gaatcgtaaa   2340
aactatctca atcctgactc aaaagtttac ttacaccctc tctgaaatga atttacataa   2400
gaactgcttt tttgggaatg catcttgatg gggcagctgg gtggttatga aatactcagg   2460
aaaccagccc agctctagga cacatccctg agcacaaagg caatgttggg cacgctggta   2520
aaggaccact agaatccagc agcctggact cctttctttg tggtcaagaa aggcaggaaa   2580
acaggtgcag gactgctaca tcagtgagca taactaatct gataagcaga gggccttggg   2640
tggttacaca ccctggaaag gaattcaact ctgagcgcaa aggcaatgtt gggcacattg   2700
gtaaaggacc actagaatcc agcagcccag gccccttttct ttatggtcaa gaaaggcggg   2760 aaaagggtg caggactgtt acctcggtga gcgtaactaa tccgataagc agaggtccat   2820
gggtgattac gcaccctgaa aagaataagc attaggccct taaggatgc tctaggacta   2880 atgctcattg gaaaatgact aggggtgctg gcatccctat gttcttttct cagacgggaa   2940
atgttctcca ccctccccaa ggcaaaaaca cccctaagat gtattctgga gaattgggac   3000
```

```
caatttgacc cccagacgct aagaaagaga tgacttatgt tcttctgcag taccacctgg    3060
ccacgatatc ctcttcaagg gggagaaacc tggcctcctg agggaagtat aaattataac    3120
accatcttac agctagacct cttctgtaga aaggagggca aatggagtga agtgccatat    3180
gtgcaaactt tcttttcatt aagagacaac ttgcaattat gtaagaagtg tgatttatgc    3240
cctacaggaa gccctcagag tctacctccc taccccagca tcccctgac tccttctcca     3300
actaataagg aaccccttc aacccaaacg gtccaaaagg agatagacaa aggggtaaac     3360
aatgaaccaa agcgtgccaa tgttccctga ttatgccccc tctaagcagt gggaggagga    3420
gaatttggcc cagccagtgt gcatgtgcct ttttctctct cagacttaaa gcaaattaaa    3480
atagacctag gtaaattctc agataaccct gatggctata ttgatgtttt ataagggtta   3540
ggataatcct ttgatctgac atggagagat ataatgttac tgctagatca gacactaacc   3600
ccaaatgaga caagtgccgc cataactgca gcctgagagt ttggcgatct ctggtatctc   3660
actcgggtca atgataggag acaacagag gaaagagaat gattcccac agaccagcag     3720
gcagttccca gtgtagaccc tcactgggac acagaatcag aacatggaca ttggtgctgc   3780
agacatttgc taacttacat gctagaagga ctaaggaaaa ctaggaagaa gcctacgaat   3840
tattcaatga tgtccactat aacacaggga aaggaagaaa atcctactgc ctttctggag   3900
cgactaaggg aggcattgag gaagcatact tccctgtcac ctgactctat tgaaggccaa   3960
ctaatcttaa aggataagtt tatcactcag tcagctgaag acattaggaa aaaacttcaa   4020
aagtctgcct taggcccaga gcaaaactta gaaaccccat tgaacttggc aacctcggtt    4080
ttttataata gagatcagga ggagcaggcg gaacaggaca aacggggtaa aaaaaaggcc    4140
accgctttag ttatggccct caggcaagtg gactttggag gctctggaaa agggaaaagc    4200
tgggcaaatc gaatgcctac tagggcttgc ttccagagtg gtctacaagg cactttgaa    4260
aaagattgtc caagtagaaa taagtcgccc cttcgtccat gcccttata tcaagggaat    4320
cactggaagg cccactatcc caggggacaa atgtcctctg agtcagaagc cactaaccag    4380
atgatccagc agcaggactg agggtgccca gggcaagcac tagcccatgc cgtcaccctc    4440
acagagcccc aggtatgctt gaccattgag ggccaggagg ttaactgtct cctggacact    4500
agcacggcct tctcagtctt actctccttt cccggacaac tgtcctccag atctgtcact    4560
atccgagggt tcctaggaca gtcagtcact agatacttat cccagtcact aagttgtgac    4620
tggtgaactt tactctttc acatgctttt ctaattatcc ctgaaagcac cactcccttg     4680
ttagggcgag acattctagc aaaagcaggg gccattatac acctgaacat aggagaagga    4740
acacctgttt gttgtcccct gcttgaggaa ggaattaatc ccgaagtctg ggcaacagaa    4800
ggacaatacg gacgagcaaa gaatgcctgt gctgttcaag ttaaactaaa ggattccgcc    4860
tcctttccct accaaaggca gtaccccctt agacctgagg cccaacaagg actccaaaag    4920
attgttaagg acctaaaagc ccatggccta gtaaaaccat gcaatagccc ctgcaatact    4980
ccaatttag gagtacagaa acccaacaga cagtggaggt tagtgcaaga tctcaggatt    5040
atcattgagg ctgttgttcc tgtatagcca gctgtaccta acccttatac tctgctttcc    5100
caaataccac aggaagcaga gggtttaca gtccggggcc ttaaggacac cttttctgc     5160
atccctgtat atcctgactc tcaattcttg tttgcctttg aagatccttc aaactcaacg    5220
tctcaactca cctggaatgt tttaccccaa gggttcaggg atagccccca ttagcccaag    5280
acttgagcca gttcttatac ctggacactc ttgtcctttg gtacgtggat gatttactttt   5340
tagccacctg ttcagaaacc ttgtgccatc aagccaccca agcactcttt aatttcctcg    5400
```

```
ccacctgtgg ctacaggttt ccaaaccaaa ggctcagctc tgctcacagc aatttaaatg    5460
cttagggcta aaattatcca aaggcaccag ggccctcagt gaggaaagta tccggcctat    5520
actggcttat cctcatccca aaaccctaaa gcaactaaga gtgttccttg cataacggg     5580 tttctgccga atatggattc ccaggtacag cgaaatagcc agaccattat atacactaat    5640
taaggaaact cagaaagcca atacccattt ggtaagatgg acacctgaag cagaagcaga    5700
tttccaggcc ctaaagaagg ccctgaccca agccccagtg ttaagcttgc caatggggca    5760
agacttttct ttatatgtca cagaaaaaac aggaatagct ccaggagtcc ttacgcagat    5820
ccaagggacg agcctgcaac ccatggcata cctgagtaag gaaattagtg gcaaagggtt    5880
ggcctcattg tttatgggta gtggcagcag tcacagtctt agtaactgaa gcagttaaaa    5940
tgatacaagg aagagatctt actgtgtgga catctcatga tgtgaatggc atactcactg    6000
ctaaaggaga cttgtgactg tcagacaact gtttacttaa atatcaggct ctattacttg    6060
aagggccagt gttgcgactg tgcacttgtg caactcttaa cccagccaca ttgcttccag    6120
acaatgaaga aaagatagaa cataactgtc aacaataat tgctcaaacc tacactgctc    6180
gagggaccct tttagaagtt cccttgactg atcccgatct caacttgtat actgatggaa    6240
gttcctttgc agaaaaagga cttcaaaagg cggtgtatgc agtagtcctt caaaatcgaa    6300
gagctttaga attgctaatc actgagagag ggggaacgtt tttatttta ggggaagaat    6360 gctgttatta tgttaatcaa ttcggaatca tcaccaagaa agttaaagaa attcaagatc    6420
gaatacaacg tagaacagag gagcttaaaa aacactggac cctggggcct cctcagccaa    6480
tggatgccct ggattctccc cttcttagga cctctagcag ctatatttct actcctcttt    6540
ggaccctgta tctttaacct ccgtgttaag tttgtctctt ccagaatcga agatgtaaaa    6600
ctacaaatcg ttcttcaaat ggaccccag atgcagtcca tgactaagat ctactgagga    6660
cccctggacc agcctgctag cccatgctcc aatgttaatg acattgaagg cacccctccc    6720
aaggaaatct caactgcaca acccctacta tgctccaatt cagcaggaag cagttacagt    6780
ggtcctcggc caacctcccc aacagcattt gtattttcct gttggagggg gcactgaga    6840 gacaggacta gctggatttc ctaggctgac tgagaatccc taagcctagc tgggaaggtg    6900
accacttcca cctttaaaca cagggcttgc aacttagctc acaccctacc aattggatag    6960
taaagagagg tcactaaaat gctaattagg caaaaacagg aggtaaagaa atagccaatc    7020
atccattgcc tgagagcaca gcgggaggga caatgaccag gatataaaacc caggcattcc    7080 agcctgcaac ggcaaccccc tttgggtccc ctctctttgt atgggagctc tgttttcact    7140
ctattcaatc ttgcaactgc actcttctgg tccgtgtttg ttacggctca agctgagctt    7200
ttgctcacca tccaccactg ctgtttgccg ccgttgcaga cccgtcgctg acttccatcc    7260
ctccagatct ggcagggtgt ccactgtgct cctgatccag cgaggcaccc attgccactc    7320
ccgatcaggc taaaggcttg ccattgttcc tgcacagcta agtgcctggg ttcgtcctaa    7380
tcaagctgaa cactagtcac tgggttccat ggttctcttc catgacccat ggcttctaat    7440
agagctataa cactcaccgc atggcccaag attccattcc ttggaatccg tgaggccaag    7500
aaccccaggt cagagaacac gaggctgccg ccatcttgga ag                      7542
```

<210> SEQ ID NO 6
<211> LENGTH: 10288
<212> TYPE: DNA
<213> ORGANISM: Homo sapiens

```
<400> SEQUENCE: 6
cctggggcgg gcttcctttc tgggatgagg gcaaaacgcc tggagataca gcaattatct     60
tgcaactgag agacaggact agctggattt cctaggccga ctaagaatcc ctaagcctag    120
ctgggaaggt gaccacgtcc acctttaaac acggggcttg caacttagct cacacctgac    180
caatcagaga gctcactaaa atgctaatta ggcaaagaca ggaggtaaag aaatagccaa    240
tcatctattg cctgagagca cagcaggagg acaacaatc gggatataaa cccaggcatt     300
cgagctggca acagcagccc cccttttgggt cccttcccctt tgtatgggag ctgttttcat  360
gctatttcac tctattaaat cttgcaactg cactcttctg gtccatgttt cttacggctc    420
gagctgagct tttgctcacc gtccaccact gctgtttgcc accaccgcag acctgccgct    480
gactcccatc cctctggatc ctgcaggtgt ccgctgtgc tcctgatcca gcgaggcgcc     540
cattgccgct cccaattggg ctaaaggctt gccattgttc ctgcacggct aagtgcctgg    600
gtttgttcta attgagctga acactagtca ctggttcca tggttctctt ctgtgaccca     660
cggcttctaa tagaactata acacttacca catggcccaa gattccattc cttgaatcc     720
gtgaggccaa gaactccagg tcagagaata cgaggcttgc caccatcttg gaagcggcct    780
gctaccatct tggaagtggt tcaccaccat cttgggagct ctgtgagcaa ggaccccccg    840
gtaacatttt ggcaaccacg aacggacatc caaagtggtg agtaatattg gaccactttc    900
acttgctatt ctgtcctatc cttccttaga attggaggaa aataccgggc acttgtcggc    960
cagttaaaaa cgattagtgt ggccaccgga cttaagactc aggtgtgagg ctatctgggg   1020
aagggcttc taacaacccc caaccccttct gggttgggga cttggtttgc ctcaagccag   1080
cttccacttt cagttttctt ggggaagccg agggccgact agaggcagaa agctgtcgtc   1140
ctgaactccc ggcagtagcc ggttgagatc atggtgtagc cagaagtctc aacagtcgcc   1200
catgcatgca cccctatctt tccttctgac ccataccctcc tgggtcccaa ccacaacttt  1260
cttcaaagtg tagccccaaa attctcctta cctctgaata tacttcctct gatccctgcc   1320
tcctaggtac tattggttca gacttccatt tcctctagca agttgtatct ccaaagggat   1380
ctaaggaagc tctgcgctgc gtccttaggc acctaggcta taacccaggg agtcttatcc   1440
ctggtgtccc tcccaattta ggcatacagc tcttgacatg ggcagttatg taggacccac   1500
tccccaccac ccttgccagg gccccaagtt tgtaaatggc tgagggaaaa gagagacaga   1560
ggagagagag agaaatggag gagaaagaga gagagacaga gaggagagag agacagtgag   1620
agagacagaa gagagagaga gacaaagagg agagagagag agtcaaagag agaaagaaag   1680
agaaagaaat agtaaaaaac agtgtgccct attcctttaa aagccagggt aaatttaaaa   1740
cctgtacttg ataattgaag gtcttctctg tgaccctata gcactccaat ccactttgtg   1800
gtcagtgtaa ataagagcat aggccgaaag cactgaggcc attgacaacc cgtagcttcc   1860
ctatcaaaaa tccttaaccc agtaaccccgc agatggacca aatgcattca gtcggtagcg   1920
caactgcttt gctaaaagta gaaaagtaac ttttagagga aacctcattg tgagcacacc   1980
tcacctgttc agaattattc taataaaaaa agcaaaaagg tagcttacta actcaaaaat   2040
cttaaagtat ggggctattc tgttagaaaa aggtaatgta actccaacca ctgataattc   2100
ccttaaccca gcagatttcc taacgggatt taaatcttaa ttaccataca aaggtccgac   2160
cagacctagg cggaactccc ttcaggacag gacgatagat ggttcctccc aggtgattga   2220
ggaaaaaaac cacaatgggt attcagtaat tgatacgggg actcttgtgg aagcagagtt   2280
agaaaaattg cctaataact ggtctcctca aacgtgtgag ctgtttgcac tcagccaagc   2340
```

```
cttaaagtac ttacagaatc aaaagactat ctcaatcctg attcaaaagg ttagctacac    2400
cctctctgta atgcatttgc ataagaactt gtttatggga atgcatcttg atggggcagc    2460
tgggttgtta taaaatagga acccagccca gctctaggac tcaccsctga gcgcaaaggc    2520
```
```
cttaaagtac ttacagaatc aaaagactat ctcaatcctg attcaaaagg ttagctacac    2400
cctctctgta atgcatttgc ataagaactt gtttatggga atgcatcttg atggggcagc    2460
tgggttgtta taaaatagga acccagccca gctctaggac tcacccctga gcgcaaaggc    2520
aatgttgggc atgctggtaa aggaccacta gaatccagca gcccagaccc ctttctttgt    2580
ggtcaagaaa ggcgggaaaa ggggtgcagg actgctacat cggtaagcat aactaatccg    2640
ataaacagag gtccatgggt ggttacgcac cctggaaagg aactcacccc tgagcacaaa    2700
ggcaatgttg ggcacgctgg taaaggacca ctagaatcca gcagcctgga ccccttctt     2760 tgtggtcaag agaggcagga aaacaggtgc aggactgcaa catcagtgag cataactaat    2820
tcgataagca gaggtccatg ggtggtgatg caccctggaa agaataagca ttaggaccat    2880
agaggacact ccaggactaa agctcatcgg aaaatgacta gggttgctgg catcccatatg   2940 ttcttttttc agatgggaaa cgttccccgc aagacaaaaa cgcccctaag acgtattctg    3000
gagaattggg accaatttga ccctcagaca ctaagaaaga aacgactat  attcttctgc    3060 agtgccgcct ggcactcctg agggaagtat aaattataac accatcttac agctagacct    3120
cttttgtaga aaaggcaaat ggagtgaagt gccataagta caaactttct tttcattaag    3180
agacaactca caattatgta aaaagtgtga tttatgccct acaggaagcc ttcagagtct    3240
acctccctat cccagcatcc ccgactcctt ccccaactaa taaggacccc ccttcaaccc    3300
aaatggtcca aaggagata gacaaagggg taaacagtga accaaagagt gccaatattc     3360
cccaattatg ccccctccaa gcagtgggag aagagaatt cggcccagcc agagtgcatg    3420 tgccttttc tctcccagac ttaaagcaaa taaaaacaga cttaggtaaa ttctcagata    3480
accctgatgg ctatattgat gttttacaag ggttaggaca attctttgat ctgcatgga    3540 gagatataat gtcactgcta aatcagacac taaccccaaa tgagagaagt gccaccataa    3600
ctgcagcctg agagtttggc gatctctggt atctcagtca ggtcaatgat aggatgacaa    3660
cagaggaaag agaatgattc cccacaggcc agcaggcagt tcccagtcta gaccctcatt    3720
gggacacaga atcagaacat ggagattggt gctgcagaca tttgctaact tgtgtgctag    3780
aaggactaag gaaaactagg aagaagtcta tgaattactc aatgatgtcc accataacac    3840
agggaaggga agaaaatcct actgcctttc tggagagact aagggaggca ttgaggaagc    3900
gtgcctctct gtcacctgac tcttctgaag gccaactaat cttaaagcgt aagtttatca    3960
ctcagtcagc tgcagacatt agaaaaaaac ttcaaaagtc tgccgtaggc ccggagcaaa    4020
acttagaaac cctattgaac ttggcaacct cggttttta taatagagat caggaggagc     4080
aggcggaaca ggacaaacgg gattaaaaaa aaggccaccg ctttagtcat gaccctcagg    4140
caagtggact ttggaggctc tggaaaaggg aaaagctggg caaattgaat gcctaatagg    4200
gcttgcttcc agtgcggtct acaaggacac tttaaaaaag attgtccaag tagaagtaag    4260
ccgccccctc gtccatgccc cttatttcaa gggaatcact ggaaggccca ctgccccagg    4320
ggacaaaggt cctctgagtc agaagccact aaccagatga tccagcagca ggactgaggg    4380
tgcctggggc aagcgccatc ccatgccatc accctcacag agccctgggt atgcttgacc    4440
attgagggcc aggaggttgt ctcctggaca ctggtgcggt cttcttagtc ttactcttct    4500
gtcccggaca actgtcctcc agatctgtca ctatctgagg gggtcctaag acgggcagtc    4560
actagatact tctcccagcc actaagttat gactggggag cttattctt ttcacatgct    4620 tttctaatta tgcttgaaag ccccactacc ttgttaggga gagacattct agcaaaagca    4680
```

-continued

```
ggggccatta tacacctgaa cataggagaa ggaacacccg tttgttgtcc cctgcttgag    4740
gaaggaatta atcctgaagt ctgggcaaca aaggacaat atggacgagc aaagaatgcc     4800
cgtcctgttc aagttaaact aaaggattcc acctcctttc cctaccaaag gcagtacccc    4860
ctcagaccca aggcccaaca aggactccaa aagattgtta aggacctaaa agcccaaggc    4920
ctagtaaaac catgcagtaa cccctgcagt actccaattt taggagtaca gaaacccaac    4980
agacagtgga ggttagtgca agatctcagg attatcaatg aggctgttgt tcctctatag    5040
ccagctgtac ctagccctta tactctgctt tcccaaatac cagaggaagc agagtggttt    5100
acagtcctgg accttcagga tgccttcttc tgcatccctg tacatcctga ctctcaattc    5160
ttgtttgcct ttgaagatac ttcaaaccca acatctcaac tcacctggac tattttaccc    5220
caagggttca gggatagtcc ccatctattt ggccaggcat tagcccaaga cttgagccaa    5280
tcctcatacc tggacacttg tccttcggta ggtggatgat ttacttttgg ccgcccattc    5340
agaaaccttg tgccatcaag ccacccaagc gctcttcaat ttcctcgcta cctgtggcta    5400 catggttttcc aaaccaaagg ctcaactctg ctcacagcag gttacttagg gctaaaatta    5460
tccaaaggca ccagggccct cagtgaggaa cacatccagc ctatactggc ttatcctcat    5520
cccaaaaccc taaagcaact aaggggattc cttggcgtaa taggtttctg ccgaaaatgg    5580
attcccaggt atggcgaaat agccaggtca ttaaatacac taattaagga aactcagaaa    5640
gccaataccc atttagtaag atggacaact gaagtagaag tggctttcca ggccctaacc    5700
caagccccag tgttaagttt gccaacaggg caagacttt cttcatatgt cacagaaaaa     5760
acaggaatag ctctaggagt ccttacacag atccgaggga tgagcttgca acctgtggca    5820
tacctgacta aggaaattga tgtagtggca aagggttgac ctcattgttt acgggtagtg    5880
gtggcagtag cagtccttagt atctgaagca gttaaaataa tacagggaag agatcttact    5940
gtgtggacat tcatgatgt gaatggcata ctcactgcta aaggagactt gtggctgtca     6000
gacaactgtt tacttaaatg tcaggctcta ttacttgaag gccagtgct gcgactgtgc     6060 acttgtgcaa ctcttaaccc agccacattt cttccagaca atgaagaaaaa gataaaacat   6120 aactgtcaac aagtaatttc tcaaacctat gccactcgag gggacttttt agaggttcct    6180
ttgactgatc ccgacctcaa cttgtatact gatggaagtt cctttgtaga aaaaggactt    6240
cgaaaagtgg ggtatgcagt ggtcagtgat aatggaatac ttgaaagtaa tcccctcact    6300
ccaggaacta gtgctcagct agcagaacta atagccctca cttgggcact agaattagga    6360
gaagaaaaaa gggcaaatat atatacagac tctaaatatg cttacctagt cctccatgcc    6420
catgcagcaa tatggaaaga aagggaattc ctaacttctg agagaacacc tatcaaacat    6480
caggaagcca ttaggaaatt attattggct gtacagaaac ctaaagaggt ggcagtctta    6540
cactgccggg gtcatcagaa aggaaaggaa agggaaatag aagagaactg ccaagcagat    6600
attgaagcca aaagagctgc aaggcaggac cctccattag aaatgcttat aaaacaaccc    6660
ctagtatagg gtaatcccct ccgggaaacc aagcccagt actcagcagg agaaacagaa     6720
tggggaacct cacgaggaca gttttctccc ctcgggacgg ctagccactg aagaagggaa    6780 aatactttg cctgcaacta tccaatggaa attacttaaa accctcatc aaacctttca      6840 cttaggcatc gatagcaccc atcagatggc caaatcatta tttactggac caggcctttt    6900
caaaactatc aagcagatag tcagggcctg tgaagtgtgc cagagaaata atcccctgcc    6960
ttatcgccaa gctccttcag gagaacaaag aacaggccat tacctggag aagactggca     7020 actgatttta cccacaagcc caaaccctcag ggatttcagt atctactagt ctgggtagat   7080
```

```
actttcacgg gttgggcaga ggccttcccc tgtaggacag aaaaggccca agaggtaata    7140
aaggcactag ttcatgaaat aattcccaga ttcggacttc cccgaggctt acagagtgac    7200
aatagccctg cttccaggc cacagtaacc cagggagtat cccaggcgtt aggtatacga    7260
tatcacttac actgcgcctg aaggccacag tcctcaggga aggtcgagaa atgaatgaa     7320
acactcaaag gacatctaaa aaagcaaacc caggaaaccc acctcacatg cctgctctg     7380
ttgcctatag ccttaaaaag aatctgcaac tttccccaaa aagcaggact tagcccatac    7440
gaaatgctgt atggaaggcc cttcataacc aatgaccttg tgcttgaccc aagacagcca    7500
acttagttgc agacatcacc tccttagcca aatatcaaca agttcttaaa acattacaag    7560
gaacctatcc ctgagaagag ggaaaagaac tattccaccc ttgtgacatg gtattagtca    7620
agtcccttcc ctctaattcc ccatccctag atacatcctg ggaaggaccc tacccagtca    7680
ttttatctac cccaactgcg gttaaagtgg ctggagtgga gtcttggata catcacactt    7740
gagtcaaatc ctggatactg ccaaaggaac ctgaaaatcc aggagacaac gctagctatt    7800
cctgtgaacc tctagaggat ttgcgcctgc tcttcaaaca acaaccagga ggaaagtaac    7860
taaaatcata aatccccatg gccctccctt atcatatttt tctctttact gttcttttac    7920
cctctttcac tctcactgca cccctccat gccgctgtat gaccagtagc tccccttacc    7980
aagagtttct atgagaatg cagcgtcccg gaaatattga tgcccatcg tataggagtc     8040
tttctaaggg aaccccacc ttcactgccc acacccatat gccccgcaac tgctatcact    8100
ctgccactct ttgcatgcat gcaaatactc attattggac aggaaaaatg attaatccta    8160
gttgtcctgg aggacttgga gtcactgtct gttggactta cttcacccaa actggtatgt    8220
ctgatggggg tggagttcaa gatcaggcaa gagaaaaaca tgtaaaagaa gtaatctccc    8280
aactcacccg ggtacatggc acctctagcc cctacaaagg actagatctc tcaaaactac    8340
atgaaaccct ccgtacccat actcgcctgg taagcctatt taataccacc ctcactgggc    8400
tccatgaggt ctcggcccaa aaccctacta actgttggat atgcctcccc ctgaacttca    8460
ggccatatgt ttcaatccct gtacctgaac aatggaacaa cttcagcaca gaaataaaca    8520
ccacttccgt tttagtagga cctcttgttt ccaatctgga ataacccat acctcaaacc     8580
tcacctgtgt aaaatttagc aatactacat acacaaccaa ctcccaatgc atcaggtggg    8640
taactcctcc cacacaaata gtctgcctac cctcaggaat attttttgtc tgtggtacct    8700
cagcctatcg ttgtttgaat ggctcttcag aatctatgtg cttcctctca ttcttagtgc    8760
cccctatgac catctacact gaacaagatt tatacagtta tgtcatatct aagcccgca     8820
acaaaagagt acccattctt cctttgtta taggagcagg agtgctaggt gcactaggta    8880
ctggcattgg cggtatcaca acctctactc agttctacta caaactatct caagaactaa    8940
atggggacat ggaacgggtc gccgactccc tggtcacctt gcaagatcaa cttaactccc    9000
tagcagcagt agtccttcaa aatcgaagag ctttagactt gctaaccgct gaaagagggg    9060
gaacctgttt attttaggg gaagaatgct gttattatgt taatcaatcc ggaatcgtca     9120
ctgagaaagt taagaaatt cgagatcgaa tacaacgtag agcagaggag cttcgaaaca    9180
ctggaccctg gggcctcctc agccaatgga tgccctggat tctccccttc ttaggacctc    9240
tagcagctat aatattgcta ctcctctttg gaccctgtat cttaacctc cttgttaact     9300
ttgtctcttc cagaatcgaa gctgtaaaac tacaaatgga gcccaagatg cagtccaaga    9360
ctaagatcta ccgcagaccc ctggaccggc ctgctagccc acgatctgat gttaatgaca    9420
```

```
tcaaaggcac ccctcctgag gaaatctcag ctgcacaacc tctactacgc cccaattcag    9480
caggaagcag ttagagcggt cgtcggccaa cctccccaac agcacttagg ttttcctgtt    9540
gagatggggg actgagagac aggactagct ggatttccta ggctgactaa gaatccctaa    9600
gcctagctgg gaaggtgacc acatccacct ttaaacacgg ggcttgcaac ttagctcaca    9660
cctgaccaat cagagagctc actaaaatgc taattaggca aagacaggag gtaaagaaat    9720
agccaatcat ctattgcctg agagcacagc aggagggaca atgatcggga tataaaccca    9780
agtcttcgag ccggcaacgg caacccctt tgggtcccct ccctttgtat gggagctctg    9840
tttcatgct atttcactct attaaatctt gcaactgcac tcttctggtc catgtttctt    9900
acggcttgag ctgagctttc gctcgccatc caccactgct gtttgccgcc accgcagacc    9960
cgccgctgac tcccatccct ctggatcatg cagggtgtcc gctgtgctcc tgatccagcg   10020
aggcacccat tgccgctccc aatcgggcta aaggcttgcc attgttcctg catggctaag   10080
tgcctgggtt catcctaatt gagctgaaca ctagtcactg ggttcatgg ttctcttctg    10140
tgacccacag cttctaatag agctataaca ctcaccgcat ggcccaaggt tccattcctt   10200
gaatccataa ggccaagaac cccaggtcag agaacacgag gcttgccacc atcttgggag   10260
ctctgtgagc aaggaccccc aagtaaca                                     10288

<210> SEQ ID NO 7
<211> LENGTH: 6818
<212> TYPE: DNA
<213> ORGANISM: Homo sapiens

<400> SEQUENCE: 7
gcaactccct ttgggtctcc tctcattgta tgggagctct gttttcactc tattaaatct      60
tgcaactgca cactcttctg gtctgtgttt gttatggctt gagctgagct tttgctggct     120
gtccaccact gctgtttgct gccgtcgcag acccttgct gactcccacc cctgcggatc      180
tggcagggtg tctgctgcgc tcctgatcca gccaggcacc cactgctgct cccaatcagg     240
ctaaaggctt gccattgttc ctgcatggct aagtgcccgg gttcgtgcta attgagctga     300
acactagtcg ctgggttcca cagttctctt ccgtgaccca cagcttctaa tagagctata     360
acactcactg catggcccaa cattccattc cttggaatct gtgaggccaa gaaccccggg     420
tcagagaaca agaagcttgc caccatcttg gaagcagccc gccaccattt tgggagctct     480
aagaacaagg ccccccagt aacatttggg tgaccacgaa gggacctcca aagcagtgag     540
taatattgaa ccacttccgc ttgctattct gtccctaacct tccttagaat tggaggaaaa     600
taccgggcac ctgtcggcca gttaagaacg attagcgtgg ccgccagact taagactctg     660
gtgtgaggct gtctgggaaa gggctttcta acaaccccca acccttccgg gttgggagct     720
ttggtctgcc tggaaccagc ttccactttc aattttcctg gggaatccaa gggctgacta     780
gaggcagaaa gctgtcatcc cgaactcctg gcattagaca gttgagatcg tggcgcagcc     840
agaagtctct actcaacagt cacccatgcg tgcacccta ccttcccttc taacccatac     900
ctcccgggtc ccaaccatga ctttcttgaa agtgtagccc ctaaattctc tttacctcta     960
aatctacttc ttctcatccc tgcttcctag gtactaatgg ttcagacttt catttcctct    1020
agcaagttct atctccagag ggatctaagg aagggatcta tgctgtgtcc ttaggcccct    1080
aggctatgaa cccagagagt cttctcccctg ttatctctcc ccatttaggc atacagctct    1140
caacatggac agttatgtgg gacccattcc ctaccaccct tgccagggcc ccaagttttc    1200
aaagggctag aagaaaaaag agagaaagag agagagaggc agaggggaga gaaagagaga    1260
```

```
gagacaaaga gggagtcaaa gagagataga aagagaaaga tagaactagt aaagaaaaaa    1320
agtatgcccc attcctttaa aagccagggt aaatttaaaa cctataattg ataattgaag    1380
gtcttctcca tgaccctata acactccaat accaccttgt tttcagtgta aacaagggtg    1440
tagcccgaaa acactgagac cactgacaac ccatagcctt cctatcaaaa atccttaacc    1500
caggaaccca tggatggccc aaatgcattc aatctgtagc agcaactgct ttgctaacag    1560
aagaaagtag aaaagtaact tttagagaaa acctcattgt gagcacacct caccagttca    1620
gaattattct aagtcaaaaa agcaaaaagg tagcttacta actcaaaaat cttaaagtat    1680
ggggttattc tgttagaaaa aggtgattta acattaacca ctgaaaattc ccttaaccca    1740
gcaggtttcc taatgggatt taaatcttca ttaccataca aaggtccgac cagacccagc    1800
aggaactccc tttaggacag gatgatagat ggttcctcct gggtgattga ggggtgaaa    1860 aaccacaatg ggtgttcagt aattgatagg gagactcttg tggaaggaga gttaggaaaa    1920
ttgcctaata attggtctgc tcaaatgtgc gagctgtttg cactcagcca agccttaaag    1980
tacttacaga atcaaaaaga ctctatctca atcctgactc aaaatgttac ctacaccatc    2040
tctgacatga atttgcataa gaactgttgt ttatgggaat gcatcttgat ggggcagctg    2100
ggttgttatg aaatactcag gaacccagcc caggtctaga attcacctct gagcgcaaag    2160
gcaatgttgg ccatgctggt aaaggaccac tagaatccag gagcctggac ccctttcttt    2220
gtggtcaaga aaggcgggaa acaggtgca ggactgctac atcagagagc ataacaaatc    2280
cgataagcag agttccatga gtggttaagc accctggaaa ggaactcacc tctgagtgca    2340
aaggcaatgt taggcacacc agtaaaggac cactagaatc cagcagccca gacccctttc    2400
tttgtgatca agaaaggcgg gaaaaggggt gcaggactgc tacatcagtg agcgtaacta    2460
atctgataag cagaagtcca tgggtggtta cgcaccctgg aaaggaataa gcattaggac    2520
cacagaggac actctaagac taatgctcat tggaaaatga ctaggggtgc tggcatccct    2580
atgttttttt ttcagatggg aaacattccc cccaaggcaa aaacgcccat aagatatatt    2640
ctggagaatt cggcccagag tgtatgtatc ttttttcctt gtcagacttg aagcaaacct    2700
aggtaaatta tcagatagcc ctgatggcta tattgatgct ttacaagggt taggacaatc    2760
ctttgatcta acatggagag atatactgtt actgctagat cagacactaa tcccaaatga    2820
aagaagtgcc accataactg cagccagaga gtttgatgat ctctggtatc tcagtcaggt    2880
caatgatagg atgacaacag aagaaagaaa acaattcccc acaggccagc aggcagttcc    2940
cagcgtagac cttcattggg acacagaatc agaacatgga gattggtgcc gcagacattt    3000
actaacttgc gcgctagaag cactaaggaa aactaggaag aagcctatga attattcaat    3060
gatgtccact ataacacagg gaaaggaaga aaatcctact gcctttctgg agagactaag    3120
ggaggcattg agaaagcata cctctctgtc acctgactct attgaaggcc aactaatctt    3180
aaaggataag ttttccactc agtcagctgc agacattaga aaaaaacttc aaaagtctgc    3240
gttaggccgg gagcaaaact tagaaaccct attgaacttg gcaacctcag tttttttatga    3300 tagagatcag gaggatcagg tggaatggac aaatgagatt ttaaaaaaag gccaccactt    3360
tagtcatggc cctcaggcaa gcagactttg gacactctgg aaagggaaa agctgggcaa    3420 atcgaatgcc taataagact tgcttccagt gtggtctaca aggacacttt aaaaaagatt    3480
gtccaaatag aaataagcca ccccctcgtc catgctcctt atgtcaaggg aatcactgga    3540
aggcctactg ccccagggga tgaaggtcct ctgagtcaga agccactaac cagatgattc    3600
```

-continued

```
agccccagga ctcagggtgc ccagggcaag cgccagccta tgccatcacc ctcacagagc    3660
cctgggtatg cttgaccatt gagggtcagg aggttaacta tctcctggac actggcgtgg    3720
ccttctcagt cttactctcc tgtcccggac aactgtcctc cagatctgtc actatccgag    3780
ggtttctacg acagccagcc actagatact tctcccagcc actaagttgt gactggggaa    3840
ctctactctt ttcacatgtt tttctaatta tgcctgaaag ccccactcct ttgttaggga    3900
aagacattct agcaaaagca ggggccatta tacacctgaa cataggagaa ggaacacctg    3960
tttgttgtcc cctgcttgaa gaaggaatta atcctgaagt ctggacaaca aaggacaat    4020 acagatgagc aacaaatgcc tgtcctgttc aagttaaact aaaggattat gcctcctttc    4080
cctaccaaag gcagtacccc cttagacccg aggcccaaca aggactccaa aagattgtta    4140
aggacctaaa agctcaaagc ctagcaaaac catgcagtag cccctgcaat actccaattt    4200
taggagtaca gaaaaccaac agacagtgga ggttagtgca agatctcagg attatcaatg    4260
aggctgttgt tcctaaccct tatactctgc tttcccaaat accagaagaa gcagagtggt    4320
ttacagtcct ggaccttaag gatggctttt tctgcatccc tgtacatcct gactctcaat    4380
tcttgtttgc ctttggagat ccttcgaacc caatgtctca actcagcttg actgttttac    4440
cccaagggtt cagggatagc ccccatctag ttggccaagc attagccgag ccagttctcc    4500
tacctggaca ctcttgtcct ctggtacatg gatgattat ttttagctgc ccgttcagaa    4560
accttgtgcc atcaagccac ccaagtgctc ttaaatttcc tcgccacctg tggctacaag    4620
gtttccaaac caaaggctca gctctgctca cagcaggtta aatacttagg gctaaaatta    4680
tccaaaggca ccagggccct cagtgaggaa tgtatccagc ctgtattggc ttatcctcat    4740
cccaaaaccc taaagcaact aagagggttc cttggcataa caggtttctg ccaaatgtgg    4800
attcccaggt acggtgaaat agccaggcca ttatataccc taattaagga aactcagaaa    4860
gccaacaccc atttattaag atggacacct gaagcagaag cagctttcca ggccctaaag    4920
aaggccctaa cccaagcccc agtgttaagc ttgccaacgg ggaagacttt tctttatatg    4980
tcacagaaaa aacaggaata gctctaggag tccttagaca ggtccaaggg atgagcttgc    5040
aacctgtggc atacctgagt aaggaaattg atgtagttgc aaagggttga cctcattgtt    5100
tacaggtagt ggcggcagta gcagtcttag tatctgaagc agttaaaata atacagggaa    5160
gagatcttac tgtgtggaca tctcatgatg taaacggcgt actcacttct aaaggagact    5220
tgtggctgtc agacaaccgt ttacttaaat atcaggctct attacttgaa gggccagtgc    5280
tgcgactgcc cacttgttca actcttaacc cagccacatt tctttcagac aatgaagaaa    5340
agatagaaca taactgtcaa caggtgattg ctcaaaccta cggcgctcga ggggaccttc    5400
tagaggttcc cttgactgat cccaacctca acttgtatac tgatggaagc tcctttgtag    5460
aaaaaggact ttgaaaggtg gggtatgcag tggtcagtga taatggaata cttgaaagta    5520
attccttcac tccaggaact agtgctcagc tggcagaact aatagccctc actcaggcac    5580
tagaattagg agaaggaaaa agggtaaata tatatgcaga ctctaagtat gcttacccag    5640
tcctccacgc ccacacagca atatggagag ataggaaatt cctaacttct gagggaacac    5700
cgatcaaaca tcaggaagcc attaggagat tattattggc tgtacagaaa cctaaagagg    5760
tggcagtctt acactgctgg ggtcatcaga aggaaagga aaaggaaata gaaaggaacc    5820
accaagtgga tattgaagcc aaaagagcca caggcaggc cctccattag aaatgcttat    5880
agaaggatcc ctagtatggg gtaatcccct ccgggaaacc aagccccagt actcagcagg    5940
agaaatagac acgaggacat agtttcctcc cctcaggatg gctagccacc gaaaaaggga    6000
```

-continued

```
aaatacttttt gcctgcagct aatcaatgga aattacttaa aacccttcac caaacctttc     6060
acttgggcat ggatagcatc tatcagatgg ccaatttatt atttactgga ccaggccttt     6120
tcaaaactat caagcagata gtcagggcct gtgaaatgtg ccaagaaat aatcccctgc     6180 acttcaagcc atacatttca atccctgtat ctttaacctc ctgttgtttg tctcttccag     6240
actcaaagct gtaaaactgc aaatggttcc tcatatggag ccccagatgc agtccatgac     6300
taagatctac cacagagccc tagaccggcc tgttagccca tgctccgatg ttgatgacat     6360
caaaggcaca ccttccgagg aaatctcaac tgcacgaccc ctactaagcc ccaattcagc     6420
aggaagcagt taagagcagt cgttggctaa catccccaat agtatgtggg ttttcctgtt     6480
gagagggggg actgagagac aggactagct ggatttccta ggccaactaa gaatccctaa     6540
gcctagttgg gaaggtgacc gcatccacct ttaaacacgg ggcttgcaac ttagctcaca     6600
cccgaccaat caggtagtaa agagagctca ctaaaatgct aattaggcaa aaacaagagg     6660
taaagaaata gccaatcatc tatcgcctga gagcacagtg ggagggaca atgatcggga     6720 tataaaccca ggcattcggg ccggcaacgg caaccccat tgcgtcccct cccattgtat     6780
gggagctctg ttttcattct attaaatctt gcaactgc                             6818
```

<210> SEQ ID NO 8
<211> LENGTH: 7073
<212> TYPE: DNA
<213> ORGANISM: Homo sapiens

<400> SEQUENCE: 8

```
gcaaccccct ttgggtctcc tcccttgca taggagctct gttttcactc tattaagtct      60
tgcaactgca ctcttctggt ccgtgtttct taccgcttga gctgagcttt ccctcactgt     120
ccaccactgc tgttttgcca ccgtcacagg cccaccgctg acttccattc ttctggatct     180
agcaggctgt ccactgtgct cctgatccag cgaggcgccc attgccgctc ccgattgggc     240
taaaggcttg ccattgttcc tgcatggcta cgtgcctggg ttcatcctaa tcaagccgaa     300
cactagtcac tgggttccac ggttctcttc catgacccac gacttctaat agaactataa     360
cactcacctc atggcccaag attccattcc ttggaatcca tgaggccaag aaccccaggt     420
cagagaacac gaggcttgcc accatcttgg aagtggcccc accaccatct tgggagctct     480
gggagcaagg accccggta acattttggc gaccacaaag ggacatccaa agtggtgagt     540
aatattggac cactttcact tgctattctg ttctatcctt ccttagaact ggaggaaaat     600
accaggcaca ggcacctgtc agccagttaa aaacaattag cgtcgccgcc acacttaaga     660
ctcaggtgtg aggctatctg gggaaagact ttctaacaac ccccaaccca tctagtgggg     720
atgttggtct gcctggagac agcttccact ttcaattttc ttggggaagc cgagggctca     780
ctagaggcag acagctgttg tcccaaactc cgggcagtag ccggttgaga tcatggtgca     840
gccaggagtc tctactcagc agtcgccgat gcatgtgccc ctaccttccc ttctgaccca     900
tacatcctga gtcccgactg tgactttctt gaaagtgtag ccccaaaatt ctccttacct     960
ctgaatctac ttcctctgat ccctgcctcc tgggtactaa tgattcagac tttcatttcc     1020
tctagcaagt tgtgtctcca aagggatcta aggaggctct acgctgcatc cttaggcacc     1080
taggctataa cccaaggagt cttatccctg gtgtccctcc cgatttgggt atacaactct     1140
caacatgggc agttatgtag gacccattcc ccaccacact tgccagggcc ccaagtttgt     1200
aatggctaag agagagacac agagagagag agagagatgg agagagagac aaggagggag     1260
```

```
tcaaagagaa aaagaaagaa aaagaaatag tagaaaaaaa agtgtgccct attcctttaa    1320
aagccagggt aaatttaaaa cctgtaattg ataattgaag gtcttctccg tgaccctgta    1380
acactccaat gccattttgt tgtcagtgta aataagggca tagcccaaaa gcactgaggt    1440
cactgacaac ccgtagcttt cccatcaaaa atccttaacc cagtaatccg cggatgggcc    1500
aaatgcattc agtcggtagc agcaaccgct ttgctaaaag tagaaaagta acttttagag    1560
gaaacctcat tgtgagcgca cacctcacca gttcagaatt attctaagtc aaaaaaaaaa    1620
aaagcaaaaa ggtaacttac taactcaaaa atcttaaagt ataggtctat catattagaa    1680
aagggtaatg taactccaac cactgataat tcccttaacc cagcagattt cctaacaggg    1740
gatttaaaac ttaattacca tacaaaggtc ccaccagacc taggaggaac tcccttcagg    1800
acaggacgat aaacggttcc tcccaggtga ttgaggaaaa aaaccacaat gggtattcag    1860
taattgatac agagactcat gtggaagcag ttagaaaaat tgcctaataa ttggtctcct    1920
caaacgtgta agctgtttgc actcagccaa gccttaaagt acttacagaa tcaaaaagac    1980
tctgaatcct gactcaaaag gtttgctaca ccctctgtga aacaaatttg cataagaact    2040
gttgtttatg ggaaggcatc ttgatggggc agctgggttg ttatgaaata ctcaggaccc    2100
cagcccggct ctaggactca cccctgagcg caaaaggcaa tgttgggcac gctggtaaag    2160
gaccactaga atccagcagc ccggaccccct ttctttgtgg tcaagagagg cgggaaaaca    2220
ggtgcaggac tgctacatca gtgagcataa ctaatccagt aagcagaggt ccatgggtgg    2280
ttatgcaccc tggaaaagaa tacgcattag gcccttagag gatgctctag gactaatgct    2340
catcggaaaa tgactagggg tgctgacatc cctatgttct tttttcagat gggaaacgtt    2400
cctcccaccc caaggcaaaa acaccccta agatgtattt tggagaatta ggaccaattt    2460
gaccctcaga cactaagaaa gaaatgactt acattcttct gcagtaccat gatatcctct    2520
tcaaggggga gaaacctggc ctcctgagag aagtataaat tataacacca tcttacagtg    2580
agacctcttc tgtagaaagg agggcaaatg gagtgaagtg caaactttcc tttcattaag    2640
agacaactcg caattatgta aaaagtgtga tttatgccct acagaaagcc ctcagtctac    2700
ctccctatcc cagggtcccc ccgattcctt tcccaactaa taaggacccc ccttttaccc    2760
aaatggtcca aaggagatag atgaagggat aaacaatgaa ccaaacagtg ccaatattcc    2820
ctgattatgc cccctccagg cagtgggagg aggagaattc ggcccagcca gagtgcatgt    2880 acctttttt ttctctcaga cttaaagcaa attaaaatag acctaggtaa attctcagat    2940
aaccctgatg gctatattga tgttttacaa gggttaggac aatcctttgc tctgacatgg    3000
agagatataa tgttactgct aaatcagaca ctaaccccaa atgagagaag tgtcaccata    3060
gctgcagccc aagagtttgg caatctctgg tatctcagtc aggtcaatga taggatgaca    3120
acagaggaaa gggaatgatt ccccacaggc cagcaggcag ttctcagtgt agaccctcac    3180
tgggacacag aataagaaca tggagatcgg tgccgcagat atttgctaac ttgcgtgcta    3240
ggactaagga aaactaggaa gaagcctatg aattattcag tgatgtccac tataacacag    3300
ggaaaggaag aaaatcatac tgcctttccg gaaatactaa gggaggcatt gaggaagcat    3360
acctctctgt cacctgactg tattgaagtc caactaatct taaaggatat gtttatcact    3420
cagtcagctg cagacattag aaaaaacttc aaaagtccac cttaggccca gagcaaaact    3480
tagaaaccct attgaacttg ttaacctcag tttttttataa tagagatcag gaggagcagg    3540
cggaacagga caaacaggat taaaaaagga ccaccgcttt agtcatggcc ctcaggcaag    3600
tggactttgg aagctctgga aaagggaaaa gctgggcaaa ttgaatgcct aatagggctt    3660
```

```
gcttccagtg tggtctacaa ggacacttaa aaaaagattg tccaagtaga aataagctgc   3720
cccttcgtcc atgcctctta tgtcaaggga atcactggaa ggcccattgc cccaggggag   3780
gaaggtcctc tgagtcagaa gccactaacc agatgatcca gcagcaggac taagggtgcc   3840
cagggcaagc cccagcccat gccatcaccc tcacagagcc ccgggtatgc ttgaccattg   3900
agggccagga ggttaactgt ctcctgaaca ctggcacagc cttctcagtc ttactttcct   3960
gtcccggaca actgtcctcc agatctgtca ctatctgagc ggtcctagga cagccagtca   4020
ctagatattt ctcccagcca ctaagttgtg actggggaac tttactcttt tcacatgctt   4080
ttctaattat gcctgaaagc cccactcctt gttagggag agacattcta gcaaaagcag    4140
gggccattat acatctgaac ataggagaag gaacacccgt tgttgtcac ctgcttgagg     4200 aaggaattaa tgctgaagtc tgggcaacag aaggacaata tggatgagca agaatgccc     4260 atcctgttca agttaaatta aaggattccg cctcctttcc ctaccaaagg caataccccc   4320
ttagacccga ggcccaacaa ggactccaaa agattgttaa ggacctaaaa gcccaaggcc   4380
tagtaaaacc atgcaatagc ccctgccata ctccaatttt aggagtaagg aaacccaacg   4440
gacagtggag gttagtgcaa gaactcagga ttatcaatga ggctgttgtt cctctatacc   4500
cagctgtacc taaccCttat acagtgcttt cccaaatacc agaggaagca gagtggttta   4560
cagtcctgga ccttaaggat gcctttttct gcatccctgt acgtcctgac tctcaattct   4620
tgtttgcctt tgaagatcct ttgaacccaa cgtctcaact cacctggact gttttacccc   4680
aagggttcaa ggatagcccc catctatttg gccaggcatt agcccaagac ttgagccaat   4740
tctcatacct ggacactctt atccttcggt atggggatga tttaatttta gctacccatt   4800
cagaaacgtt gtgccatcaa gccacccaag tgctcttaaa tttcctcgct acctgtggct   4860
acaggtttcc aaacgaaagg ctcagctctg ctcacagcag gttaaatact tagggctaaa   4920
attatccaaa ggcaccaggg ccctcagtga ggaacgtatc cagcctatac tggcttattc   4980
tcatcccaaa accctaaagc aactaagagc attccttggc ataacaggct gctgctgaat   5040
atggattccc aggtacagtg aaatagccag gccattatac acactaatta aggaaactca   5100
gaaagccaat acccatttag taagatggac accttaagca gaagcggctt tccaggcctt   5160
aaagaaggcc ctaacccaag ccccagtggt aagcttgcca acagggcaag acttttcttt   5220
atatgtcaca gaagaaacag gaatagctct aggagtcctt acacaggtct gagggatgag   5280
cttgcaaccc atggcatacc tgagtaagga aactgatgta gtggcaaagg gttggcctca   5340
ttgtttacgg gtagtggcag cagtagcagt cttagtatct gaagtagtta aataataca    5400 gggaagagat cttactgtgt gaacatctca tgatgtgaat ggcatagtca ctgctaaagg   5460
agacttgtgg ctgtcagaca actgtttact taaataccag gctctattac ttgaagggcc   5520
agtgctgcga ctgtgcactt gtgcaactct taacccagac acatttcttc cagacaatga   5580 agaaagata gaacataact gccaacaagt aattgctcaa acctatgcca ctcgagggga    5640 cctttagag gttcccttga ctgatcccaa cctcaacttg tatactgatg aagttcctc     5700 tgtagaaaaa ggactttgaa aagtggggta tgcagtggtc agtgataatg gaatacttga   5760
aagtaatccc ctcactccag gaactagtgc tcagctggca gaactaatag ccctcactcg   5820
ggcactagaa ttaggagaag agaaaagggt aaatatatac agactctaag tatgcttacc   5880
tagtcctcca tgcccatgca gcaatatgga gagaaaggga attcctaatt tccaagggaa   5940
cacctatcca acatcaggaa gccattagga gattactatt ggctgtacag aaacataaag   6000
```

| | |
|---|---:|
| aggtggcaat cttacactgc cggtgtcacc agaaaggaaa ggaaagggaa atagaaagga | 6060 |
| accaccaagc ggatattgaa gccaaaagag ccgcaaggca ggaccctcca ttagaaatgc | 6120 |
| ttatagaagg acccctagta tggggtaatc ccctccagga aaccaagccc cagtactcag | 6180 |
| aagaagaaat agaatgagga acctcacaag cacatagttt cctcccctca ggatggctag | 6240 |
| ccactgaaga aggaaaaata cttttgcctg cagctaacca atggaaatta cttaaaaccc | 6300 |
| ttcaccaaac atttccctta ggcattgata gcacccatca gatggccaaa ttattattta | 6360 |
| ctggaccagg cctttttcaaa actatcaagc agatagtcag ggcctgtaaa gtgtgccaaa | 6420 |
| caagtaatcc cctgcactgc aggccataca tttcaatccc tgtatcttta acctccttgt | 6480 |
| taagtttgtc tcttccagaa tcaaagctgt aaaactacaa atagttcttc aaatggagcc | 6540 |
| ccagatgtag tccatgacta agatctaccg cggacccctg acaagcctg ctagcccatg | 6600 |
| ctctgatgtt aatgacatgg aaggcacccc tcccgaggaa atcgcaactg cacaacccct | 6660 |
| attacacccc aattcagcag gaagcagtta gagcattcat cagccaacct ccccaacagc | 6720 |
| acttgggttt tcctattgag aggggtact gagagacagg actagctgga tgtcctaggc | 6780 |
| tgactaagaa tccctaagcc tagctgggaa ggtgaccaca tccaccttta aatacggggc | 6840 |
| ttgcaaccta gctcacaccc aacagatcag agagctcgtt aaaatgctaa ttaggcaaaa | 6900 |
| acaggaggta aagaaatagc caatcatcta ttgcctgaga gcacagcagg agggacaagg | 6960 |
| attgggatat aatcccaggc attcgagctg caacagcaa ccccctttgg gtcccctccc | 7020 |
| tttgtatggg agctgttttc actctatttc actctattaa atcttgcaac tgc | 7073 |

<210> SEQ ID NO 9
<211> LENGTH: 5068
<212> TYPE: DNA
<213> ORGANISM: Homo sapiens

<400> SEQUENCE: 9

| | |
|---|---:|
| gcaacctcct ttgagtcccc tcccttttgta taggagctct gttttcactg tgtttcactc | 60 |
| tattaaatct tgcaattgca ctcttctggt ccatatttgt cacggcttga gctgagcttt | 120 |
| cacttgccgt ccaccactac tgtttgctgc tgtcacagac ccgccgctga ctcccatccc | 180 |
| gctgctgact cccatccctc cggatccggc agggtgtccg ctgtgctcct gatccagcaa | 240 |
| gactcccatt gccactcccg atagtgctaa aggcttgcca ttgttcctgc atggctaagt | 300 |
| gcctgggttc gtcctaatcc agctgaacac tagtcactgg gttccacggt tctcttccat | 360 |
| gacccgcggc ttctaataga gctataacac tcaccacatg gcccaatatt ccattccttg | 420 |
| gaatccgtga ggccaagaac cccaggtcag agaacacgag gcttgccacc atcttggaag | 480 |
| cagcctgcca ccatcttgga agtggctcac caccgtcttg ggagttctgt gaacaaggac | 540 |
| ccctggtaac attttggcga ccacgaaggg acatccaaag ctgtgagtaa tattggacca | 600 |
| ctttcgcttg ctattctgtt ctatccttag aactggagga aaatactggg cacctgtcgc | 660 |
| cagttaaaaa tgattagcat ggccgccgga cttaagactc aggtgtgagg ctatctggga | 720 |
| aagggctttc taacaacccc caagccttct gttgggaact ttggtctgcc tggagccagc | 780 |
| ttccactttc aattttcttg gggaagccaa gggctgactg gaggcagaaa gctgttgtcc | 840 |
| cgaactcccg gcagtagccg gttgagatca tggcgcagcc agaagtctct actcggcagt | 900 |
| cgcccatgcg tgcgccctta cctttccttc tgaattatac ctccggggtc ccgactccga | 960 |
| cttttcttgag agtttagccc caaaattctc cttacctctg aatctacttc ctttgatccc | 1020 |
| tgcctcctgc ctcctaggta ctaatagttc agactttcat ttcctctagc aagttgtgtc | 1080 |

```
tccaaaggga tctaaggagg ctctatgctg tgtccttagg cacctaggct ataacccagg    1140
gagtcttatc cctggtatcc ctcccgattt aggtatacag ctcttgacat gggcagttat    1200
gtgggacctg ttccccacca cccttgtgag ggccccaagt ttgtaatggc taagaaagag    1260
agacggagag agagagagac ggagaaagag acaaagaggg agtcaaagag aaaaagaaag    1320
aaaaagatag aaatagttaa aaaaaaaaaa aagtgtgccc tattccttta aaagccaggg    1380
taaatttaaa acctgtaatt gataattgcc actttgttgt cagtgtaaat aagggcgtag    1440
caaatcctta acccagtaac ccgcggatag gccaaatgca ttcagtcggt agcggcaaca    1500
gctttgctaa aagtagaaaa gtaactttta gaggaaacct cattgtgagc cacctcacc     1560
agttcagagt tattctaagt aaaaaaaaaa aaaaaaaaaa aagcaaaaag gtagcttact    1620
aactcaataa tcttaaagta tggggctact atgctagaaa agggtaatgt aactccaacc    1680
actgataact cccttaaccc agcagatttc ctaacagggg atttaaatct taattaccac    1740
acgaaggtcc gaccagacct aggaggaact cccttcagca caggacgata gatggttcct    1800
cccaggtgac tgaggaaaaa actacaatgg gtattcagta attggtatgg agactcttgt    1860
ggaagcagag ttaaaaattt gcctaataat tggtctcctc aaatgtgcga gctgtttgca    1920
ctcagccaag ccttaaagta cttacagaat caaaagacta tctcaatcct gactcaaaag    1980
gttagctaca cagtctctga aatgaatttg cagaagaact gttgtttatg gaatgcatc     2040
ttgatgggc agctggttg ttatgaaata ctcaggaacc cagcccagct ctaggactca      2100
ccgctgagcg caaaggcaat gttgggcacg ctggtaaagg accactagaa tccagcagcc    2160
caggccccctt tctttgtggt caagaaaggc aggaaaagga gtgcagaact gctacattgg   2220
tgagcgtaac taatccaata agcagaggtc catgagtggt tatgcacgct ggaaaagaat    2280
aagcattagg cccttagagg atgctctagg actaatgctc atcggaaaat gactaggggt    2340
gctggcatcc ttatgttctt tcttcagatg ggaaacgttc ccccaaggc aaaagcgccc     2400
ctaagatgta ttctggagaa ttagaaccaa tttgacccte agatgtcaag aaagaaacga    2460
cttatattct tctgcagtac tgcctggcca cgatatcctc ttcaaggggg agaaacctgg    2520
cctcctgagg gaagtacaaa ttataacacc atcttacagc tagacctctt ttgtagaaaa    2580
gaaggcaaat ggagtgaagt gccatatgtg caaactttct tttcattaag agacaactca    2640
caattatgta aaaagtgtgg tttatgtctt acaggaagcc ctcagagtct acctccctat    2700
cccagcattc ccccgactcc ttccccaact aataagcacc acccttgaac ccaaacagtc    2760
caaaaggaga tagacaaaca ggtaaacaat gaaccaaaga gtgtcagtat tccccgatta    2820
tgccccttcc aagcagtggg aggaggagaa ttcggcccag ccagagtgca tgtacctttt    2880
tctctctcag acttaacgca aattaaaata gacttaggta aattctcaga taaccctgat    2940
ggctacattg atgttttaca agggttaggg caatcctttg atctgacatg gagagatata    3000
atgttactgc taaatcagac actaacccca aatgagagaa gtgccgccgt aactgcagcc    3060
cgagagtttg gtgatctctg gtatctcagt caggtcaatg ataggatgac aacagagaaa    3120
agagaacgat tccccacagg ccagcaggca gtttccagtg tagaccctca ttaggacaca    3180
gaatcagaac atggagattg gtgccacaga tatttgctaa cttgagtgct agaaggacta    3240
aggaaaacta ggaagaagcc tatgaattat tcagtgatgt ccactataac acaaggaaag    3300
gaagaaaatc ctactgcctt tctggagaga gtaaggagg cattaaggaa gcatacctcc     3360
ctgtcacctg actctattga aggccaacta atcttaaagg ataagtttgt cactcagtta    3420
```

-continued

| | |
|---|---|
| gctgcagaca ttagaaaaaa acttcaaaag tccgacttag gcctggagta cggctgagtg | 3480 |
| cccaatttgg cagcaggcaa gaccaacact gagcccttca tatggcacca tgctttgtgg | 3540 |
| tgatcagcca actacttgat ggcaggttga ttatattgga catctttcat cagagaaatg | 3600 |
| gcagtggttt gtccttcctg gaatagacac ttattctcga tatgggtttg tctatcctgc | 3660 |
| aggcaatgct tctgccagga gtaccatctg tggactcatg gaaagcctta tccaccatca | 3720 |
| tggcattcca cacagcattg cctctaaaca aggcacttat tttatagcta aggaagtgtg | 3780 |
| gcagtgggct catgctcatg gaattcactg attgtatctt gttgcccatt atcttaaagc | 3840 |
| agctggattg atagaacagt ggaaaggcca tttgaaatca caattacacc accaactagg | 3900 |
| tgacaatact ttgcagggct cggcaaagtt ctcttgaagg ctgagtatgt cctgaatcag | 3960 |
| catccaatat atggtactgt ttccctcata gccagcattc acaggcctaa gaatcaaggg | 4020 |
| gtagaagtag aagtggcacc actcaccatc actcctagtg acccactagc aaaaattta | 4080 |
| cttccagttc ccccaacatt atgttctgct ggccttagtt ccagagggaa gaattctgcc | 4140 |
| accagtcgac acaagaatga taccattaaa ctgaaagtta aaattgccac ctggccactt | 4200 |
| tgggctcctc ccacctctaa gtcaacaggt caagaaagga gttacagtgt tgacttgggt | 4260 |
| gattgacctg gactatcaag atgaaatcag gttactactc cacagtggag gtaaggaaga | 4320 |
| atatgtgtgg aatacaggag atcccttagg ccgtctttta gtactaccat gccctgtgat | 4380 |
| taaggtcagt ggaaaactac aacaatccaa tctaggcagg actacaaatg cccagactc | 4440 |
| ttcaggaatg aagggttggg tgacttcacc aggtaaaaaa ataacagcct gctgaggtgc | 4500 |
| tagctgaagg caaagggaat acagaatggt tagtagaaaa aggtagtcat caataccagc | 4560 |
| tatgaccaca agaccagttg cagaaatgag acctgtaatt gtcatgtgga tttcctcctt | 4620 |
| acatgtttgt gcatgtatac acttctacta agaaaatacc tttatttatt tcctttgctt | 4680 |
| ttcccttatc aagtgacatt attaacttca tatcagcagt taagtgttat taactttatg | 4740 |
| taatagcatt tcgttaaata attcacttct ggttgtatga aggatagccg tattaagtta | 4800 |
| ggtgtaatta tgacatcatt attgtcttta tttgaagatt atgtgtaatt tcaggagatg | 4860 |
| tgtatgggtt caagttgaca agggatggac ttgtgatggc taatgttgag tgtcaacttg | 4920 |
| actgaggatg caaagtattg ttcctgggtg tgtctgtgag ggtgttgcca aaggagatta | 4980 |
| acatttgtgt cagtgaactg ggagatgcag acccacccgc aatctgggtg agcaccatgt | 5040 |
| aatcagctgc cagagcagct agaataaa | 5068 |

<210> SEQ ID NO 10
<211> LENGTH: 535
<212> TYPE: DNA
<213> ORGANISM: Homo sapiens

<400> SEQUENCE: 10

| | |
|---|---|
| gcaacccct tgggtcccc ttcccttgta tgggagctct gttttcactc tatttcactc | 60 |
| tattaaatct tgcaactgca ctcttctggt ccatgtttgt tacggctcga gctgagcttt | 120 |
| ggctcgccat ccaccactgc tgtttgccgc cgtcgcacac tgctgctga ctcccatccc | 180 |
| tccggatcca gcagggtgtg tccgctgtgc tcctgatcca gcgaggtgcc cattgccgct | 240 |
| cctgattgga ctaaaggctt gccattgttc ctgcacggct aagtgcccgg ttcgtcccta | 300 |
| atccagctga acactagtca ctgggttcca cggttctctt ccttgaccca cggcttctaa | 360 |
| tagagctata acactcaccg catggcccaa gattccattc cttggaatct gtgaggccaa | 420 |
| gaaccccagg tcagagaaca cgaggcttgc caccatcttg gaagcggcct gccaacatct | 480 | tggaagtggc tcgccaccat cttgggagct ctgtgagcaa ggacccctgg taaca         535

<210> SEQ ID NO 11
<211> LENGTH: 6905
<212> TYPE: DNA
<213> ORGANISM: Homo sapiens

<400> SEQUENCE: 11
gctaccctct tgggtcccc tccctttgta tgggagctct gttttcactc tattcaatct         60
tgcaactgca ctcttctggt ccgtgtttgt tacagcttga gctgagcttt cgctcgcctt        120
ccaccactgc tgtttgccgc catcgcagac ctgccgtgct gacttccatc cctctagatc        180
tggcagggtg tccgctgtgc tcttgatcca gcgaggcgcc cattgccgct cccgattggg        240
ctaaaggctt gcaattgttc ctgcacgcta agtgcctggg ttcatcctca tcaagctggg        300
ttccacggtt ctcttcatga cccgcagctt ctaacagagc tataaaactc tgtgcatggc        360
ccaagattcc attccttgga atctgtgagg ccaagaaccc caggtcagag aacaggaggc        420
ttgccaccat cttggaagtg gctcgccacc atcttaggag ctctgtgagc ggagaccccc        480 acccccggt aacattttgg cgaccacgaa gggacctcca aagcggtgag taatattgga        540
tcactttcgc ttgctattct gtcctatcct tctttagaat tggaggaaaa tactgggcac        600
ctgtcggcca gttaaaaaca attagcgtgg ctgcccgact taagactcag gtgtgaggct        660
atctggggaa gggctttcta acaaccccca accttctgg gttggggacg ttggtctgcc        720
ccttccactt tcaattttct tggggaagcc aagggtcgac tagaggcaga aagctgtcgt        780
ccggaactcc tggcagtagc cggttgagat catggcgcag ccagaagtct ctactcaaca        840
gtcgcccatg cgtgcgctcc tacctttcct cctgacccat acctcctggg tcccgacgat        900
gactttcttg aaagtgtagc cccaaaattc tgcttacctc tgaatctact tccctgatc        960 cctggctcct aggtactaat ggttcagttt catttcctct agcaagttgt atctccaaag       1020
ggatctaagg aagctctacg ctgcgtcctt aggcatctag gctataaacc caggaagtct       1080
tgtccctggt gtccctcccg atttaggcat acagctctcg acatgggcag ttatgtggga       1140
cccgttcccc atcacccttg tcaaggcccc aagtttgtaa tggctaagag gagagagaga       1200
gaaagagaga gagacggagg ggagagagag agagagagat ggaggggaga gagagagaga       1260
gagacggagg ggagagagag agagagagag agacggaggg gagagagaga gagacggagg       1320
ggagagagag agagatggag gagagaaaga caagggagt caaagagaaa agaaagaga       1380 aagacagaaa tggtaaaaca aacaaaaaac agcgtgccct attcctttaa aagccggggt       1440
aaatttaaaa cctataattg ataattgaag gtcttctcca tgaccctata atactccaat       1500
actaccttgt tgtcagtgta aacaagggcg tagcctgaaa acactgagac cactgacaac       1560
ctgcagcttt cctatcaaaa aatccttaac ccagtaaccg gcagatgcat tcaatctgta       1620
gcagcaactg ttttgctaac agaagaaagt agaaagtaa cttttagagg aaacctcatt       1680
gtgagcacac cttaccagtt cagaattatt ctaagtcaaa aaagcaaaaa ggtagcttac       1740
taactcaaaa atcttaaagt atggggctat tgtgtttaaa aaaaaaaaaa ggtaatttaa       1800
caccaaccac tgataattct cttacccag caggtttcct aacaggggat ttaaatctta       1860
attaccatac aaaggtctga ccacacctag gaggaactcc cttcaggaca ggactataga       1920
gggttcctcc caggtgattg aggaaaaaac cacagtgggt attcagtaat tgataggag       1980 actcttgtgg aagcagagtt agaaaaattg cctaataaat ggtgtcctca aaagtgtgag       2040

```
ctgtttgcac tcagccaagc cttaaagtac ttacagaatc gtaaaaacta tctcaatcct    2100
gactcaaaag tttacttaca ccctctctga aatgaattta cataagaact gcttttttgg    2160
gaatgcatct tgatggggca gctgggtggt tatgaaatac tcaggaaacc agcccagctc    2220
taggacacat ccctgagcac aaaggcaatg ttgggcacgc tggtaaagga ccactagaat    2280
ccagcagcct ggactccttt ctttgtggtc aagaaaggca ggaaaacagg tgcaggactg    2340
ctacatcagt gagcataact aatctgataa gcagagggcc ttgggtggtt acacaccctg    2400
gaaaggaatt caactctgag cgcaaaggca atgttgggca cattggtaaa ggaccactag    2460
aatccagcag cccaggcccc tttctttatg gtcaagaaag cgggaaaag gggtgcagga    2520 ctgttacctc ggtgagcgta actaatccga taagcagagg tccatgggtg attacgcacc    2580
ctgaaaagaa taagcattag gcccttaaag gatgctctag gactaatgct cattggaaaa    2640
tgactagggg tgctggcatc cctatgttct tttctcagac gggaaatgtt ctccaccctc    2700
cccaaggcaa aaacacccct aagatgtatt ctggagaatt gggaccaatt tgaccccag     2760 acgctaagaa agagatgact tatgttcttc tgcagtacca cctggccacg atatcctctt    2820 caaggggggag aaacctggcc tcctgaggga agtataaatt ataacaccat cttacagcta   2880
gacctcttct gtagaaagga gggcaaatgg agtgaagtgc catatgtgca aactttcttt    2940
tcattaagag acaacttgca attatgtaag aagtgtgatt tatgccctac aggaagccct    3000
cagagtctac ctccctaccc cagcatcccc ctgactcctt ctccaactaa taggaaccc     3060 ccttcaaccc aaacggtcca aaaggagata gacaaggggg taaacaatga accaaagcgt    3120
gccaatgttc cctgattatg ccccctctaa gcagtgggag gaggagaatt tggcccagcc    3180
agtgtgcatg tgccttttc tctctcagac ttaaagcaaa ttaaaatagca cctaggtaaa    3240 ttctcagata accctgatgg ctatattgat gttttataag ggttaggata atcctttgat    3300
ctgacatgga gagatataat gttactgcta gatcagacac taacccccaaa tgagacaagt   3360 gccgccataa ctgcagcctg agagtttggc gatctctggt atctcactcg ggtcaatgat    3420
aggaggacaa cagaggaaag agaatgattc cccacagacc agcaggcagt tcccagtgta    3480
gaccctcact gggacacaga atcagaacat ggacattggt gctgcagaca tttgctaact    3540
tacatgctag aaggactaag gaaaactagg aagaagccta cgaattattc aatgatgtcc    3600
actataacac agggaaagga agaaaatcct actgcctttc tggagcgact aagggaggca    3660
ttgaggaagc atacttccct gtcacctgac tctattgaag gccaactaat cttaaaggat    3720
aagtttatca ctcagtcagc tgaagacatt aggaaaaaac ttcaaaagtc tgccttaggc    3780
ccagagcaaa acttagaaac cccattgaac ttggcaacct cggttttta taatagagat    3840 caggaggagc aggcggaaca ggacaaacgg ggtaaaaaaa aggccaccgc tttagttatg    3900
gccctcaggc aagtggactt tggaggctct ggaaaaggga aaagctgggc aaatcgaatg    3960
cctactaggg cttgcttcca gagtggtcta caaggacact ttgaaaaaga ttgtccaagt    4020
agaaataagt cgccccttcg tccatgcccc ttatatcaag ggaatcactg gaaggcccac    4080
tatcccaggg gacaaatgtc ctctgagtca gaagccacta accagatgat ccagcagcag    4140
gactgagggt gcccagggca agcactagcc catgccgtca ccctcacaga gccccaggta    4200
tgcttgacca ttgagggcca ggaggttaac tgtctcctgg acactagcac ggccttctca    4260
gtcttactct cctttcccgg acaactgtcc tccagatctg tcactatccg agggttccta    4320
ggacagtcag tcactagata cttatcccag tcactaagtt gtgactggtg aactttactc    4380
ttttcacatg cttttctaat tatccctgaa agcaccactc ccttgttagg gcgagacatt    4440
```

```
ctagcaaaag cagggggccat tatacacctg aacataggag aaggaacacc tgtttgttgt    4500
cccctgcttg aggaaggaat taatcccgaa gtctgggcaa cagaaggaca atacggacga    4560
gcaaagaatg cctgtgctgt tcaagttaaa ctaaaggatt ccgcctcctt tccctaccaa    4620
aggcagtacc cccttagacc tgaggcccaa caaggactcc aaaagattgt taaggaccta    4680
aaagcccatg gctagtaaa accatgcaat agccctgca atactccaat tttaggagta     4740
cagaaaccca acagacagtg gaggttagtg caagatctca ggattatcat tgaggctgtt    4800
gttcctgtat agccagctgt acctaaccct tatactctgc tttcccaaat accacaggaa    4860 gcagagggggt ttacagtccg gggccttaag gacacctttt tctgcatccc tgtatatcct    4920
gactctcaat tcttgtttgc ctttgaagat ccttcaaact caacgtctca actcacctgg    4980
aatgttttac cccaagggtt cagggatagc ccccattagc ccaagacttg agccagttct    5040
tatacctgga cactcttgtc ctttggtacg tggatgattt acttttagcc acctgttcag    5100
aaaccttgtg ccatcaagcc acccaagcac tcttttaattt cctcgccacc tgtggctaca    5160
ggtttccaaa ccaaaggctc agctctgctc acagcaattt aaatgcttag ggctaaaatt    5220
atccaaaggc accagggccc tcagtgagga aagtatccgg cctatactgg cttatcctca    5280
tcccaaaacc ctaaagcaac taagagtgtt ccttggcata acgggtttct gccgaatatg    5340
gattcccagg tacagcgaaa tagccagacc attatataca ctaattaagg aaactcagaa    5400
agccaatacc catttggtaa gatggacacc tgaagcagaa gcagatttcc aggccctaaa    5460
gaaggccctg acccaagccc cagtgttaag cttgccaatg gggcaagact ttctctttata    5520 tgtcacagaa aaaacaggaa tagctccagg agtccttacg cagatccaag ggacgagcct    5580
gcaacccatg gcatacctga gtaaggaaat tagtggcaaa gggttggcct cattgtttat    5640
gggtagtggc agcagtcaca gtcttagtaa ctgaagcagt taaaatgata caaggaagag    5700
atcttactgt gtggacatct catgatgtga atggcatact cactgctaaa ggagacttgt    5760
gactgtcaga caactgtttta cttaaatatc aggctctatt acttgaaggg ccagtgttgc    5820
gactgtgcac ttgtgcaact cttaacccag ccacattgct tccagacaat gaagaaaaga    5880
tagaacataa ctgtcaacaa ataattgctc aaacctacac tgctcgaggg gaccttttag    5940
aagttccctt gactgatccc gatctcaact tgtatactga tggaagttcc tttgcagaaa    6000
aaggacttca aaaggcggtg tatgcagtag tccttcaaaa tcgaagagct ttagaattgc    6060
taatcactga gagagggga acgtttttat ttttagggga agaatgctgt tattatgtta    6120
atcaattcgg aatcatcacc aagaaagtta aagaaattca agatcgaata caacgtagaa    6180
cagaggagct taaaaacac tggaccctgg ggcctcctca gccaatggat gccctggatt    6240 ctcccctttct taggacctct agcagctata tttctactcc tctttggacc ctgtatcttt    6300
aacctccgtg ttaagtttgt ctcttccaga atcgaagatg taaaactaca aatcgttctt    6360
caaatggacc cccagatgca gtccatgact aagatctact gaggacccct ggaccagcct    6420
gctagcccat gctccaatgt taatgacatt gaaggcaccc ctcccaagga aatctcaact    6480
gcacaacccc tactatgctc caattcagca ggaagcagtt acagtggtcc tcggccaacc    6540
tccccaacag catttgtatt ttcctgttgg gagggggcac tgagagacag gactagctgg    6600
atttcctagg ctgactgaga atccctaagc ctagctggga aggtgaccac ttccaccttt    6660
aaacacaggg cttgcaactt agctcacacc ctaccaattg gatagtaaag agaggtcact    6720
aaaatgctaa ttaggcaaaa acaggaggta aagaaatagc caatcatcca ttgcctgaga    6780
```

| | | |
|---|---|---|
| gcacagcggg agggacaatg accaggatat aaacccaggc attccagcct gcaacggcaa | 6840 |
| ccccctttgg gtcccctctc tttgtatggg agctctgttt tcactctatt caatcttgca | 6900 |
| actgc | 6905 |

<210> SEQ ID NO 12
<211> LENGTH: 9565
<212> TYPE: DNA
<213> ORGANISM: Homo sapiens

<400> SEQUENCE: 12

| | |
|---|---|
| gcagcccccc tttgggtccc ttccctttgt atgggagctg ttttcatgct atttcactct | 60 |
| attaaatctt gcaactgcac tcttctggtc catgtttctt acggctcgag ctgagctttt | 120 |
| gctcaccgtc caccactgct gtttgccacc accgcagacc tgccgctgac tcccatccct | 180 |
| ctggatcctg cagggtgtcc gctgtgctcc tgatccagcg aggcgcccat tgccgctccc | 240 |
| aattgggcta aaggcttgcc attgttcctg cacggctaag tgcctgggtt tgttctaatt | 300 |
| gagctgaaca ctagtcactg ggttccatgg ttctcttctg tgacccacgg cttctaatag | 360 |
| aactataaca cttaccacat ggcccaagat tccattcctt ggaatccgtg aggccaagaa | 420 |
| ctccaggtca gagaatacga ggcttgccac catcttggaa gcggcctgct accatcttgg | 480 |
| aagtggttca ccaccatctt gggagctctg tgagcaagga ccccccggta acattttggc | 540 |
| aaccacgaac ggacatccaa agtggtgagt aatattggac cactttcact tgctattctg | 600 |
| tcctatcctt ccttagaatt ggaggaaaat accgggcact tgtcggccag ttaaaaacga | 660 |
| ttagtgtggc caccggactt aagactcagg tgtgaggcta tctggggaag ggctttctaa | 720 |
| caaccccaa cccttctggg ttggggactt ggtttgcctc aagccagctt ccactttcag | 780 |
| ttttcttggg gaagccgagg gccgactaga ggcagaaagc tgtcgtcctg aactcccggc | 840 |
| agtagccggt tgagatcatg gtgtagccag aagtctcaac agtcgcccat gcatgcaccc | 900 |
| ctatcttttcc ttctgaccca tacctcctgg gtcccaacca caactttctt caaagtgtag | 960 |
| ccccaaaatt ctccttacct ctgaatatac ttcctctgat ccctgcctcc taggtactat | 1020 |
| tggttcagac ttccattcc tctagcaagt tgtatctcca aagggatcta aggaagctct | 1080 |
| gcgctgcgtc cttaggcacc taggctataa cccagggagt cttatccctg gtgtccctcc | 1140 |
| caatttaggc atacagctct tgacatgggc agttatgtag gacccactcc ccaccaccct | 1200 |
| tgccagggcc ccaagtttgt aaatggctga gggaaaagag agacagagga gagagagaga | 1260 |
| aatggaggag aaagagagag agacagagag gagagagaga cagtgagaga gacagaagag | 1320 |
| agagagagac aaagaggaga gagagagagt caaagagaga agaaagagag aagaaatagt | 1380 |
| aaaaaacagt gtgccctatt cctttaaaag ccagggtaaa tttaaaacct gtacttgata | 1440 |
| attgaaggtc ttctctgtga ccctatagca ctccaatcca ctttgtggtc agtgtaaata | 1500 |
| agagcatagg ccgaaagcac tgaggccatt gacaacccgt agcttccta tcaaaaatcc | 1560 |
| ttaacccagt aacccgcaga tggaccaaat gcattcagtc ggtagcgcaa ctgctttgct | 1620 |
| aaaagtagaa aagtaacttt tagaggaaac ctcattgtga gcacacctca cctgttcaga | 1680 |
| attattctaa taaaaaagc aaaaaggtag cttactaact caaaaatctt aaagtatggg | 1740 |
| gctattctgt tagaaaaagg taatgtaact ccaaccactg ataattccct taacccagca | 1800 |
| gatttcctaa cgggatttaa atcttaatta ccatacaaag gtccgaccag acctaggcgg | 1860 |
| aactcccttc aggacaggac gatagatggt tcctcccagg tgattgagga aaaaaaccac | 1920 |
| aatgggtatt cagtaattga tacggggact cttgtggaag cagagttaga aaaattgcct | 1980 |

```
aataactggt ctcctcaaac gtgtgagctg tttgcactca gccaagcctt aaagtactta    2040
cagaatcaaa agactatctc aatcctgatt caaaaggtta gctacaccct ctctgtaatg    2100
catttgcata agaacttgtt tatgggaatg catcttgatg gggcagctgg gttgttataa    2160
aataggaacc cagcccagct ctaggactca ccctgagcg caaaggcaat gttgggcatg     2220
ctggtaaagg accactagaa tccagcagcc cagaccctt tctttgtggt caagaaaggc    2280
gggaaaaggg gtgcaggact gctacatcgg taagcataac taatccgata aacgagggtc   2340
catgggtggt tacgcaccct ggaaaggaac tcacccctga gcacaaaggc aatgttgggc   2400
acgctggtaa aggaccacta gaatccagca gcctggaccc ctttctttgt ggtcaagaga   2460
ggcaggaaaa caggtgcagg actgcaacat cagtgagcat aactaattcg ataagcagag   2520
gtccatgggt ggtgatgcac cctggaaaga ataagcatta ggaccataga ggacactcca   2580
ggactaaagc tcatcggaaa atgactaggg ttgctggcat ccctatgttc ttttttcaga   2640
tgggaaacgt tccccgcaag acaaaaacgc ccctaagacg tattctggag aattgggacc   2700
aatttgaccc tcagacacta agaagaaac gacttatatt cttctgcagt gccgcctggc   2760
actcctgagg gaagtataaa ttataacacc atcttacagc tagacctctt ttgtagaaaa    2820
ggcaaatgga gtgaagtgcc ataagtacaa actttctttt cattaagaga caactcacaa    2880
ttatgtaaaa agtgtgattt atgccctaca ggaagccttc agagtctacc tcccatccc    2940 agcatccccg actccttccc caactaataa ggaccccct tcaacccaaa tggtccaaaa    3000
ggagatagac aaaagggtaa acagtgaacc aaagagtgcc aatattcccc aattatgacc   3060
cctccaagca gtgggaggaa gagaattcgg cccagccaga gtgcatgtgc ctttttctct   3120
cccagactta aagcaaataa aaacagactt aggtaaattc tcagataacc ctgatggcta   3180
tattgatgtt ttacaagggt taggacaatt ctttgatctg acatggagag atataatgtc   3240
actgctaaat cagacactaa ccccaaatga gagaagtgcc accataactg cagcctgaga   3300
gtttggcgat ctctggtatc tcagtcaggt caatgatagg atgacaacag aggaaagaga   3360
atgattcccc acaggccagc aggcagttcc cagtctagac cctcattggg acacagaatc   3420
agaacatgga gattggtgct gcagacattt gctaacttgt gtgctagaag gactaaggaa   3480
aactaggaag aagtctatga attactcaat gatgtccacc ataacacagg aagggaaga    3540 aaatcctact gcctttctgg agagactaag ggaggcattg aggaagcgtg cctctctgtc   3600
acctgactct tctgaaggcc aactaatctt aaagcgtaag tttatcactc agtcagctgc   3660
agacattaga aaaaaacttc aaaagtctgc cgtaggcccg gagcaaaact tagaaaccct   3720
attgaacttg gcaacctcgg ttttttataa tagagatcag gaggagcagg cggaacagga   3780
caaacgggat taaaaaaaag gccaccgctt tagtcatgac cctcaggcaa gtggactttg   3840
gaggctctgg aaaagggaaa agctgggcaa attgaatgcc taatagggct tgcttccagt   3900
gcggtctaca aggacacttt aaaaaagatt gtccaagtag aagtaagccg ccccctcgtc   3960
catgcccctt atttcaaggg aatcactgga aggcccactg ccccagggga caaaggtcct   4020
ctgagtcaga agccactaac cagatgatcc agcagcagga ctgagggtgc ctggggcaag   4080
cgccatccca tgccatcacc ctcacagagc cctgggtatg cttgaccatt gagggccagg   4140
aggttgtctc ctggacactg gtgcggtctt cttagtctta ctcttctgtc ccggacaact   4200
gtcctccaga tctgtcacta tctgaggggg tcctaagacg ggcagtcact agatacttct   4260
cccagccact aagttatgac tggggagctt tattcttttc acatgctttt ctaattatgc   4320
```

```
ttgaaagccc cactaccttg ttagggagag acattctagc aaaagcaggg gccattatac    4380
acctgaacat aggagaagga acacccgttt gttgtcccct gcttgaggaa ggaattaatc    4440
ctgaagtctg ggcaacagaa ggacaatatg gacgagcaaa gaatgcccgt cctgttcaag    4500
ttaaactaaa ggattccacc tcctttccct accaaaggca gtaccccctc agacccaagg    4560
cccaacaagg actccaaaag attgttaagg acctaaaagc ccaaggccta gtaaaaccat    4620
gcagtaaccc ctgcagtact ccaattttag gagtacagaa acccaacaga cagtggaggt    4680
tagtgcaaga tctcaggatt atcaatgagg ctgttgttcc tctatagcca gctgtaccta    4740
gcccttatac tctgctttcc caaataccag aggaagcaga gtggtttaca gtcctggacc    4800
ttcaggatgc cttcttctgc atccctgtac atcctgactc tcaattcttg tttgcctttg    4860
aagatacttc aaacccaaca tctcaactca cctggactat tttacccccaa gggttcaggg   4920
atagtcccca tctatttggc caggcattag cccaagactt gagccaatcc tcatacctgg    4980
acacttgtcc ttcggtaggt ggatgattta cttttggccg cccattcaga aaccttgtgc    5040
catcaagcca cccaagcgct cttcaatttc ctcgctacct gtggctacat ggtttccaaa    5100
ccaaaggctc aactctgctc acagcaggtt acttagggct aaaattatcc aaaggcacca    5160
gggcccctcag tgaggaacac atccagccta tactggctta tcctcatccc aaaaccctaa    5220
agcaactaag gggattcctt ggcgtaatag gtttctgccg aaaatggatt cccaggtatg    5280
gcgaaatagc caggtcatta aatacactaa ttaaggaaac tcagaaagcc aatacccatt    5340
tagtaagatg gacaactgaa gtagaagtgg cttttccaggc cctaacccaa gccccagtgt    5400
taagtttgcc aacagggcaa gacttttctt catatgtcac agaaaaaaca ggaatagctc    5460
taggagtcct tacacagatc cgagggatga gcttgcaacc tgtggcatac ctgactaagg    5520
aaattgatgt agtggcaaag ggttgacctc attgtttacg ggtagtggtg gcagtagcag    5580
tcttagtatc tgaagcagtt aaaataatac agggaagaga tcttactgtg tggacatctc    5640
atgatgtgaa tggcatactc actgctaaag gagacttgtg gctgtcagac aactgtttac    5700
ttaaatgtca ggctctatta cttgaagggc cagtgctgcg actgtgcact tgtgcaactc    5760
ttaacccagc cacatttctt ccagacaatg aagaaaagat aaaacataac tgtcaacaag    5820
taatttctca aacctatgcc actcgagggg acctttagga ggttcctttg actgatcccg    5880
acctcaactt gtatactgat ggaagttcct ttgtagaaaa aggacttcga aaagtggggt    5940
atgcagtggt cagtgataat ggaatacttg aaagtaatcc cctcactcca ggaactagtg    6000
ctcagctagc agaactaata gccctcactt gggcactaga attaggagaa gaaaaaaggg    6060
caaatatata tacagactct aaatatgctt acctagtcct ccatgcccat gcagcaatat    6120
ggaaagaaag ggaattccta acttctgaga gaacacctat caaacatcag gaagccatta    6180
ggaaattatt attggctgta cagaaaccta agaggtggc agtcttacac tgccggggtc    6240
atcagaaagg aaaggaaagg gaaatagaag agaactgcca agcagatatt gaagccaaaa    6300
gagctgcaag gcaggaccct ccattagaaa tgcttataaa acaaccccta gtatagggta    6360
atcccctccg ggaaaccaag ccccagtact cagcaggaga acagaatggg gaacctcac    6420
gaggacagtt ttctcccctc gggacggcta gccactgaag aagggaaaat acttttgcct    6480
gcaactatcc aatggaaatt acttaaaacc cttcatcaaa cctttcactt aggcatcgat    6540
agcacccatc agatggccaa atcattattt actggaccag gccttttcaa aactatcaag    6600
cagatagtca gggcctgtga agtgtgccag agaaataatc ccctgcctta tcgccaagct    6660
ccttcaggag aacaaagaac aggccattac cctggagaag actggcaact gattttaccc    6720
```

```
acaagcccaa acctcaggga tttcagtatc tactagtctg ggtagatact ttcacgggtt    6780
gggcagaggc cttcccctgt aggacagaaa aggcccaaga ggtaataaag gcactagttc    6840
atgaaataat tcccagattc ggacttcccc gaggcttaca gagtgacaat agccctgctt    6900
tccaggccac agtaacccag ggagtatccc aggcgttagg tatacgatat cacttacact    6960
gcgcctgaag gccacagtcc tcagggaagg tcgagaaaat gaatgaaaca ctcaaaggac    7020
atctaaaaaa gcaaacccag gaaacccacc tcacatggcc tgctctgttg cctatagcct    7080
taaaaagaat ctgcaacttt ccccaaaaag caggacttag cccatacgaa atgctgtatg    7140
gaaggcccct cataaccaat gaccttgtgc ttgacccaag acagccaact tagttgcaga    7200
catcacctcc ttagccaaat atcaacaagt tcttaaaaca ttacaaggaa cctatccctg    7260
agaagaggga aaagaactat tccacccttg tgacatggta ttagtcaagt cccttccctc    7320
taattcccca tccctagata catcctggga aggaccctac ccagtcattt tatctacccc    7380
aactgcggtt aaagtggctg gagtggagtc ttggatacat cacacttgag tcaaatcctg    7440
gatactgcca aaggaacctg aaaatccagg agacaacgct agctattcct gtgaacctct    7500
agaggatttg cgcctgctct tcaaacaaca accaggagga aagtaactaa aatcataaat    7560
ccccatggcc ctcccttatc atattttttct ctttactgtt cttttaccct ctttcactct    7620
cactgcaccc cctccatgcc gctgtatgac cagtagctcc ccttaccaag agtttctatg    7680
gagaatgcag cgtcccggaa atattgatgc cccatcgtat aggagtcttt ctaagggaac    7740
ccccaccttc actgcccaca cccatatgcc ccgcaactgc tatcactctg ccactctttg    7800
catgcatgca aatactcatt attggacagg aaaaatgatt aatcctagtt gtcctggagg    7860
acttggagtc actgtctgtt ggacttactt cacccaaact ggtatgtctg atgggggtgg    7920
agttcaagat caggcaagag aaaaacatgt aaaagaagta atctcccaac tcacccgggt    7980
acatggcacc tctagcccct acaaaggact agatctctca aaactacatg aaaccctccg    8040
tacccatact cgcctggtaa gcctatttaa taccaccctc actgggctcc atgaggtctc    8100
ggcccaaaac cctactaact gttggatatg cctcccctg aacttcaggc catatgtttc    8160
aatccctgta cctgaacaat ggaacaactt cagcacagaa ataaacacca cttccgtttt    8220
agtaggacct cttgtttcca atctggaaat aacccatacc tcaaacctca cctgtgtaaa    8280
atttagcaat actacataca caaccaactc ccaatgcatc aggtgggtaa ctcctcccac    8340
acaaatagtc tgcctaccct caggaatatt ttttgtctgt ggtacctcag cctatcgttg    8400
tttgaatggc tcttcagaat ctatgtgctt cctctcattc ttagtgcccc ctatgaccat    8460
ctacactgaa caagatttat acagttatgt catatctaag ccccgcaaca aaagagtacc    8520
cattcttcct tttgttatag gagcaggagt gctaggtgca ctaggtactg gcattggcgg    8580
tatcacaacc tctactcagt tctactacaa actatctcaa gaactaaatg gggacatgga    8640
acgggtcgcc gactccctgg tcaccttgca agatcaactt aactccctag cagcagtagt    8700
ccttcaaaat cgaagagctt tagacttgct aaccgctgaa agaggggaa cctgtttatt    8760 tttaggggaa gaatgctgtt attatgttaa tcaatccgga atcgtcactg agaaagttaa    8820
agaaattcga gatcgaatac aacgtagagc agaggagctt cgaaacactg gaccctgggg    8880
cctcctcagc caatggatgc cctggattct ccccttctta ggacctctag cagctataat    8940
attgctactc ctctttggac cctgtatctt taacctcctt gttaactttg tctcttccag    9000
aatcgaagct gtaaaactac aaatggagcc caagatgcag tccaagacta agatctaccg    9060
```

```
cagacccctg gaccggcctg ctagcccacg atctgatgtt aatgacatca aaggcacccc    9120
tcctgaggaa atctcagctg cacaacctct actacgcccc aattcagcag gaagcagtta    9180
gagcggtcgt cggccaacct ccccaacagc acttaggttt tcctgttgag atgggggact    9240
gagagacagg actagctgga tttcctaggc tgactaagaa tccctaagcc tagctgggaa    9300
ggtgaccaca tccaccttta aacacggggc ttgcaactta gctcacacct gaccaatcag    9360
agagctcact aaaatgctaa ttaggcaaag acaggaggta agaaatagc caatcatcta     9420 ttgcctgaga gcacagcagg agggacaatg atcgggatat aaacccaagt cttcgagccg    9480
gcaacggcaa cccccttggg gtcccctccc tttgtatggg agctctgttt tcatgctatt    9540
tcactctatt aaatcttgca actgc                                          9565
```

<210> SEQ ID NO 13
<211> LENGTH: 543
<212> TYPE: DNA
<213> ORGANISM: Homo sapiens

<400> SEQUENCE: 13

```
atgacaacag aagaaagaaa acaattcccc acaggccagc aggcagttcc cagcgtagac      60
cttcattggg acacagaatc agaacatgga gattggtgcc gcagacattt actaacttgc     120
gcgctagaag cactaaggaa aactaggaag aagcctatga attattcaat gatgtccact     180
ataacacagg gaaaggaaga aaatcctact gcctttctgg agagactaag ggaggcattg     240
agaaagcata cctctctgtc acctgactct attgaaggcc aactaatctt aaaggataag     300
ttttccactc agtcagctgc agacattaga aaaaaacttc aaaagtctgc gttaggccgg     360
gagcaaaact tagaaacccct attgaacttg gcaacctcag ttttttatga tagagatcag    420
gaggatcagg tggaatggac aaatgagatt ttaaaaaaag gccaccactt tagtcatggc    480
cctcaggcaa gcagactttg gacactctgg aaaagggaaa agctgggcaa atcgaatgcc    540
taa                                                                   543
```

<210> SEQ ID NO 14
<211> LENGTH: 180
<212> TYPE: PRT
<213> ORGANISM: Homo sapiens

<400> SEQUENCE: 14

```
Met Thr Thr Glu Glu Arg Lys Gln Phe Pro Thr Gly Gln Gln Ala Val
  1               5                  10                  15

Pro Ser Val Asp Leu His Trp Asp Thr Glu Ser Glu His Gly Asp Trp
                 20                  25                  30

Cys Arg Arg His Leu Leu Thr Cys Ala Leu Glu Ala Leu Arg Lys Thr
             35                  40                  45

Arg Lys Lys Pro Met Asn Tyr Ser Met Met Ser Thr Ile Thr Gln Gly
         50                  55                  60

Lys Glu Glu Asn Pro Thr Ala Phe Leu Glu Arg Leu Arg Glu Ala Leu
 65                  70                  75                  80

Arg Lys His Thr Ser Leu Ser Pro Asp Ser Ile Glu Gly Gln Leu Ile
                 85                  90                  95

Leu Lys Asp Lys Phe Ser Thr Gln Ser Ala Ala Asp Ile Arg Lys Lys
                100                 105                 110

Leu Gln Lys Ser Ala Leu Gly Arg Glu Gln Asn Leu Glu Thr Leu Leu
            115                 120                 125

Asn Leu Ala Thr Ser Val Phe Tyr Asp Arg Asp Gln Glu Asp Gln Val
```

```
                    130                 135                 140
Glu Trp Thr Asn Glu Ile Leu Lys Lys Gly His His Phe Ser His Gly
145                 150                 155                 160

Pro Gln Ala Ser Arg Leu Trp Thr Leu Trp Lys Arg Glu Lys Leu Gly
                165                 170                 175

Lys Ser Asn Ala
            180

<210> SEQ ID NO 15
<211> LENGTH: 435
<212> TYPE: DNA
<213> ORGANISM: Homo sapiens

<400> SEQUENCE: 15
atgattcagc cccaggactc agggtgccca gggcaagcgc cagcctatgc catcaccctc      60
acagagccct gggtatgctt gaccattgag ggtcaggagg ttaactatct cctggacact     120
ggcgtggcct tctcagtctt actctcctgt cccggacaac tgtcctccag atctgtcact     180
atccgagggt ttctacgaca gccagccact agatacttct cccagccact aagttgtgac     240
tggggaactc tactcttttc acatgttttt ctaattatgc ctgaaagccc cactcctttg     300
ttagggaaag acattctagc aaaagcaggg gccattatac acctgaacat aggagaagga     360
acacctgttt gttgtcccct gcttgaagaa ggaattaatc ctgaagtctg acaacagaa      420 ggacaataca gatga                                                      435

<210> SEQ ID NO 16
<211> LENGTH: 144
<212> TYPE: PRT
<213> ORGANISM: Homo sapiens

<400> SEQUENCE: 16

Met Ile Gln Pro Gln Asp Ser Gly Cys Pro Gly Gln Ala Pro Ala Tyr
1               5                   10                  15

Ala Ile Thr Leu Thr Glu Pro Trp Val Cys Leu Thr Ile Glu Gly Gln
                20                  25                  30

Glu Val Asn Tyr Leu Leu Asp Thr Gly Val Ala Phe Ser Val Leu Leu
            35                  40                  45

Ser Cys Pro Gly Gln Leu Ser Ser Arg Ser Val Thr Ile Arg Gly Phe
50                  55                  60

Leu Arg Gln Pro Ala Thr Arg Tyr Phe Ser Gln Pro Leu Ser Cys Asp
65                  70                  75                  80

Trp Gly Thr Leu Leu Phe Ser His Val Phe Leu Ile Met Pro Glu Ser
                85                  90                  95

Pro Thr Pro Leu Leu Gly Lys Asp Ile Leu Ala Lys Ala Gly Ala Ile
            100                 105                 110

Ile His Leu Asn Ile Gly Glu Gly Thr Pro Val Cys Cys Pro Leu Leu
        115                 120                 125

Glu Glu Gly Ile Asn Pro Glu Val Trp Thr Thr Glu Gly Gln Tyr Arg
    130                 135                 140

<210> SEQ ID NO 17
<211> LENGTH: 312
<212> TYPE: DNA
<213> ORGANISM: Homo sapiens

<400> SEQUENCE: 17 atgcccccctc caggcagtgg gaggaggaga attcggccca gccagagtgc atgtaccttt      60
```

```
tttttttctct cagacttaaa gcaaattaaa atagacctag gtaaattctc agataaccct     120
gatggctata ttgatgtttt acaagggtta ggacaatcct ttgctctgac atggagagat     180
ataatgttac tgctaaatca gacactaacc ccaaatgaga gaagtgtcac catagctgca     240
gcccaagagt ttggcaatct ctggtatctc agtcaggtca atgataggat gacaacagag     300
gaaagggaat ga                                                         312
```

<210> SEQ ID NO 18
<211> LENGTH: 103
<212> TYPE: PRT
<213> ORGANISM: Homo sapiens

<400> SEQUENCE: 18

```
Met Pro Pro Pro Gly Ser Gly Arg Arg Ile Arg Pro Ser Gln Ser
1               5                   10                  15

Ala Cys Thr Phe Phe Leu Ser Asp Leu Lys Gln Ile Lys Ile Asp
                20                  25                  30

Leu Gly Lys Phe Ser Asp Asn Pro Asp Gly Tyr Ile Asp Val Leu Gln
                35                  40                  45

Gly Leu Gly Gln Ser Phe Ala Leu Thr Trp Arg Asp Ile Met Leu Leu
    50                  55                  60

Leu Asn Gln Thr Leu Thr Pro Asn Glu Arg Ser Val Thr Ile Ala Ala
65                  70                  75                  80

Ala Gln Glu Phe Gly Asn Leu Trp Tyr Leu Ser Gln Val Asn Asp Arg
                85                  90                  95

Met Thr Thr Glu Glu Arg Glu
            100
```

<210> SEQ ID NO 19
<211> LENGTH: 207
<212> TYPE: DNA
<213> ORGANISM: Homo sapiens

<400> SEQUENCE: 19

```
atgggcagtt atgtaggacc cattccccac cacacttgcc agggccccaa gtttgtaatg      60
gctaagagag agacacagag agagagagag agatggagag agagacaagg agggagtcaa     120
agagaaaaag aaagaaaaag aaatagtaga aaaaaaagtg tgccctattc ctttaaaagc     180
cagggtaaat ttaaaacctg taattga                                         207
```

<210> SEQ ID NO 20
<211> LENGTH: 68
<212> TYPE: PRT
<213> ORGANISM: Homo sapiens

<400> SEQUENCE: 20

```
Met Gly Ser Tyr Val Gly Pro Ile Pro His His Thr Cys Gln Gly Pro
1               5                   10                  15

Lys Phe Val Met Ala Lys Arg Glu Thr Gln Arg Glu Arg Glu Arg Trp
                20                  25                  30

Arg Glu Arg Gln Gly Gly Ser Gln Arg Glu Lys Glu Arg Lys Arg Asn
            35                  40                  45

Ser Arg Lys Lys Ser Val Pro Tyr Ser Phe Lys Ser Gln Gly Lys Phe
    50                  55                  60

Lys Thr Cys Asn
65
```

<210> SEQ ID NO 21
<211> LENGTH: 306
<212> TYPE: DNA
<213> ORGANISM: Homo sapiens

<400> SEQUENCE: 21

```
atgtcaagaa agaaacgact tatattcttc tgcagtactg cctggccacg atatcctctt      60
caagggggag aaacctggcc tcctgaggga agtacaaatt ataacaccat cttacagcta     120
gacctctttt gtagaaaaga aggcaaatgg agtgaagtgc catatgtgca aactttcttt     180
tcattaagag acaactcaca attatgtaaa aagtgtggtt tatgtcttac aggaagccct     240
cagagtctac ctccctatcc cagcattccc ccgactcctt ccccaactaa taagcaccac     300
ccttga                                                                306
```

<210> SEQ ID NO 22
<211> LENGTH: 101
<212> TYPE: PRT
<213> ORGANISM: Homo sapiens

<400> SEQUENCE: 22

```
Met Ser Arg Lys Lys Arg Leu Ile Phe Phe Cys Ser Thr Ala Trp Pro
1               5                   10                  15
Arg Tyr Pro Leu Gln Gly Gly Glu Thr Trp Pro Pro Glu Gly Ser Thr
            20                  25                  30
Asn Tyr Asn Thr Ile Leu Gln Leu Asp Leu Phe Cys Arg Lys Glu Gly
        35                  40                  45
Lys Trp Ser Glu Val Pro Tyr Val Gln Thr Phe Phe Ser Leu Arg Asp
    50                  55                  60
Asn Ser Gln Leu Cys Lys Lys Cys Gly Leu Cys Leu Thr Gly Ser Pro
65                  70                  75                  80
Gln Ser Leu Pro Pro Tyr Pro Ser Ile Pro Pro Thr Pro Ser Pro Thr
                85                  90                  95
Asn Lys His His Pro
            100
```

<210> SEQ ID NO 23
<211> LENGTH: 603
<212> TYPE: DNA
<213> ORGANISM: Homo sapiens

<400> SEQUENCE: 23

```
atgctagaag gactaaggaa aactaggaag aagcctacga attattcaat gatgtccact      60
ataacacagg gaaaggaaga aaatcctact gcctttctgg agcgactaag ggaggcattg     120
aggaagcata cttccctgtc acctgactct attgaaggcc aactaatctt aaaggataag     180
tttatcactc agtcagctga agacattagg aaaaaacttc aaaagtctgc cttaggccca     240
gagcaaaact tagaaacccc attgaacttg caacctcgg ttttttataa tagagatcag     300
gaggagcagg cggaacagga caaacggggt aaaaaaaagg ccaccgcttt agttatggcc     360
ctcaggcaag tggactttgg aggctctgga aagggaaaa gctgggcaaa tcgaatgcct     420
actagggctt gcttccagag tggtctacaa ggacactttg aaaaagattg tccaagtaga     480
aataagtcgc cccttcgtcc atgccccta tatcaaggga atcactggaa ggcccactat     540
cccaggggac aaatgtcctc tgagtcagaa gccactaacc agatgatcca gcagcaggac     600
tga                                                                   603
```

<210> SEQ ID NO 24
<211> LENGTH: 200
<212> TYPE: PRT
<213> ORGANISM: Homo sapiens

<400> SEQUENCE: 24

Met Leu Glu Gly Leu Arg Lys Thr Arg Lys Lys Pro Thr Asn Tyr Ser
1               5                   10                  15

Met Met Ser Thr Ile Thr Gln Gly Lys Glu Glu Asn Pro Thr Ala Phe
            20                  25                  30

Leu Glu Arg Leu Arg Glu Ala Leu Arg Lys His Thr Ser Leu Ser Pro
        35                  40                  45

Asp Ser Ile Glu Gly Gln Leu Ile Leu Lys Asp Lys Phe Ile Thr Gln
    50                  55                  60

Ser Ala Glu Asp Ile Arg Lys Lys Leu Gln Lys Ser Ala Leu Gly Pro
65                  70                  75                  80

Glu Gln Asn Leu Glu Thr Pro Leu Asn Leu Ala Thr Ser Val Phe Tyr
                85                  90                  95

Asn Arg Asp Gln Glu Glu Gln Ala Glu Gln Asp Lys Arg Gly Lys Lys
            100                 105                 110

Lys Ala Thr Ala Leu Val Met Ala Leu Arg Gln Val Asp Phe Gly Gly
        115                 120                 125

Ser Gly Lys Gly Lys Ser Trp Ala Asn Arg Met Pro Thr Arg Ala Cys
130                 135                 140

Phe Gln Ser Gly Leu Gln Gly His Phe Glu Lys Asp Cys Pro Ser Arg
145                 150                 155                 160

Asn Lys Ser Pro Leu Arg Pro Cys Pro Leu Tyr Gln Gly Asn His Trp
                165                 170                 175

Lys Ala His Tyr Pro Arg Gly Gln Met Ser Ser Glu Ser Glu Ala Thr
            180                 185                 190

Asn Gln Met Ile Gln Gln Gln Asp
        195                 200

<210> SEQ ID NO 25
<211> LENGTH: 1617
<212> TYPE: DNA
<213> ORGANISM: Homo sapiens

<400> SEQUENCE: 25
atggccctcc cttatcatat ttttctcttt actgttcttt taccctcttt cactctcact      60
gcaccccctc catgccgctg tatgaccagt agctcccctt accaagagtt ctatggaga     120
atgcagcgtc ccggaaatat tgatgcccca tcgtatagga gtctttctaa gggaaccccc     180
accttcactg cccacaccca tatgccccgc aactgctatc actctgccac tctttgcatg     240
catgcaaata ctcattattg gacaggaaaa atgattaatc ctagttgtcc tggaggactt     300
ggagtcactg tctgttggac ttacttcacc caaactggta tgtctgatgg gggtggagtt     360
caagatcagg caagagaaaa acatgtaaaa gaagtaatct cccaactcac ccgggtacat     420
ggcacctcta gcccctacaa aggactagat ctctcaaaac tacatgaaac cctccgtacc     480
catactcgcc tggtaagcct atttaatacc accctcactg ggtccatga ggtctcggcc      540
caaaacccta ctaactgttg gatatgcctc cccctgaact tcaggccata tgtttcaatc     600
cctgtacctg aacaatggaa caacttcagc acagaaataa acaccacttc cgttttagta     660
ggacctcttg tttccaatct ggaaataacc cataccctcaa acctcacctg tgtaaaattt    720

```
agcaatacta catacacaac caactcccaa tgcatcaggt gggtaactcc tcccacacaa    780
atagtctgcc taccctcagg aatatttttt gtctgtggta cctcagccta tcgttgtttg    840
aatggctctt cagaatctat gtgcttcctc tcattcttag tgcccccctat gaccatctac   900 actgaacaag atttatacag ttatgtcata tctaagcccc gcaacaaaag agtacccatt    960
cttccttttg ttataggagc aggagtgcta ggtgcactag gtactggcat tggcggtatc   1020
acaacctcta ctcagttcta ctacaaacta tctcaagaac taaatgggga catggaacgg   1080
gtcgccgact ccctggtcac cttgcaagat caacttaact ccctagcagc agtagtcctt   1140
caaaatcgaa gagctttaga cttgctaacc gctgaaagag ggggaacctg tttattttta   1200
ggggaagaat gctgttatta tgttaatcaa tccggaatcg tcactgagaa agttaaagaa   1260
attcgagatc gaatacaacg tagagcagag gagcttcgaa acactggacc ctggggcctc   1320
ctcagccaat ggatgccctg gattctcccc ttcttaggac tctagcagc tataatattg     1380 ctactcctct ttggaccctg tatctttaac ctccttgtta actttgtctc ttccagaatc   1440
gaagctgtaa aactacaaat ggagcccaag atgcagtcca agactaagat ctaccgcaga   1500
cccctggacc ggcctgctag cccacgatct gatgttaatg acatcaaagg caccctcct    1560 gaggaaatct cagctgcaca acctctacta cgccccaatt cagcaggaag cagttag      1617
```

<210> SEQ ID NO 26
<211> LENGTH: 538
<212> TYPE: PRT
<213> ORGANISM: Homo sapiens

<400> SEQUENCE: 26

```
Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220
```

```
Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
            245                 250                 255

Pro Pro Thr Gln Ile Val Cys Leu Pro Ser Gly Ile Phe Phe Val Cys
        260                 265                 270

Gly Thr Ser Ala Tyr Arg Cys Leu Asn Gly Ser Ser Glu Ser Met Cys
    275                 280                 285

Phe Leu Ser Phe Leu Val Pro Pro Met Thr Ile Tyr Thr Glu Gln Asp
290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
                340                 345                 350

Glu Leu Asn Gly Asp Met Glu Arg Val Ala Asp Ser Leu Val Thr Leu
            355                 360                 365

Gln Asp Gln Leu Asn Ser Leu Ala Ala Val Val Leu Gln Asn Arg Arg
370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
                420                 425                 430

Arg Asn Thr Gly Pro Trp Gly Leu Leu Ser Gln Trp Met Pro Trp Ile
            435                 440                 445

Leu Pro Phe Leu Gly Pro Leu Ala Ala Ile Ile Leu Leu Leu Leu Phe
450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
                500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
530                 535

<210> SEQ ID NO 27
<211> LENGTH: 18
<212> TYPE: DNA
<213> ORGANISM: Artificial sequence
<220> FEATURE:
<223> OTHER INFORMATION: Synthetic Construct - amplification primer

<400> SEQUENCE: 27
tgcagatgct gtgtctgg                                                 18

<210> SEQ ID NO 28
<211> LENGTH: 17
<212> TYPE: DNA
<213> ORGANISM: Artificial sequence
<220> FEATURE:
```

<223> OTHER INFORMATION: Synthetic Construct - amplification primer

<400> SEQUENCE: 28
cgtactggcc caggacc                                                              17

<210> SEQ ID NO 29
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 29
ggttcgtgct aattgagctg                                                           20

<210> SEQ ID NO 30
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 30
atggtggcaa gcttcttgtt                                                           20

<210> SEQ ID NO 31
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 31
tgagctttcc ctcactgtcc                                                           20

<210> SEQ ID NO 32
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 32
tgttcggctt gattaggatg                                                           20

<210> SEQ ID NO 33
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 33
catggcccaa tattccattc                                                           20

<210> SEQ ID NO 34
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 34
ggtccttgtt cacagaactc c                                                         21

<210> SEQ ID NO 35
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 35
ccgctcctga ttggactaaa                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 36
cgtgggtcaa ggaagagaac                                               20

<210> SEQ ID NO 37
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 37
atgacccgca gcttctaaca g                                             21

<210> SEQ ID NO 38
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 38
ctccgctcac agagctccta                                               20

<210> SEQ ID NO 39
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 39
ccaacatcac taacacaacc t                                             21

<210> SEQ ID NO 40
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 40
gggagttagt aagggGtttg                                               20

<210> SEQ ID NO 41
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 41
caacctatta aacaaaacta aatt                                          24

<210> SEQ ID NO 42
<211> LENGTH: 27
<212> TYPE: DNA
<213> ORGANISM: Artificial sequence
<220> FEATURE:
<223> OTHER INFORMATION: Synthetic Construct - amplification primer

<400> SEQUENCE: 42
agatttaata gagtgaaaat agagttt                                       27

<210> SEQ ID NO 43
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 43
ttattagttt agggatagt tg                                             22

<210> SEQ ID NO 44
<211> LENGTH: 23
<212> TYPE: DNA
<213> ORGANISM: Artificial sequence
<220> FEATURE:
<223> OTHER INFORMATION: Synthetic Construct - amplification primer

<400> SEQUENCE: 44
acacaataaa caacctacta aat                                           23

<210> SEQ ID NO 45
<211> LENGTH: 19
<212> TYPE: DNA
<213> ORGANISM: Artificial sequence
<220> FEATURE:
<223> OTHER INFORMATION: Synthetic Construct - amplification primer

<400> SEQUENCE: 45
gagggtaagt ggtgataaa                                                19

<210> SEQ ID NO 46
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 46
aacctactaa atccaaaaaa a                                             21

<210> SEQ ID NO 47
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 47
taggatttta ggtttattgt ta                                            22

<210> SEQ ID NO 48
<211> LENGTH: 19

```
<212> TYPE: DNA
<213> ORGANISM: Artificial sequence
<220> FEATURE:
<223> OTHER INFORMATION: Synthetic Construct - amplification primer

<400> SEQUENCE: 48
aaaaataaaa tattaaacc                                              19

<210> SEQ ID NO 49
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 49
atatgtggga gtgagagata                                             20

<210> SEQ ID NO 50
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 50
caacaacaaa caataataat aa                                          22

<210> SEQ ID NO 51
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 51
ttgagttttt ttattgatag tg                                          22

<210> SEQ ID NO 52
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 52
tctaaatcct attttcctac t                                           21

<210> SEQ ID NO 53
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 53 gttttttat tgatagtgag agat                                         24

<210> SEQ ID NO 54
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 54
```
taacaaacct ttaatccaat                                              20

<210> SEQ ID NO 55
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 55
tttagtgagg atgatgtaat at                                           22

<210> SEQ ID NO 56
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 56
caacttaata aaataaaacc ca                                           22

<210> SEQ ID NO 57
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 57
ataatgtttt agtaagtgtt ggat                                         24

<210> SEQ ID NO 58
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 58
acaattacaa acctttaacc                                              20

<210> SEQ ID NO 59
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 59
aattcattca acatccattc                                              20

<210> SEQ ID NO 60
<211> LENGTH: 26
<212> TYPE: DNA
<213> ORGANISM: Artificial sequence
<220> FEATURE:
<223> OTHER INFORMATION: Synthetic Construct - amplification primer

<400> SEQUENCE: 60
ggtttaatat tatttattat tttgga                                       26

<210> SEQ ID NO 61
<211> LENGTH: 25
<212> TYPE: DNA
<213> ORGANISM: Artificial sequence

```
<220> FEATURE:
<223> OTHER INFORMATION: Synthetic Construct - amplification primer

<400> SEQUENCE: 61
ctcttacctt cctatactct ctaaa                                              25

<210> SEQ ID NO 62
<211> LENGTH: 28
<212> TYPE: DNA
<213> ORGANISM: Artificial sequence
<220> FEATURE:
<223> OTHER INFORMATION: Synthetic Construct - amplification primer

<400> SEQUENCE: 62
agagtgtagt tgtaagattt aatagagt                                           28
```

METHOD FOR IN VITRO DIAGNOSIS OR PROGNOSIS OF TESTICULAR CANCER

This is a continuation of application Ser. No. 13/138,000 filed Sep. 23, 2011, which is a continuation of application Ser. No. 12/918,166 filed Aug. 18, 2010, which is a National Stage Application of PCT/FR2009/050390 filed Mar. 10, 2009, and claims the benefit of French Application No. 0851619 filed Mar. 12, 2008. The entire disclosures of the prior applications are hereby incorporated by reference in their entirety.

Testicular cancer represents 1 to 2% of cancers in men, and 3.5% of urological tumors. It is the most common tumor in young men, and rare before 15 years of age and after 50 years of age. The risk is highest in patients who are seropositive for HIV. Seminoma is the most common form of testicular cancer (40%), but many other types of cancer exist, among which are embryonic carcinoma (20%), teratocarcinoma (30%) and choriocarcinoma (1%).

The diagnosis of testicular cancer is first clinical: it often presents in the form of a hard and irregular swelling of the testicle. An ultrasound confirms the intratesticular tumor and Doppler ultrasound demonstrates the increase in vascularization in the tumor. In some cases, a magnetic resonance examination (testicular MRI) can be useful. A thoracic, abdominal and pelvic scan makes it possible to investigate whether there is any lymph node involvement of the cancer. A blood sample for assaying tumor markers is virtually systematic. It makes it possible to orient the diagnosis of the type of tumor. Two main tumor markers are used and assayed in the blood: β-HCG and α-foetoprotein. However, these markers are not very specific and, furthermore, if the concentration of these markers is at physiological levels, this does not mean that there is an absence of tumor. At the current time, the final diagnosis and final prognosis are given after ablation of the affected testicle (orchidectomy), which constitutes the first stage of treatment. Next, depending on the type of cancer and on its stage, a complementary treatment by radiotherapy or chemotherapy is applied. There is therefore a real need for having markers which are specific for testicular cancer and which, in addition, make it possible to establish as early a diagnosis and prognosis as possible.

The rare event represented by the infection of a germline cell by an exogenous provirus results in the integration, into the host's genome, of a proviral DNA or provirus, which becomes an integral part of the genetic inheritance of the host. This endogenous provirus (HERV) is therefore transmissible to the next generation in Mendelien fashion. It is estimated that there are approximately a hundred or so HERV families representing approximately 8% of the human genome. Each of the families has from several tens to thousands of loci, which are the result of intracellular retrotranspositions of transcriptionally active copies. The loci of the contemporary HERV families are all replication-defective, which signifies loss of the infectious properties and therefore implies an exclusively vertical (Mendelien) transmission mode.

HERV expression has been particularly studied in three specific contexts, placentation, autoimmunity and cancer, which are associated with cell differentiation or with the modulation of immunity. It has thus been shown that the envelope glycoprotein of the ERVWE1 locus of the HERV-W family is involved in the fusion process resulting in syncytiotrophoblast formation. It has, moreover, been suggested that the Rec protein, which is a splice variant of the env gene of HERV-K, could be involved in the testicular tumorogenesis process. However, the following question has not yet been answered: are HERVs players or markers in pathological contexts?

The present inventors have now discovered and demonstrated that nucleic acid sequences belonging to loci of the HERV-W family are associated with testicular cancer and that these sequences are molecular markers for the pathological condition. The sequences identified are either proviruses, i.e. sequences containing all or part of the gag, pol and env genes flanked on the 5' and on the 3' by long terminal repeats (LTRs), or isolated LTRs. The DNA sequences identified are respectively referenced as SEQ ID Nos. 1 to 6 in the sequence listing.

The subject of the present invention is therefore a method for in vitro, diagnosis or prognosis of testicular cancer, in a biological sample from a patient suspected of suffering from testicular cancer, which comprises a step of detecting at least one expression product from at least one nucleic acid sequence of the endogenous retroviral family called HERV-W, said sequence being selected from the sequences identified in SEQ ID Nos. 1 to 6 or from the sequences which exhibit at least 99% identity, preferably at least 99.5% identity, and advantageously at least 99.6% identity, with one of the sequences identified in SEQ ID Nos. 1 to 6.

The percentage identity described above has been determined while taking into consideration the nucleotide diversity in the genome. It is known that nucleotide diversity is higher in the regions of the genome that are rich in repeat sequences than in the regions which do not contain repeat sequences. By way of example, D. A. Nickerson et al.,[1] have shown a diversity of approximately 0.3% (0.32%) in regions containing repeat sequences.

The expression product which is detected is preferably at least one mRNA transcript of at least one of the sequences SEQ ID Nos. 1 to 6, but this can also be a polypeptide which is the product of translation of at least one of said transcripts.

When the expression product is an mRNA transcript, it is detected by any suitable method, such as hybridization, sequencing or amplification. The mRNA can be detected directly by bringing it into contact with at least one probe and/or at least one primer which are designed so as to hybridize, under predetermined stringency conditions, to the mRNA transcripts, demonstrating the presence or absence of hybridization to the mRNA and, optionally, quantifying the mRNA. Among the preferred methods, mention may be made of amplification (for example, RT-PCR, NASBA, etc.) or else Northern blotting. The mRNA can also be detected indirectly on the basis of nucleic acids derived from said transcripts, such as cDNA copies, etc.

Generally, the method of the invention comprises an initial step of extracting the mRNA from the sample to be analyzed.

First, the method can comprise:
(i) a step of extracting the mRNA from the sample to be analyzed,
(ii) a step of detecting and quantifying the mRNA of the sample to be analyzed,
(iii) a step of extracting the mRNA from a healthy sample,
(iv) a step of detecting and quantifying the mRNA of the healthy sample,
(v) a step of comparing the amount of mRNA expressed in the sample to be analyzed and in the healthy sample; if the amount of mRNA expressed in the sample to be analyzed is determined as being greater than the amount of mRNA expressed in the healthy sample, this can be correlated with the diagnosis or prognosis of a testicular cancer;

and in particular:

(i) extraction of the RNA to be analyzed from the sample,
(ii) determination, in the RNA to be analyzed, of a level of expression of at least one RNA sequence in the sample, said RNA sequence being the product of transcription of at least one nucleic acid sequence selected from the sequences identified in SEQ ID Nos. 1 to 6 or from the sequences which include at least 99% identity, preferably at least 99.5% identity, and advantageously at least 99.6% identity, with one of the sequences identified in SEQ ID Nos. 1 to 6, and
(iii) comparison of the level of expression of said RNA sequence(s) defined in (ii) with the level of expression of said RNA sequence(s) in a noncancerous biological sample; if the level of expression of the RNA to be analyzed is determined as being greater than the level of expression of the RNA extracted from the noncancerous biological sample, this can be correlated with the diagnosis or prognosis of a testicular cancer.

The transcripts are overexpressed in testicular tumors. In order to detect such an overexpression, a reference point may be necessary, i.e. a control. The amount of mRNA in the healthy sample serves as a reference standard to which the amount of mRNA in the sample to be analyzed can be compared, it being possible for an overexpression of mRNA in the sample to be analyzed, compared with the expression of mRNA in the healthy sample, to be correlated with a diagnosis or prognosis of a testicular cancer. However, since transcription is generally negligible or even nonexistent in the healthy sample, whereas it is significantly higher in the cancer sample, a reference point is not essential, the significant expression of transcripts being an indicator of the disease.

The term "overexpressed sequence" is intended to mean an mRNA sequence which is found in greater amounts or at higher levels than those found for the same mRNA sequence derived from the same type of sample, but which is noncancerous, constituting the reference threshold value.

The sequences of said transcripts are respectively identified in SEQ ID Nos. 7 to 12 (given with reference to the genomic DNA):

SEQ ID No. 7=transcript of the HW4TT locus,
SEQ ID No. 8=transcript of the HW2TT locus,
SEQ ID No. 9=transcript of the HW13TT locus,
SEQ ID No. 10=transcript of the HWXTT locus,
SEQ ID No. 11=transcript of the HW21TT locus,
SEQ ID No. 12=transcript of the ERVWE1 locus.

When the expression product is a polypeptide derived from the translation of at least one of the transcripts, it can be detected, in the method of the invention, using at least one binding partner specific for said polypeptide, in particular an antibody, for example a monoclonal antibody. The method for producing monoclonal antibodies and the selection process are well known to those skilled in the art.

By way of illustration, polypeptide sequences are described and identified in SEQ ID Nos. 14, 16, 18, 20, 22 and 24:

SEQ ID No. 14=Gag protein of HW4TT,
SEQ ID No. 16=protease of HW4TT,
SEQ ID No. 18=Gag protein of HW2TT,
SEQ ID No. 20=protein of HW2TT,
SEQ ID No. 22=Gag protein of HW13TT,
SEQ ID No. 24=Gag protein of HW21TT
SEQ ID No. 26=Env protein of ERVWE1 (Syncytin-1).

The sample from the patient will generally comprise cells (such as the testicular cells). They may be present in a tissue sample (such as the testicular tissue) or be found in the circulation. In general, the sample is a testicular tissue extract or a biological fluid, such as blood, serum, plasma, urine or else seminal fluid.

The subject of the invention is also an isolated nucleic acid sequence which consists of:

(i) at least one DNA sequence selected from the sequences SEQ ID Nos. 1 to 6, or
(ii) at least one DNA sequence complementary to a sequence selected from the sequences SEQ ID Nos. 1 to 6, or
(iii) at least one DNA sequence which exhibits at least 99% identity, preferably at least 99.5% identity, and advantageously at least 99.6% identity, with a sequence as defined in (i) and (ii), or
(iv) at least one RNA sequence which is the product of transcription of a sequence selected from the sequences as defined in (i), or
(v) at least one RNA sequence which is the product of transcription of a sequence selected from the sequences which exhibit at least 99% identity, preferably at least 99.5% identity, and advantageously at least 99.6% identity, with a sequence as defined in (i), or
(vi) at least one RNA sequence selected from the sequences SEQ ID Nos. 7 to 12; and the use of at least one isolated nucleic acid sequence, as a molecular marker for in vitro diagnosis or prognosis of testicular cancer, in which the nucleic acid sequence consists of:

(i) at least one DNA sequence selected from the sequences SEQ ID Nos. 1 to 6, or
(ii) at least one DNA sequence complementary to a sequence selected from the sequences SEQ ID Nos. 1 to 6, or
(iii) at least one DNA sequence which exhibits at least 99% identity with a sequence as defined in (i) and (ii), or
(iv) at least one RNA sequence which is the product of transcription of a sequence selected from the sequences as defined in (i), or
(v) at least one RNA sequence which is the product of transcription of a sequence selected from the sequences which exhibit at least 99% identity with a sequence as defined in (i), or
(vi) at least one RNA sequence selected from the sequences SEQ ID Nos. 7 to 12.

FIGURES

Figure 4:
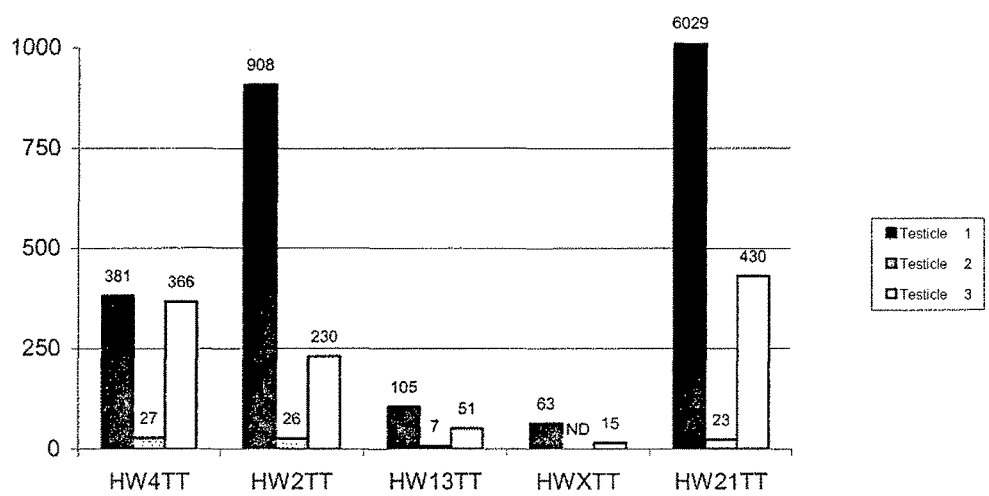
Figure 5:
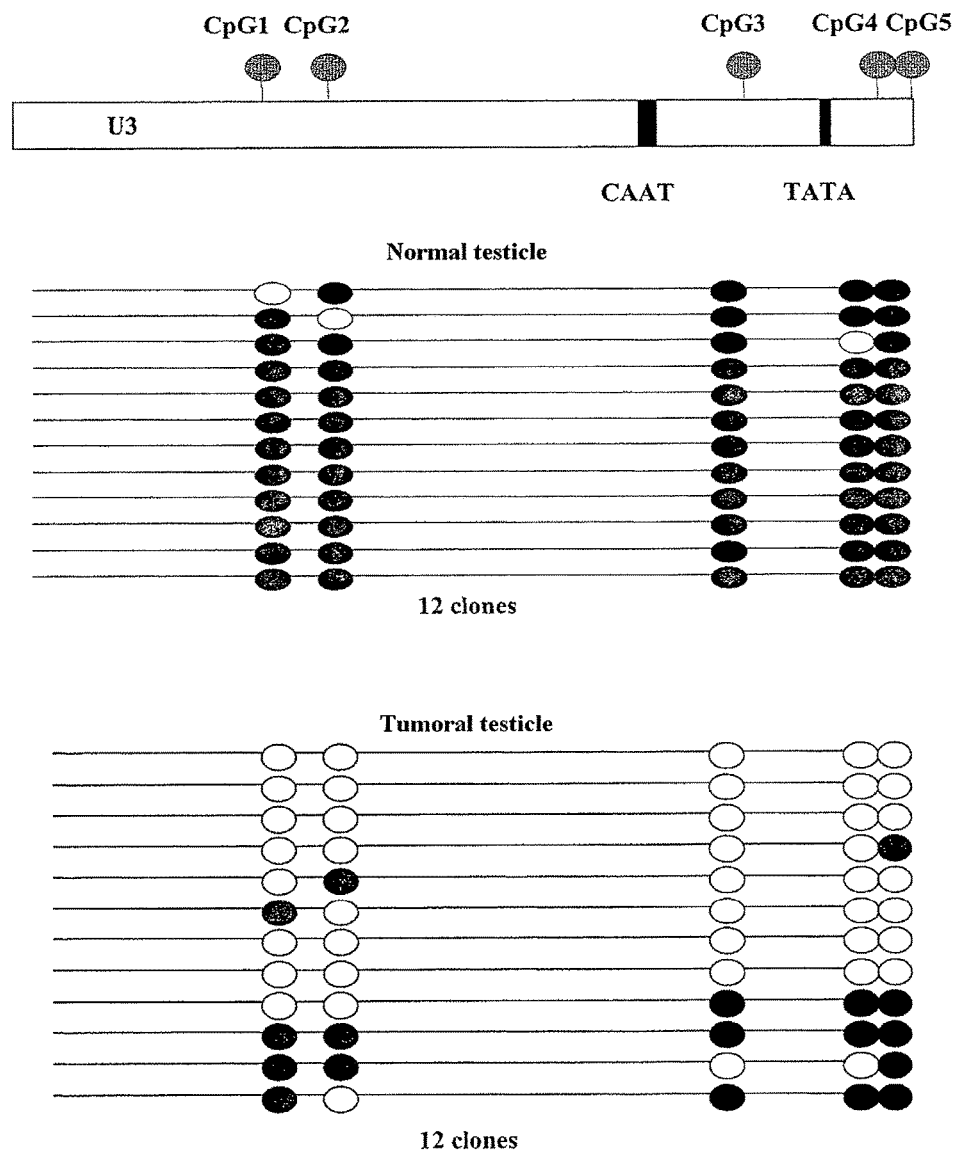
Figure 6:
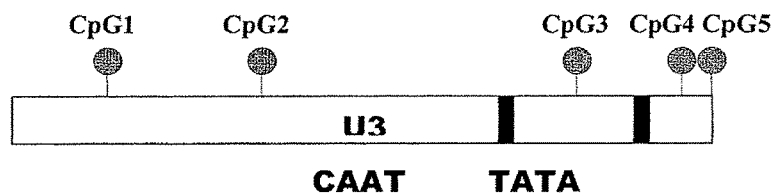
Figure 6:
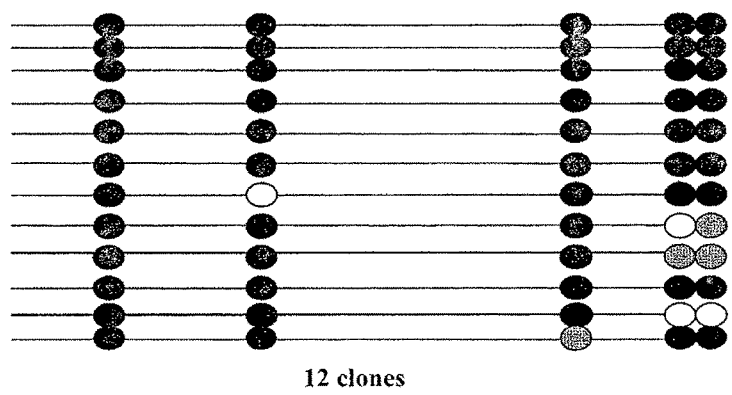
Figure 6:
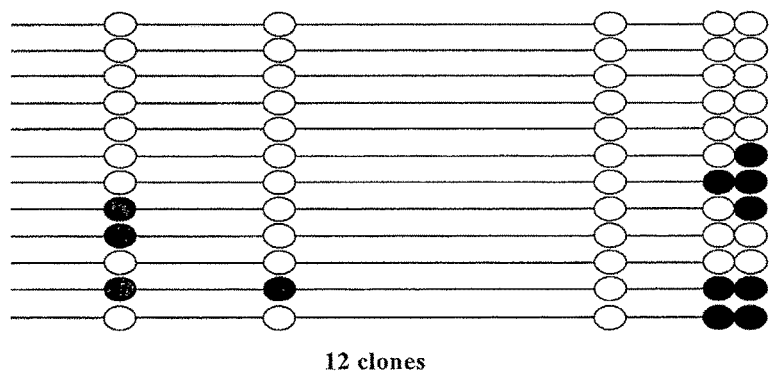
Figure 7:
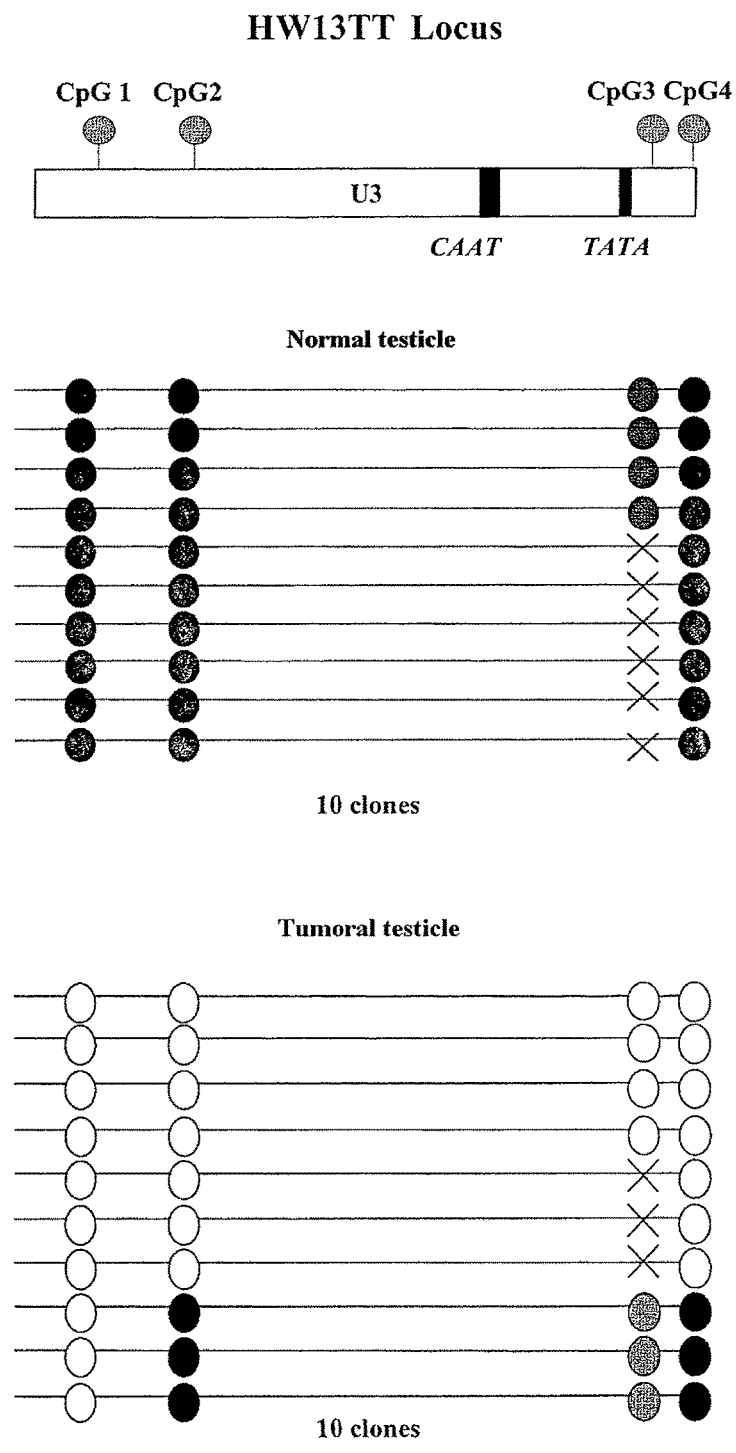
Figure 8:
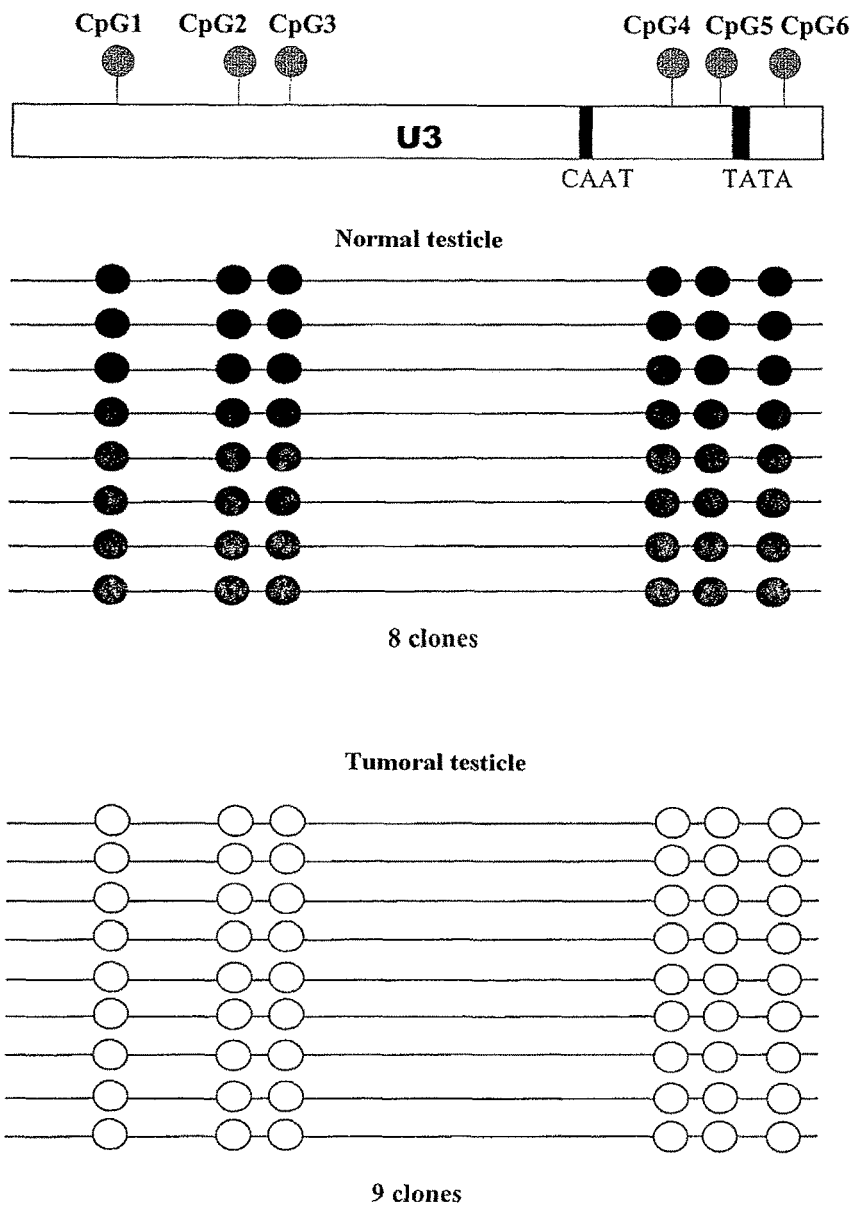
Figure 9:
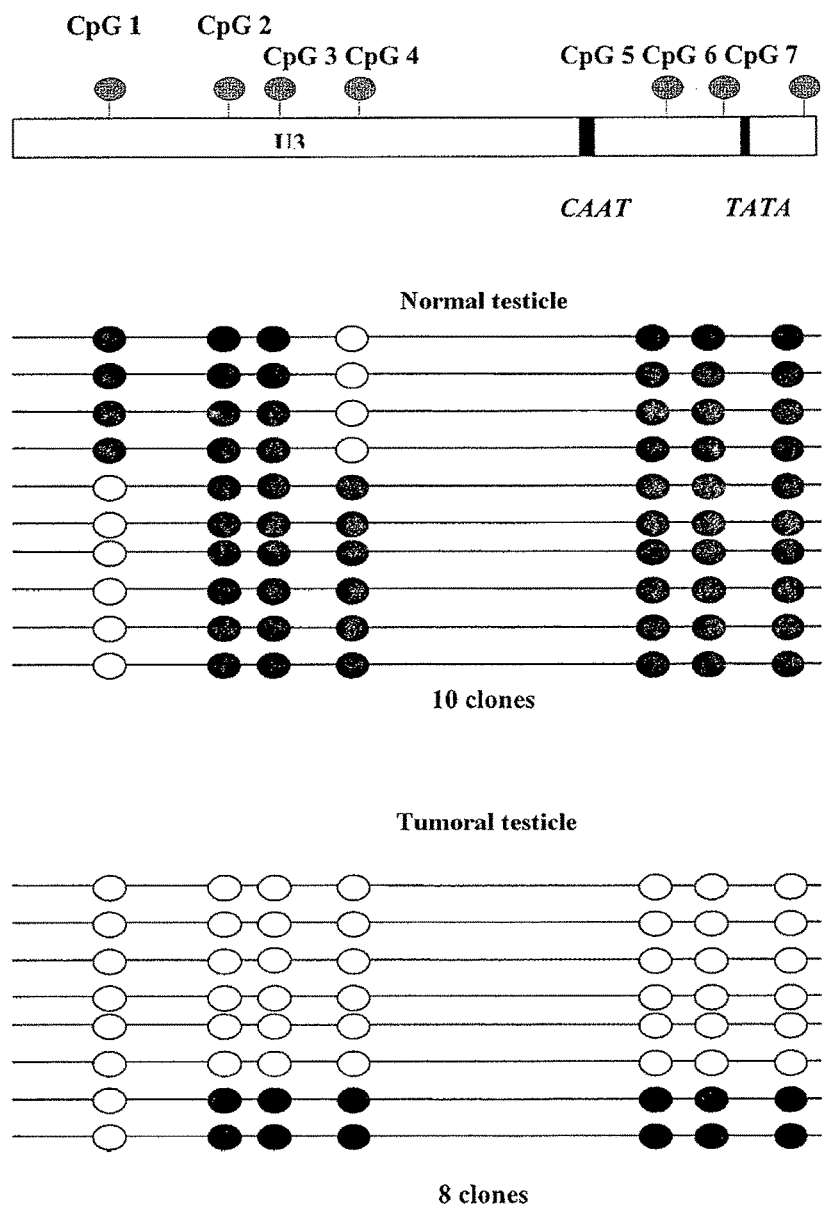
Figure 10:
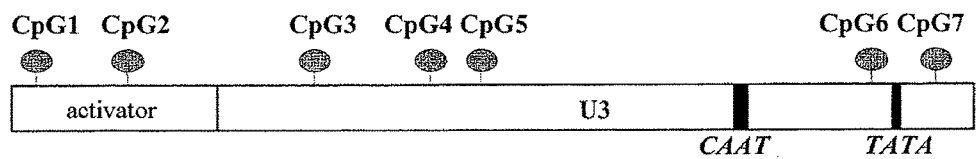
Figure 10:
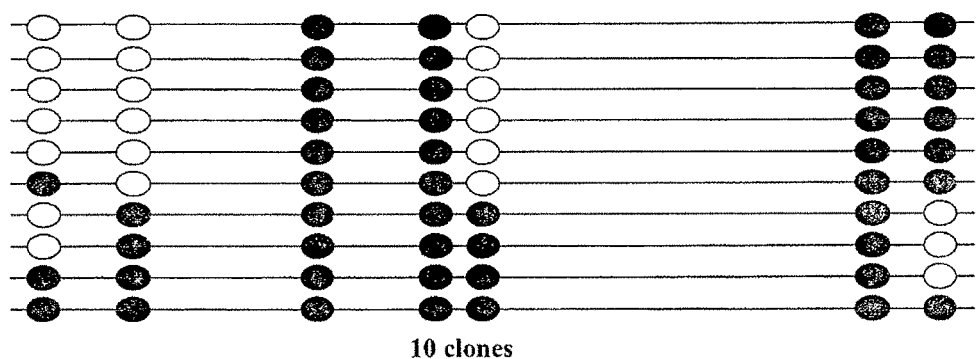
Figure 10:
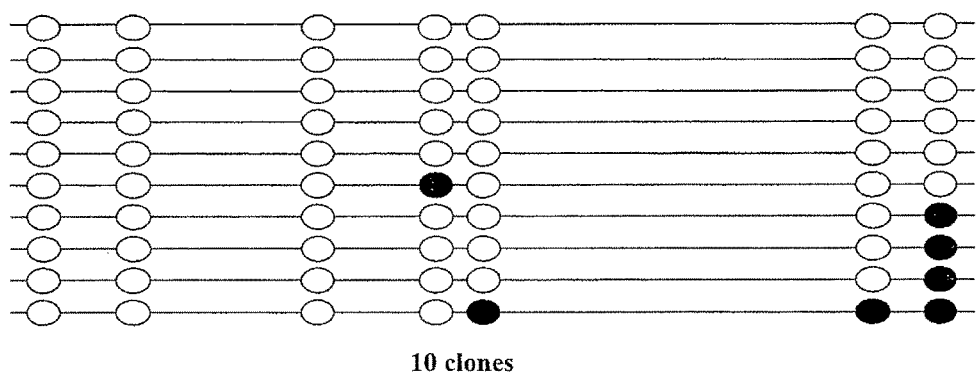

FIG. 4 is a histogram representing the increase in expression of the five loci (HW4TT, HW2TT, HW13TT, HWXTT and HW21TT), respectively, in three pairs of testicular samples (testicle 1, testicle 2 and testicle 3), based on a comparative tumor sample/healthy sample quantification. The loci are represented along the x-axis and the factors of increase of expression between tumor tissue and healthy tissue are represented along the y-axis.

FIGS. 5 to 10 represent the methylation status of the U3 region of unique LTR or of the 5' LTR of the various loci, respectively HW4TT, HW2TT, HW13TT, HWXTT, HW21TT and ERVWE1 in the healthy testicle (normal) and in the tumoral testicle derived from the same patient, after amplification and analysis of the sequences obtained.

EXAMPLES

Example 1: Identification of HERV-W Loci Expressed in Cancerous Tissues

Method:

The identification of expressed HERV-W loci is based on the design of a high-density DNA chip in the GeneChip format proposed by the company Affymetrix. It is a specially developed, custom-made chip, the probes of which correspond to HERV-W loci. The sequences of the HERV-W family were identified from the GenBank nucleic databank using the Blast algorithm (Altschul et al., 1990) with the sequence of the ERVWE1 locus, located on chromosome 7 at 7q21.2 and encoding the protein called syncytin. The sequences homologous to HERV-W were compared to a library containing reference sequences of the HERV-W family (ERVWE1) cut up into functional regions (LTR, gag, pol and env), using the RepeatMasker software (A. F. A. Smit and P. Green). These elements constitute the HERVgDB bank.

The probes making up the high-density chip were defined on a criterion of uniqueness of their sequences in the HERVgDB bank. The HERV-W proviral and solitary LTRs contained in the HERVgDB bank were extracted. Each of these sequences was broken down into a set of sequences of 25 nucleotides (25-mers) constituting it, i.e. as many potential probes. The evaluation of the uniqueness of each probe was carried out by means of a similarity search with all the 25-mers generated for all the LTRs of the family under consideration. This made it possible to identify all the 25-mers of unique occurrence for each family of HERV. Next, some of these 25-mers were retained as probes. For each U3 or U5 target region, a set of probes was formed on the basis of the probes identified as unique.

Figure 1:
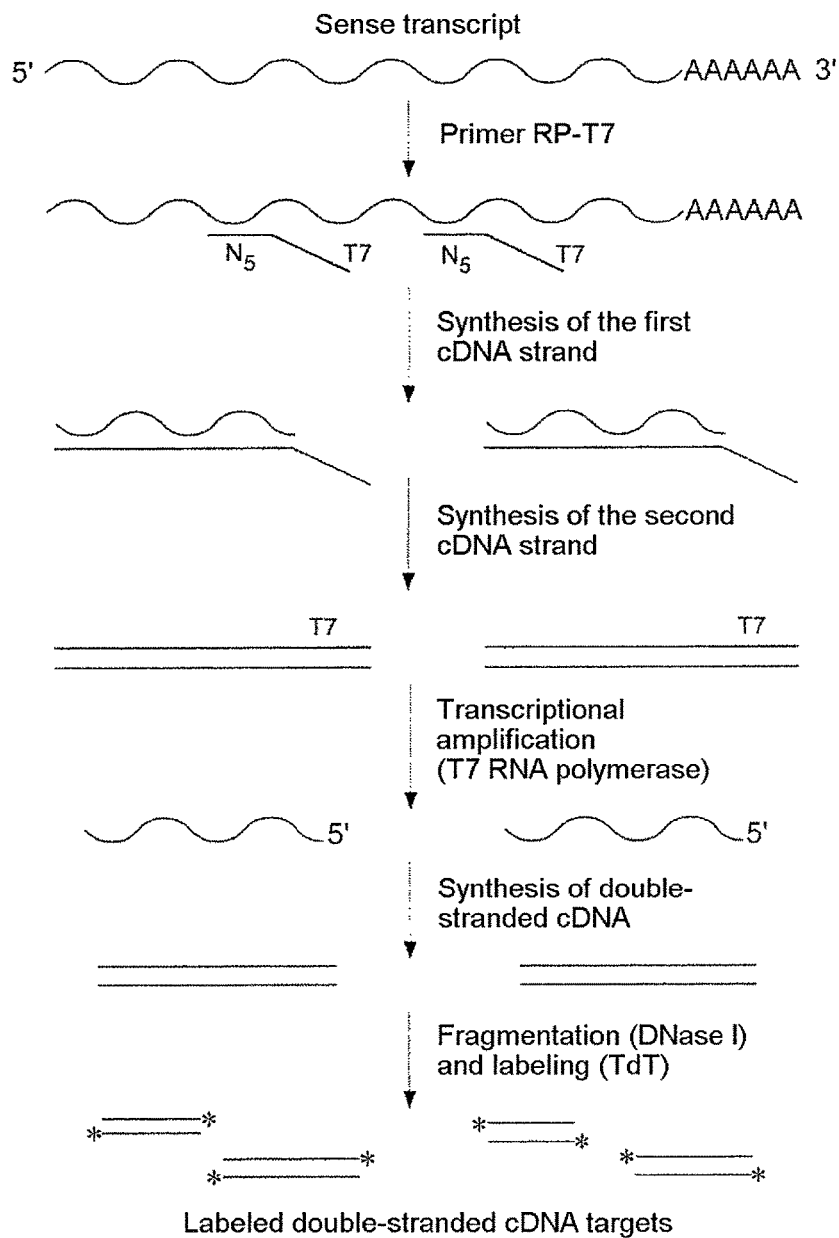
FIG. 1 represents the principle of the WTA method for amplifying RNAs.

The samples analyzed using the HERV high-density chip correspond to RNAs extracted from tumors and to RNAs extracted from the healthy tissues adjacent to these tumors. The tissues analyzed are: uterus, colon, lung, breast, testicle, prostate and ovary. Placental RNAs (health tissue only) were also analyzed. For each sample, 400 ng of total RNA were amplified by means of an unbiased transcriptional method known as WTA. The principle of WTA amplification is the following: primers (RP-T7) comprising a random sequence and a T7 promoter sequence are hybridized to the transcripts; double-standard cDNAs are synthesized and serve as a template for transcriptional amplification by the T7 RNA polymerase; the antisense RNAs generated are converted to double-stranded cDNAs which are then fragmented and labeled by introducing biotinylated nucleotide analogs at the 3'OH ends using terminal transferase (TdT) (cf. FIG. 1).

Figure 2:
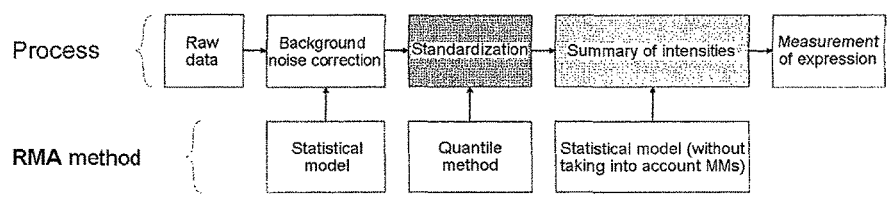
FIG. 2 represents a synoptic scheme of the nature and the sequence of the various steps for preprocessing DNA-chip data according to the RMA method.

For each sample, 16 µg of biotin-labeled amplification products were hybridized to a DNA chip according to the protocol recommended by the company Affymetrix. The chips were then washed and labeled, according to the recommended protocol. Finally, the chips were read by a scanner in order to acquire the image of their fluorescence. The image analysis carried out using the GCOS software makes it possible to obtain numerical values of fluorescence intensity which are preprocessed according to the RMA method (cf.: FIG. 2) before being able to carry out a statistical analysis in order to identify the HERV loci specifically expressed in certain samples.

Comparison of the means of more than two classes of samples was carried out by the SAM procedure applied to a Fisher test.

Figure 3:
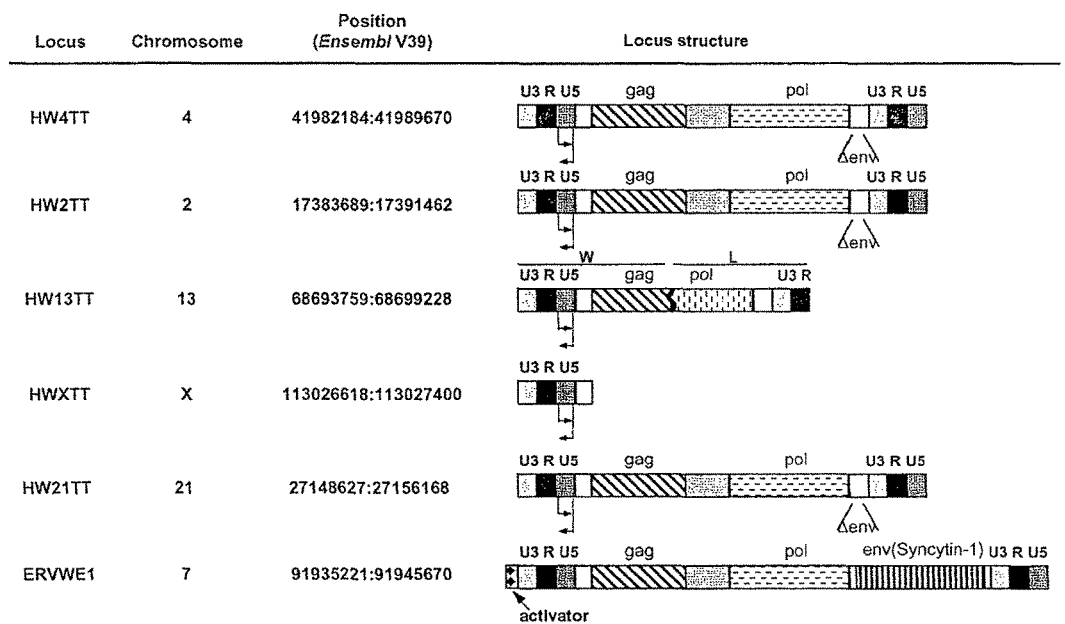
FIG. 3 illustrates the nomenclature, the position and the structure of the HERV-W loci overexpressed and exhibiting a loss of methylation in the tumoral testicle.

Results:

The processing of the data generated by the analysis on DNA chip using this method made it possible to identify six sets of probes corresponding to an overexpression in just one sample: the tumoral testicle. These five sets of probes are specific for six precise loci referenced HW4TT, HW2TT, HW13TT, HWXTT, HW21TT and ERVWE1 (cf.: FIG. 3). These six loci therefore represent markers for testicular cancer. Their nucleotide sequences are respectively identified in SEQ ID Nos. 1 to 6 in the sequence listing and the nucleotide sequences of their respective transcripts are identified in SEQ ID Nos. 7 to 12 in the sequence listing.

The information relating to the abovementioned six loci are summarized in Table 1 below.

TABLE 1

| Locus | SEQ ID No: | Chromosome | Position* |
|---|---|---|---|
| HW4TT | 1 | 4 | 41982184:41989670 |
| HW2TT | 2 | 2 | 17383689:17391462 |
| HW13TT | 3 | 13 | 68693759:68699228 |
| HWXTT | 4 | X | 113026618:113027400 |
| HW21TT | 5 | 21 | 27148627:27156168 |
| ERVWE1 | 6 | 7 | 91935221:91945670 |

*Position relative to ensemble version No. 39 (June 2006) (NCBI No. 36)
http://www.ensembl.org/Homo_sapiens/index.html The HW13TT locus is a chimeric provirus of HERV-W/L type resulting from the recombination of an HERV-W provirus and an HERV-L provirus. This chimera is such that the 5' region made up of the sequence starting from the beginning of the 5' LTR to the end of the determined gag fragment is of W type and the 3' region made up of the sequence starting from the subsequent pol fragment to the end of the 3' LTR (U3-R only) is of L type. This results in a fusion of the 3' gag W-5' pol L regions.

A search of open reading frames (ORFs) of at least 150 bases, using the Mac Vector 9.5.2 software, based on the identification of a start codon and of a stop codon, was carried out and the corresponding polypeptides identified.

The ORF1 of HW4TT identified in SEQ ID No. 13 encodes a Gag protein identified in SEQ ID No. 14 and the ORF 2 of HW4TT (SEQ ID No. 15) encodes a protease (SEQ ID No. 16), the ORF1 of HW2TT identified in SEQ ID No. 17 encodes a Gag protein identified in SEQ ID No. 18 and the ORF 2 of HW2TT (SEQ ID No. 19) encodes a protein identified in SEQ ID No. 20, the ORF of HW13TT identified in SEQ ID No. 21 encodes a Gag protein identified in SEQ ID No. 22, the ORF of HW21TT identified in SEQ ID No. 23 encodes a Gag protein identified in SEQ ID No. 24, the ORF of ERVWE1 identified in SEQ ID No. 25 encodes an Env protein identified in SEQ ID No. 26.

Example 2: Validation of the Loci Overexpressed in the Tumoral Testicle and Determination of the Associated Induction Factor Principle:

Five of the six loci identified as overexpressed in the tumoral testicle by means of the high-density HERV chip were validated by real-time RT-PCR on three pairs of testicular samples. The specificity of this overexpression is evaluated by analyzing samples originating from other tissues. To this end, specific amplification systems were developed and used for the loci identified, as described in Table 2 below.

TABLE 2

| Locus | Sense primer (SEQ ID No:) | Antisense primer (SEQ ID No:) |
|---|---|---|
| G6PD gene | TGCAGATGCTGTGTCTGG (27) | CGTACTGGCCCAGGACC (28) |
| HW4TT | GGTTCGTGCTAATTGAGCTG (29) | ATGGTGGCAAGCTTCTTGTT (30) |
| HW2TT | TGAGCTTTCCCTCACTGTCC (31) | TGTTCGGCTTGATTAGGATG (32) |
| HW13TT | CATGGCCCAATATTCCATTC (33) | GGTCCTTGTTCACAGAACTCC (34) |
| HWXTT | CCGCTCCTGATTGGACTAAA (35) | CGTGGGTCAAGGAAGAGAAC (36) |
| HW21TT | ATGACCCGCAGCTTCTAACAG (37) | CTCCGCTCACAGAGCTCCTA (38) |

The expression of these loci is standardized with respect to that of a suitable housekeeping gene: G6PD. This quantification of expression was carried out using an Mx3005P real-time RT-PCR machine, marketed by the company Stratagene.

Results:

The study of the three pairs of testicular samples indicates that the five loci identified, with the exception of HWXTT, the expression of which could not be quantified in the second testicular RNA pair, are overexpressed in the tumoral testicle compared with the health tissue (cf.: FIG. 4). The very marked nature of the overexpression, i.e. a low or even absent transcriptional expression in the healthy testicle and a high expression in the tumoral testicle, reveals the possibility of an epigenic method of regulation of transcription of these loci.

The analysis of pairs of samples originating from other tissues (colon, uterus, breast, ovary, lung and prostate) shows that the overexpression phenomenon is restricted to the tumoral testicle. Consequently, the expression of the identified loci assumes the nature of a marker specific for testicular cancer.

Example 3: Epigenetic Control of Transcription

Principle:

DNA methylation is an epigenetic modification which takes place, in eukaryotics, by the addition of a methyl group to the cytosines of 5'-CpG dinucleotides, and results in transcriptional repression when this modification occurs within the nucleotide sequence of a promoter. Apart from a few exceptions, human endogenous sequences of retroviral origin are restricted, owing to this methylation process, to a silent transcriptional state in the cells of the organism under physiological conditions.

In order to analyze the methylation status of the unique LTR or of the 5' LTR of the five loci, the "bisulfite sequencing PCR" method was used. This method makes it possible, on the basis of sequencing a representative sample of the population, to identify the methylation state of each CG dinucleotide on each of the sequences within the tissue studied. Since the methylation information is lost during the amplification steps, it is advisable to translate the methylation information actually within the nucleotide sequence by means of the method of treating the genomic DNA with sodium bisulfite. The action of the bisulfite (sulfonation), followed by hydrolytic deamination and then alkaline desulfonation, in fact makes it possible to modify all the cytosines contained in the genomic DNA, into uracil. The speed of deamination of sulfonated cytosines (C) is, however, much higher than that of the sulfonated 5-methyl-Cs. It is therefore possible, by limiting the reaction time to 16 hours, to convert strictly the non-methylated cytosines to uracil (U), while at the same time preserving the cytosines which have a methyl group. After the sodium bisulfite treatment, the sequence of interest is amplified from the genomic DNA derived from the tumoral testicular section and from that derived from the adjacent healthy testicular section, by polymerase chain reaction (PCR) in two stages. The first PCR enables a specific selection of the sequence of interest, the second, "nested", PCR makes it possible to amplify this sequence.

Since the DNA sequence had been modified by the bisulfite, the design of the primers took into account the code change (C to U), and the primers were selected so as to hybridize to a region containing no CpG (their methylation state, and therefore their conversion state, being a priori unknown).

The sequences of the primers used are described in Tables 3 to 8 below.

TABLE 3

| | HW4TT locus | |
|---|---|---|
| Amplification | Sense primer 5'→3' (SEQ ID No.:) | Antisense primer 5'→3' (SEQ ID No.:) |
| First PCR | CCAACATCACTAACACAACCT (39) | GGGAGTTAGTAAGGGGTTTG (40) |
| Nested PCR | CAACCTATTAAACAAAACTAAATT (41) | AGATTTAATAGAGTGAAAATAGAGTTT (42) |

TABLE 4

HW2TT locus

| Amplification | Sense primer 5'→3' (SEQ ID No.:) | Antisense primer 5'→3' (SEQ ID No.:) |
|---|---|---|
| First PCR | TTATTAGTTTAGGGGATAGTTG (43) | ACACAATAAACAACCTACTAAAT (44) |
| Nested PCR | GAGGGTAAGTGGTGATAAA (45) | AACCTACTAAATCCAAAAAA (46) |

TABLE 5

HW13TT locus

| Amplification | Sense primer 5'→3' (SEQ ID No.:) | Antisense primer 5'→3' (SEQ ID No.:) |
|---|---|---|
| First PCR | TAGGATTTTAGGTTTATTGTTA (47) | AAAAATAAAATATTAAACC (48) |
| Nested PCR | ATATGTGGGAGTGAGAGATA (49) | CAACAACAAACAATAATAATAA (50) |

TABLE 6

HWXTT locus

| Amplification | Sense primer 5'→3' (SEQ ID No.:) | Antisense primer 5'→3' (SEQ ID No.:) |
|---|---|---|
| First PCR | TTGAGTTTTTTTATTGATAGTG (51) | TCTAAATCCTATTTTCCTACT (52) |
| Nested PCR | GTTTTTTTATTGATAGTGAGAGAT (53) | TAACAAACCTTTAATCCAAT (54) |

TABLE 7

HW21TT locus

| Amplification | Sense primer 5'→3' (SEQ ID No.:) | Antisense primer 5'→3' (SEQ ID No.:) |
|---|---|---|
| First PCR | TTTAGTGAGGATGATGTAATAT (55) | CAACTTAATAAAAATAAACCCA (56) |
| Nested PCR | ATAATGTTTTAGTAAGTGTTGGAT (57) | ACAATTACAAACCTTTAACC (58) |

TABLE 8

ERVWE1 locus

| Amplification | Sense primer 5'→3' (SEQ ID No.:) | Antisense primer 5'→3' (SEQ ID No.:) |
|---|---|---|
| First PCR | AATTCATTCAACATCCATTC (59) | GGTTTAATATTATTTATTATTTTGGA (60) |
| Nested PCR | CTCTTACCTTCCTATACTCTCTAAA (61) | AGAGTGTAGTTGTAAGATTTAATAGAGT (62) |

After extraction on a gel and purification, the amplicons are cloned into plasmids, and the latter are used to transform competent bacteria. About twelve plasmid DNA mini preparations are carried out using the transformed bacteria and the amplicons contained in the plasmids are sequenced. The sequences obtained are then analyzed (cf.: FIGS. 5 to 10).

Results:

The analysis of the 5' region of the transcripts of the loci identified was carried out by means of the 5' Race technique. It in particular made it possible to show that the transcription is started at the beginning of the R region of the proviral 5' LTR. This reflects the existence of a promoter role for the U3 region of the proviral 5' LTR.

1. Methylation state of the U3 sequences of the 5' LTR of the HW4TT locus:

The U3 sequence of the 5' LTR of the HW4TT locus of reference contains 5 CpG sites:

a) in the sample of healthy testicular tissue: out of 12 sequences analyzed, 9 are completely methylated. The other 3 each time exhibit 1 CpG nonmethylated out of the 5 contained in the U3 region. This therefore represents an overall methylation of the U3 region of the 5' LTR of the HW4TT locus amounting to 95% in the healthy testicular sample;

b) in the sample of tumoral testicular tissue: out of 12 sequences analyzed, 5 (i.e. 41.66% of the sequences) are completely demethylated, 3 sequences have 4 CpGs out of 5 nonmethylated, 2 sequences have 2 CpGs out of 5 nonmethylated, 1 sequence has 1 CpG out of 5 nonmethylated, and 1 sequence remains completely methylated. This therefore represents an overall methylation of the U3 region of the 5' LTR of the HW4TT locus amounting to 30% in the tumoral testicular sample.

2. Methylation state of the U3 sequences of the 5' LTR of the HW2TT locus:

The U3 sequence of the 5' LTR of the HW2TT locus of reference contains 5 CpG sites:

a) in the sample of healthy testicular tissue: out of 12 sequences analyzed, 9 are completely methylated, 1 has its $2^{nd}$ CpG nonmethylated, 1 has the CpG at position 4 nonmethylated, 1 has the CpGs at positions 4 and 5 nonmethylated, and 3 sequences have point mutations on one or two CpGs (one in position 3, one in position 5 and one in positions 4 and 5), very probably reflecting PCR artifacts. This therefore represents an overall methylation of the U3 region of the 5' LTR of the HW2TT locus amounting to 92.9% in the healthy testicular sample;

b) in the sample of tumoral testicular tissue: out of 12 sequences analyzed, 6 are completely demethylated, 5 sequences have one or two methylated CpG(s) (1 at position 1, 1 other at position 5, 1 on positions 1 and 5, 2 at positions 4 and 5 and 1 at position 3). Finally, one sequence has 4 CpGs methylated out of 5 (positions 1, 2, 4 and 5). This corresponds to an overall methylation of the U3 region of the 5' LTR of the HW2TT locus amounting to 20% in the tumoral testicular sample.

3. Methylation state of the U3 sequences of the 5' LTR of the HW13TT locus:

The U3 sequence of the 5' LTR of the HW13TT locus of reference contains 3 CpG sites:

a) in the sample of healthy testicular tissue: an additional CpG, compared with the reference sequence, is found in 4 of the 10 clones studied for this locus. It is located between CpGs 2 and 3 and is methylated. In the other 6 clones, this site is mutated compared with the reference sequence. The other 3 CpGs of the U3 region are methylated in the 10 sequences analyzed. This therefore represents an overall methylation of the U3 region of the 5' LTR of the HW13TT locus amounting to 100% in the healthy testicular sample;

b) in the sample of tumoral testicular tissue: the additional CpG indicated above is also found. It is demethylated in 4 of the 10 sequences analyzed, mutated in 3 other sequences, and its methylation state is indeterminate in the last 3 sequences. 7 sequences out of 10 are completely demethylated and the other 3 are methylated on the $2^{nd}$ and on the $3^{rd}$ CpG. This corresponds to an overall methylation of the U3 region of the 5' LTR of the HW13TT locus amounting to 20% in the tumoral testicular sample.

4. Methylation state of the U3 sequences of the solitary LTR of the HWXTT locus:

The U3 sequence of the 5' LTR of the HWXTT locus of reference contains 6 CpG sites:

a) in the sample of healthy testicular tissue: the 8 sequences analyzed are completely methylated, which corresponds to a methylation percentage of 100% in the healthy testicular sample;

b) in the sample of tumoral testicular tissue: the 9 sequences analyzed 6 are completely demethylated, which corresponds to a methylation percentage of 0%.

5. Methylation state of the U3 sequences of the 5' LTR of the HW21TT locus:

The U3 sequence of the 5' LTR of the HW21TT locus of reference contains 7 CpG sites:

a) in the sample of healthy testicular tissue: the 10 sequences analyzed all have 6 CpGs methylated out of 7; for 6 of the sequences, the $1^{st}$ CpG is nonmethylated and for the other 4 sequences, the $4^{th}$ CpG is nonmethylated. This therefore represents an overall methylation of the U3 region of the 5' LTR of the HW21TT locus amounting to 85.7% in the healthy testicular sample;

b) in the sample of tumoral testicular tissue: out of 8 sequences analyzed, 6 are completely demethylated, 2 others exhibit a profile identical to one of those found in the healthy testicular tissue, namely 6 CpGs methylated and the $1^{st}$ CpG nonmethylated. This corresponds to an overall methylation of the U3 region of the 5' LTR of the HW21TT locus amounting to 21.4% in the tumoral testicular sample.

6. Methylation state of the sequences of the activator of the U3 of the 5' LTR of the ERVWE1 locus:

The ERVWE1 locus comprises, in addition to its U3 promoter region, a known activator located directly upstream of the 5' LTR, and which contains two CpG sites (CpG 1 and 2). The U3 sequence of the 5' LTR of the ERVWE1 locus of reference contains, for its part, 5 CpG sites (CpGs 3 to 7):

a) in the sample of healthy testicular tissue: out of 10 sequences analyzed, 5 sequences have CpGs 1 and 2 (activator) and 5 (U3) nonmethylated, 1 sequence has CpGs 2 and 5 nonmethylated, 2 sequences have CpGs 1 (activator) and 7 (U3) nonmethylated, 1 sequence has CpG 7 only nonmethylated and, finally, 1 is completely methylated for the 7 CpGs. In total, this corresponds to a methylation percentage of 68.57% in the healthy testicular sample;

b) in the sample of tumoral testicular tissue: out of the 10 sequences analyzed, only 3 sequences exhibit, for each one, a unique methylated CpG (CpG 4 or CpG5 or CpG6), the other 7 sequences are completely demethylated, which corresponds to a methylation percentage of 4.29%.

The very high level of methylation of the U3 retroviral promoters of the loci considered, in the healthy tissue, is correlated with the low, or even absent, transcription expression of the U5 regions which correspond to the loci considered, indicating a repression of the transcriptional expression by an epigenetic mechanism. On the other hand, the low level of methylation of these same promoters in the tumoral tissue reflects a lifting of transcriptional inhibition, the result of which is the significantly higher expression demonstrated by means of the high-density HERV DNA chip and by means of the real-time RT-PCR.

LITERATURE REFERENCES

[1] Nickerson D. A. et al., DNA sequence diversity in a 9.7-kb region of the human lipoprotein lipase gene, Nature Genetics, Vol. 19, pp 233-240 (1998).

[2] Cottrell S. E., Molecular diagnostic applications of DNA methylation technology, Clinical Biochemistry 37, pp 595-604 (2004).

The invention claimed is:

1. A method of detecting at least one HERV-W mRNA transcript, comprising:
obtaining a biological sample that is collected from a person suspected of suffering from testicular cancer; and
detecting whether one or more HERV-W mRNA transcripts are expressed by assaying the biological sample,
wherein the one or more HERV-W mRNA transcripts include an HERV-W mRNA transcript expressed from a genomic sequence having at least 99% sequence identity with SEQ ID NO: 4.

2. The method of claim 1, further comprising detecting whether an HERV-W mRNA transcript is expressed from a genomic sequence having at least 99% sequence identity with SEQ ID NO: 1.

3. The method of claim 1, further comprising detecting whether an HERV-W mRNA transcript is expressed from a genomic sequence having at least 99% sequence identity with SEQ ID NO: 2.

4. The method of claim 1, further comprising detecting whether an HERV-W mRNA transcript is expressed from a genomic sequence having at least 99% sequence identity with SEQ ID NO: 3.

5. The method of claim 1, further comprising detecting whether an HERV-W mRNA transcript is expressed from a genomic sequence having at least 99% sequence identity with SEQ ID NO: 3 SEQ ID NO: 5.

6. The method of claim 1, further comprising detecting whether an HERV-W mRNA transcript is expressed from a genomic sequence having at least 99% sequence identity with SEQ ID NO: 6.

7. The method of claim 1, wherein the biological sample is a testicular sample.

8. The method of claim 1, wherein the person has a hard and irregular swelling of a testicle.

9. The method of claim 1, wherein expression of the one or more HERV-W mRNA transcripts is detected by hybridization, amplification, or sequencing.

10. The method of claim 1, wherein expression of the one or more HERV-W mRNA transcripts is detected by detecting cDNA obtained from the one or more HERV-W mRNA transcripts.

11. A method of detecting at least one HERV-W mRNA transcript, comprising:
obtaining a biological sample that is collected from a person suspected of suffering from testicular cancer; and
detecting whether one or more HERV-W mRNA transcripts are expressed by assaying the biological sample,
wherein the one or more HERV-W mRNA transcripts include an HERV-W mRNA transcript having at least 99% sequence identity with SEQ ID NO: 10.

12. The method of claim 11, further comprising detecting whether an HERV-W mRNA transcript having at least 99% sequence identity with SEQ ID NO: 7 is expressed.

13. The method of claim 11, further comprising detecting whether an HERV-W mRNA transcript having at least 99% sequence identity with SEQ ID NO: 8 is expressed.

14. The method of claim 11, further comprising detecting whether an HERV-W mRNA transcript having at least 99% sequence identity with SEQ ID NO: 9 is expressed.

15. The method of claim 11, further comprising detecting whether an HERV-W mRNA transcript having at least 99% sequence identity with SEQ ID NO: 11 is expressed.

16. The method of claim 11, further comprising detecting whether an HERV-W mRNA transcript having at least 99% sequence identity with SEQ ID NO: 12 is expressed.

17. The method of claim 11, wherein the biological sample is a testicular sample.

18. The method of claim 11, wherein expression of the one or more HERV-W mRNA transcripts is detected by detecting cDNA obtained from the one or more HERV-W mRNA transcripts.

19. A method of detecting HERV-W mRNA transcripts, comprising:
obtaining a biological sample that is collected from a person suspected of suffering from testicular cancer; and
assaying the biological sample to detect whether an HERV-W mRNA transcript is expressed from each of:
(i) a first genomic sequence having at least 99% sequence identity with SEQ ID NO: 1;
(ii) a second genomic sequence having at least 99% sequence identity with SEQ ID NO: 2;
(iii) a third genomic sequence having at least 99% sequence identity with SEQ ID NO: 3;
(iv) a fourth genomic sequence having at least 99% sequence identity with SEQ ID NO: 4;
(v) a fifth genomic sequence having at least 99% sequence identity with SEQ ID NO: 5; and
(vi) a sixth genomic sequence having at least 99% sequence identity with SEQ ID NO: 6.

20. The method of claim 19, wherein:
(i) the first genomic sequence has at least 99.5% sequence identity with SEQ ID NO: 1;

(ii) the second genomic sequence has at least 99.5% sequence identity with SEQ ID NO: 2;
(iii) the third genomic sequence has at least 99.5% sequence identity with SEQ ID NO: 3;
(iv) the fourth genomic sequence has at least 99.5% sequence identity with SEQ ID NO: 4;
(v) the fifth genomic sequence has at least 99.5% sequence identity with SEQ ID NO: 5; and
(vi) the sixth genomic sequence has at least 99.5% sequence identity with SEQ ID NO: 6.

21. The method of claim 19, wherein:
(i) the first genomic sequence has at least 99.6% sequence identity with SEQ ID NO: 1;
(ii) the second genomic sequence has at least 99.6% sequence identity with SEQ ID NO: 2;
(iii) the third genomic sequence has at least 99.6% sequence identity with SEQ ID NO: 3;
(iv) the fourth genomic sequence has at least 99.6% sequence identity with SEQ ID NO: 4;
(v) the fifth genomic sequence has at least 99.6% sequence identity with SEQ ID NO: 5; and
(vi) the sixth genomic sequence has at least 99.6% sequence identity with SEQ ID NO: 6.

22. The method of claim 19, wherein the biological sample is a testicular sample.

23. The method of claim 22, wherein the person has a hard and irregular swelling of a testicle.

24. A method of detecting HERV-W mRNA transcripts, comprising:
    obtaining a biological sample that is collected from a person suspected of suffering from testicular cancer; and
    assaying the biological sample to detect whether each of the following is expressed:
    (i) a first HERV-W mRNA transcript having at least 99% sequence identity with SEQ ID NO: 7;
    (ii) a second HERV-W mRNA transcript having at least 99% sequence identity with SEQ ID NO: 8;
    (iii) a third HERV-W mRNA transcript having at least 99% sequence identity with SEQ ID NO: 9;
    (iv) a fourth HERV-W mRNA transcript having at least 99% sequence identity with SEQ ID NO: 10;
    (v) a fifth HERV-W mRNA transcript having at least 99% sequence identity with SEQ ID NO: 11; and
    (vi) a sixth HERV-W mRNA transcript having at least 99% sequence identity with SEQ ID NO: 12.

\* \* \* \* \*